(12) United States Patent
Albertsen et al.

(10) Patent No.: US 7,759,543 B2
(45) Date of Patent: Jul. 20, 2010

(54) NUCLEOTIDE SEQUENCES MEDIATING PLANT MALE FERTILITY AND METHOD OF USING SAME

(75) Inventors: Marc Albertsen, Grimes, IA (US); Tim Fox, Des Moines, IA (US); Gary Huffman, Des Moines, IA (US); Mary Trimnell, West Des Moines, IA (US); Youngzhon Wu, Johnston, IA (US); Howard Hershey, Cumming, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 12/564,665

(22) Filed: Sep. 22, 2009

(65) Prior Publication Data

US 2010/0017905 A1 Jan. 21, 2010

Related U.S. Application Data

(60) Division of application No. 11/471,202, filed on Jun. 20, 2006, now Pat. No. 7,612,251, which is a continuation-in-part of application No. 11/166,609, filed on Jun. 24, 2005, now Pat. No. 7,517,975, which is a continuation-in-part of application No. 10/412,000, filed on Apr. 11, 2003, now Pat. No. 7,151,205, which is a continuation of application No. 09/670,153, filed on Sep. 26, 2000, now abandoned.

(51) Int. Cl.
C12N 15/82 (2006.01)
C12N 15/29 (2006.01)
C12N 15/53 (2006.01)
C12N 15/56 (2006.01)
A01H 1/02 (2006.01)

(52) U.S. Cl. ............ 800/274; 800/278; 800/282; 800/287; 800/300; 435/8; 435/189; 435/204

(58) Field of Classification Search ............ None
See application file for complete search history.

(56) References Cited

U.S. PATENT DOCUMENTS

| | | |
|---|---|---|
| 5,409,823 A | 4/1995 | Crossland et al. |
| 5,432,068 A | 7/1995 | Albertsen |
| 5,478,369 A | 12/1995 | Albertsen |
| 5,608,142 A | 3/1997 | Barton |
| 5,689,041 A | 11/1997 | Mariani |
| 5,689,051 A | 11/1997 | Cigan |
| 5,750,867 A | 5/1998 | Williams et al. |
| 5,750,868 A | 5/1998 | Cigan |
| 5,837,850 A | 11/1998 | Huffman |
| 5,859,341 A | 1/1999 | Albertsen |
| 5,880,331 A | 3/1999 | Krebbers |
| 5,977,433 A | 11/1999 | Williams |
| 6,008,437 A | 12/1999 | Williams |
| 6,037,523 A | 3/2000 | Albertsen et al. |
| 6,288,302 B1 | 9/2001 | Yu et al. |
| 6,743,968 B2 | 6/2004 | Dellaporta |
| 6,753,139 B1 | 6/2004 | Baulcombe |
| 7,071,375 B2 | 7/2006 | Brown et al. |
| 7,098,388 B2 | 8/2006 | Albertsen |
| 7,151,205 B2 | 12/2006 | Albertsen et al. |
| 2003/0175965 A1 | 9/2003 | Lowe et al. |
| 2005/0120416 A1 | 6/2005 | Perez |
| 2005/0246796 A1 | 11/2005 | Cigan |
| 2006/0141495 A1 | 6/2006 | Wu et al. |
| 2006/0288440 A1 | 12/2006 | Albertsen |
| 2007/0209085 A1 | 9/2007 | Wu et al. |
| 2008/0244765 A1 | 10/2008 | Zhao et al. |

FOREIGN PATENT DOCUMENTS

| | | |
|---|---|---|
| WO | WO9201366 A1 | 2/1992 |
| WO | WO9325695 | 12/1993 |
| WO | WO9529247 A1 | 11/1995 |
| WO | WO9613588 A1 | 5/1996 |
| WO | WO9617945 A1 | 6/1996 |
| WO | WO9640925 A2 | 12/1996 |

(Continued)

OTHER PUBLICATIONS

Unger et al. (2002) "A chimeric ecdysone receptor facilitates methoxyfenozide-dependent restoration of male fertility in ms45 maize" Transgenic Research 11:455-465.

(Continued)

*Primary Examiner*—David T Fox
(74) *Attorney, Agent, or Firm*—Patricia A. Sweeney

(57) ABSTRACT

Nucleotide sequences mediating male fertility in plants are described, with DNA molecule and amino acid sequences set forth. Promoter sequences and their essential regions are also identified. The nucleotide sequences are useful in mediating male fertility in plants. In one such method, the homozygous recessive condition of male sterility causing alleles is maintained after crossing with a second plant, where the second plant contains a restoring transgene construct having a nucleotide sequence which reverses the homozygous condition. The restoring sequence is linked with a hemizygous sequence encoding a product inhibiting formation or function of male gametes. The maintainer plant produces only viable male gametes which do not contain the restoring transgene construct. Increase of the maintainer plant is also provided by self-fertilization, and selection for seed or plants which contain the construct.

48 Claims, 34 Drawing Sheets

FOREIGN PATENT DOCUMENTS

| | | |
|---|---|---|
| WO | WO9854340 A1 | 12/1998 |
| WO | WO9859061 A1 | 12/1998 |
| WO | WO0106845 A2 | 2/2001 |
| WO | WO0226789 A2 | 4/2002 |
| WO | WO02052924 A2 | 7/2002 |
| WO | WO03057848 A2 | 7/2003 |
| WO | WO03076632 | 9/2003 |
| WO | WO2007002267 A1 | 1/2007 |

OTHER PUBLICATIONS

Unger et al. "Selection and orientation of adjacent genes influences DAM-mediated male sterlity in transformed maize" Transgenic Research (2001) 10:409-422.

Wesley et al. (2001) "Construct tesing for efficient, effective and high-throughput gene silencing in plants" The Plant Journal, 27(6): 581-590.

Iyer et al. (2000) "Transgene silencing in monocots" Plant Molecular Biology, 43:323-346.

Kapoor (2002) "Silencing of tapetum-specific zinc finger gene TAZ1 causes premature denegration of tapetum and pollen abortion in petunia" The Plant Cell. vol. 14, 2353-2367.

Smith et al. (2000) "Total silencing by intron-spliced hairpin RNAs" nature vol. 407: 319-320.

Waterhouse et al. (2003) "Exploring plant genomes by RNA-induced gene silencing" Nature Reviews, vol. 4: 29-38.

Mette et al. (2000) "Transcriptional silencing and promoter methylation triggered by double-stranded RNA" The EMBO Journal, vol. 19: 5194-5201.

Kooter et al. (1999) "Listening to the silent genes: transgene silencing, gene regulation and pathogen control" Trends in Plant Science, vol. 4 No. 9, pp. 340-347.

Cigan et al. (2001) "Phenotypic complementation of ms45 maize requires tapetal expression of MS45" Sex Plant Reprod. 14:135-142.

Sijen et al. (2001) "Transcritpional and posttranscriptional gene silencing are mechanistically related" Current Biology, 11:436-440.

Burgess et al. (2002) "A novel two-component system for cell lethality and its use in engineering nuclear male sterility in plants" The Plant Journal, 31(1): 113-125.

Luo et al. (2000) "FLP-mediated recombination for use in hybrid plant production" The Plant Journal, 23(3): 423-430.

Bortiri et al. (2006) "Advances in maize genomics: the emergence of positional cloning" Current Opinion in Plant Biology, vol. 9, No. 2: 164-167.

Hessel et al. (2007 "Dual testcross QTL analysis: a solution to the current rate-limiting steps of positionally cloning QTL in maize" 49th Annual Maize Genetics Conference [Online] 2007, p. 130, XP02478550.

Williams et al. (2006) "Map based cloning of the nsfl (nicosulfuron susceptible 1) gene of maize" 48th Annual maize Genetics Conference [Online] XP002478551.

Singh et al., Genetics 143(1):505-516 (May 1996).

Araya et al., pp. 93-91 in Plant Mitochondria, Brennicke A. et al. eds. VCH:Weinheim Germany (1993).

Chen et al., Sexual Plant Reproduction 13(2):85-94 (2000).

Williams (1995) Trends Biotechnol. 12, 344-349.

Perez-Prat (2002)"Hybrid seed production and the challenge of propagating male-sterile plants" Trends Plant Sci. 7, No. 5 1999-203.

Loukides et al. (1995) Amer. J. Botany 82:1017-1026.

West and Albertsen (1985) "Three new male sterile genes" Maize Newsletter 59:87.

Fox EMBL Acc. No. AF366297 May 15, 2001.

Benveniste et al. (2006) Plant Science 170:326-338.

Wereck-Reichart et al. (2000) Genome Biol. 1:1-9.

Buell et al. (2002) Genbank Accession No. AAL84318.

Lin et al. (2001) Genbank Accession No. AAG60111.

Williams et al. (2006) "map-based cloning of the nsfl (nicosulfuron susceptible 1) gene of maize" 48th Annual maize Genetics Conference [Online] XP002478551.

Guo et al. (2004) Proc. Natl. Acad Sci. USA 101:9205-9210.

Lisch (2002) Trends Plant Sci. 7:498-504.

Feldmann (1991) Plant J. 1:71-82.

Cone et al. (1988) Basic Life Sci. 47:149-159.

Donald (1990) EMBO J. 9:1717-1726.

Hao (1998) J. Biol. Chem 273:26857-26861.

Rebers (1999) Insect Biochem. Mol. 29:293-302.

Vrati (1996) Virology 220:186-199.

Millar (2001) Molecular Psychiatry 6:173-176.

Aranda-Agustin Nucleic Acids Res 26:4588-4596, (1998).

Tang (1999) Plant Cell 11:177-189.

Arndt (1997) Genome 40:785-797.

Colliver (1997) Plant Mol. Biol. 35:509-522.

Klann (1996) Plant Physiol. 112:1321-1330.

Lazar (1998) Mol. Cell Biol. 8:1247-1252.

Hill (1998) Biochem Biophys. Res. Comm 244:573-577.

Hessel et al. (2007) "Dual testcross QTL analysis: a solution to the current rate-limiting steps of positionally cloning QTL in maize" 49th Annual Maize Genetics Conference, [Online] 2007, p. 130, XP002478550.

Bortiri et al. (2006) "Advances in maize genomics: the emergence of positional cloning" Current Opinion in Plant Biology vol. 9, No. 2: 164-167.

Wu et al.,Accession No. AFK71507, SEQ ID No. 5942 of US20060141495, Jun. 29, 2006.

Figure 4A

```
    EcoRI
      |
      GAATTCGGCACGAGGGAAGCTCACCTCACGCCGGCGACGCCATCGCCATTCTTCCCACTA
   1  ---------+---------+---------+---------+---------+---------+ 60
      CTTAAGCCGTGCTCCCTTCGAGTGGAGTGCGGCCGCTGCGGTAGCGGTAAGAAGGGTGAT a     E  F  G  T  R  E  A  H  L  T  P  A  T  P  S  P  F  F  P  L  -

GCAGGGCCTCACAAGTACATCGCGCTCCTTCTGGTTGTCCTCTCATGGATCCTGGTCCAG
  61  ---------+---------+---------+---------+---------+---------+ 120
      CGTCCCGGAGTGTTCATGTAGCGCGAGGAAGACCAACAGGAGAGTACCTAGGACCAGGTC a     A  G  P  H  K  Y  I  A  L  L  L  V  V  L  S  W  I  L  V  Q  -

AGGTGGAGCCTGAGGAAGCAGAAAGGCCCGAGATCATGGCCAGTCATCGGCGCAACGGTG
 121  ---------+---------+---------+---------+---------+---------+ 180
      TCCACCTCGGACTCCTTCGTCTTTCCGGGCTCTAGTACCGGTCAGTAGCCGCGTTGCCAC a     R  W  S  L  R  K  Q  K  G  P  R  S  W  P  V  I  G  A  T  V  -

GAGCAGCTGAGGAACTACCACCGGATGCACGACTGGCTTGTCGGGTACCTGTCACGGCAC
 181  ---------+---------+---------+---------+---------+---------+ 240
      CTCGTCGACTCCTTGATGGTGGCCTACGTGCTGACCGAACAGCCCATGGACAGTGCCGTG a     E  Q  L  R  N  Y  H  R  M  H  D  W  L  V  G  Y  L  S  R  H  -

AGGACAGTGACCGTCGACATGCCGTTCACTTCCTACACCTACATCGCTGACCCGGTGAAT
 241  ---------+---------+---------+---------+---------+---------+ 300
      TCCTGTCACTGGCAGCTGTACGGCAAGTGAAGGATGTGGATGTAGCGACTGGGCCACTTA a     R  T  V  T  V  D  M  P  F  T  S  Y  T  Y  I  A  D  P  V  N  -

GTCGAGCATGTCCTCAAGACTAACTTCACCAATTACCCCAAGGGAATCGTGTACAGATCC
 301  ---------+---------+---------+---------+---------+---------+ 360
      CAGCTCGTACAGGAGTTCTGATTGAAGTGGTTAATGGGGTTCCCTTAGCACATGTCTAGG a     V  E  H  V  L  K  T  N  F  T  N  Y  P  K  G  I  V  Y  R  S  -

TACATGGACGTGCTCCTCGGTGACGGCATCTTCAACGCCGACGGCGAGCTGTGGAGGAAG
 361  ---------+---------+---------+---------+---------+---------+ 420
      ATGTACCTGCACGAGGAGCCACTGCCGTAGAAGTTGCGGCTGCCGCTCGACACCTCCTTC a     Y  M  D  V  L  L  G  D  G  I  F  N  A  D  G  E  L  W  R  K  -

CAGAGGAAGACGGCGAGTTTCGAGTTCGCCTCCAAGAACCTGAGGGATTTCAGCGCCATT
 421  ---------+---------+---------+---------+---------+---------+ 480
      GTCTCCTTCTGCCGCTCAAAGCTCAAGCGGAGGTTCTTGGACTCCCTAAAGTCGCGGTAA a     Q  R  K  T  A  S  F  E  F  A  S  K  N  L  R  D  F  S  A  I  -
```

Figure 4B

```
      GTGTTCAGAGAGTACTCCCTGAAGCTGTCGGGTATACTGAGCCAGGCATCCAAGGCAGGC
  481 ---------+---------+---------+---------+---------+---------+ 540
      CACAAGTCTCTCATGAGGGACTTCGACAGCCCATATGACTCGGTCCGTAGGTTCCGTCCG a     V  F  R  E  Y  S  L  K  L  S  G  I  L  S  Q  A  S  K  A  G   -

AAAGTTGTGGACATGCAGGAACTTTACATGAGGATGACGCTGGACTCCATCTGCAAGGTT
  541 ---------+---------+---------+---------+---------+---------+ 600
      TTTCAACACCTGTACGTCCTTGAAATGTACTCCTACTGCGACCTGAGGTAGACGTTCCAA a     K  V  V  D  M  Q  E  L  Y  M  R  M  T  L  D  S  I  C  K  V   -

GGGTTCGGGGTCGAGATCGGCACGCTGTCGCCAGATCTCCCCGAGAACAGCTTCGCGCAG
  601 ---------+---------+---------+---------+---------+---------+ 660
      CCCAAGCCCCAGCTCTAGCCGTGCGACAGCGGTCTAGAGGGGCTCTTGTCGAAGCGCGTC a     G  F  G  V  E  I  G  T  L  S  P  D  L  P  E  N  S  F  A  Q   -

GCGTTCGATGCCGCCAACATCATCATCACGCTGCGGTTCATCGACCCGCTGTGGCGCATC
  661 ---------+---------+---------+---------+---------+---------+ 720
      CGCAAGCTACGGCGGTTGTAGTAGTAGTGCGACGCCAAGTAGCTGGGCGACACCGCGTAG a     A  F  D  A  A  N  I  I  I  T  L  R  F  I  D  P  L  W  R  I   -

AAGAGGTTCTTCCACGTCGGGTCAGAGGCCCTCCTAGCGCAGAGCATCAAGCTCGTGGAC
  721 ---------+---------+---------+---------+---------+---------+ 780
      TTCTCCAAGAAGGTGCAGCCCAGTCTCCGGGAGGATCGCGTCTCGTAGTTCGAGCACCTG a     K  R  F  F  H  V  G  S  E  A  L  L  A  Q  S  I  K  L  V  D   -

GAGTTCACCTACAGCGTGATCCGCCGGAGGAAGGCCGAGATCGTCGAGGTCCGGGCCAGC
  781 ---------+---------+---------+---------+---------+---------+ 840
      CTCAAGTGGATGTCGCACTAGGCGGCCTCCTTCCGGCTCTAGCAGCTCCAGGCCCGGTCG a     E  F  T  Y  S  V  I  R  R  R  K  A  E  I  V  E  V  R  A  S   -

GGCAAACAGGAGAAGATGAAGCACGACATCCTGTCACGGTTCATCGAGCTGGGCGAGGCC
  841 ---------+---------+---------+---------+---------+---------+ 900
      CCGTTTGTCCTCTTCTACTTCGTGCTGTAGGACAGTGCCAAGTAGCTCGACCCGCTCCGG a     G  K  Q  E  K  M  K  H  D  I  L  S  R  F  I  E  L  G  E  A   -

GGCGACGACGGCGGCGGCTTCGGGGACGATAAGAGCCTCCGGGACGTGGTGCTCAACTTC
  901 ---------+---------+---------+---------+---------+---------+ 960
      CCGCTGCTGCCGCCGCCGAAGCCCCTGCTATTCTCGGAGGCCCTGCACCACGAGTTGAAG a     G  D  D  G  G  G  F  G  D  D  K  S  L  R  D  V  V  L  N  F   -

GTGATCGCCGGGCGGGACACGACGGCGACGACGCTGTCGTGGTTCACGCACATGGCCATG
  961 ---------+---------+---------+---------+---------+---------+ 1020
      CACTAGCGGCCCGCCCTGTGCTGCCGCTGCTGCGACAGCACCAAGTGCGTGTACCGGTAC a     V  I  A  G  R  D  T  T  A  T  T  L  S  W  F  T  H  M  A  M   -
```

Figure 4C

```
      TCCCACCCGGACGTGGCCGAGAAGCTGCGCCGCGAGCTGTGCGCGTTCGAGGCGGAGCGC
1021  ---------+---------+---------+---------+---------+---------+ 1080
      AGGGTGGGCCTGCACCGGCTCTTCGACGCGGCGCTCGACACGCGCAAGCTCCGCCTCGCG a      S  H  P  D  V  A  E  K  L  R  R  E  L  C  A  F  E  A  E  R   -

GCGCGCGAGGAGGGCGTCACGCTCGTGCTCTGCGGCGGCGCTGACGCCGACGACAAGGCG
1081  ---------+---------+---------+---------+---------+---------+ 1140
      CGCGCGCTCCTCCCGCAGTGCGAGCACGAGACGCCGCCGCGACTGCGGCTGCTGTTCCGC a      A  R  E  E  G  V  T  L  V  L  C  G  G  A  D  A  D  D  K  A   -

TTCGCCGCCCGCGTGGCGCAGTTCGCGGGCCTCCTCACCTACGACAGCCTCGGCAAGCTG
1141  ---------+---------+---------+---------+---------+---------+ 1200
      AAGCGGCGGGCGCACCGCGTCAAGCGCCCGGAGGAGTGGATGCTGTCGGAGCCGTTCGAC a      F  A  A  R  V  A  Q  F  A  G  L  L  T  Y  D  S  L  G  K  L   -

GTCTACCTCCACGCCTGCGTCACCGAGACGCTCCGCCTGTACCCCGCCGTCCCTCAGGAC
1201  ---------+---------+---------+---------+---------+---------+ 1260
      CAGATGGAGGTGCGGACGCAGTGGCTCTGCGAGGCGGACATGGGGCGGCAGGGAGTCCTG a      V  Y  L  H  A  C  V  T  E  T  L  R  L  Y  P  A  V  P  Q  D   -

CCCAAGGGGATCCTGGAGGACGACGTGCTGCCGGACGGGACGAAGGTGAGGGCCGGCGGG
1261  ---------+---------+---------+---------+---------+---------+ 1320
      GGGTTCCCCTAGGACCTCCTGCTGCACGACGGCCTGCCCTGCTTCCACTCCCGGCCGCCC a      P  K  G  I  L  E  D  D  V  L  P  D  G  T  K  V  R  A  G  G   -

ATGGTGACGTACGTGCCCTACTCGATGGGGCGGATGGAGTACAACTGGGGCCCCGACGCG
1321  ---------+---------+---------+---------+---------+---------+ 1380
      TACCACTGCATGCACGGGATGAGCTACCCCGCCTACCTCATGTTGACCCCGGGGCTGCGC a      M  V  T  Y  V  P  Y  S  M  G  R  M  E  Y  N  W  G  P  D  A   -

GCGAGCTTCCGGCCGGAGCGGTGGATCAACGAGGATGGCGCGTTCCGCAACGCGTCGCCG
1381  ---------+---------+---------+---------+---------+---------+ 1440
      CGCTCGAAGGCCGGCCTCGCCACCTAGTTGCTCCTACCGCGCAAGGCGTTGCGCAGCGGC a      A  S  F  R  P  E  R  W  I  N  E  D  G  A  F  R  N  A  S  P   -

TTCAAGTTCACGGCGTTCCAGGCGGGGCCGAGGATCTGCCTGGGCAAGGACTCGGCGTAC
1441  ---------+---------+---------+---------+---------+---------+ 1500
      AAGTTCAAGTGCCGCAAGGTCCGCCCCGGCTCCTAGACGGACCCGTTCCTGAGCCGCATG a      F  K  F  T  A  F  Q  A  G  P  R  I  C  L  G  K  D  S  A  Y   -

CTGCAGATGAAGATGGCGCTGGCCATCCTCTTCCGCTTCTACAGCTTCCGGCTGCTGGAG
1501  ---------+---------+---------+---------+---------+---------+ 1560
      GACGTCTACTTCTACCGCGACCGGTAGGAGAAGGCGAAGATGTCGAAGGCCGACGACCTC a      L  Q  M  K  M  A  L  A  I  L  F  R  F  Y  S  F  R  L  L  E   -
```

Figure 4D

```
     GGGCACCCGGTGCAGTACCGCATGATGACCATCCTCTCCATGGCGCACGGCCTCAAGGTC
1561 ---------+---------+---------+---------+---------+---------+ 1620
     CCCGTGGGCCACGTCATGGCGTACTACTGGTAGGAGAGGTACCGCGTGCCGGAGTTCCAG a    G  H  P  V  Q  Y  R  M  M  T  I  L  S  M  A  H  G  L  K  V  -

CGCGTCTCTAGGGCCGTCTGATGTCATGGCGATTTGGATATGGATATCGTCCCGCTTAAT
1621 ---------+---------+---------+---------+---------+---------+ 1680
     GCGCAGAGATCCCGGCAGACTACAGTACCGCTAAACCTATACCTATAGCAGGGCGAATTA a    R  V  S  R  A  V  *  C  H  G  D  L  D  M  D  I  V  P  L  N  -

CCACGACAAATAACGCTCGTGTTACAAATTTGCATGCATGCATGTAAGGGAAAGCGATGG
1681 ---------+---------+---------+---------+---------+---------+ 1740
     GGTGCTGTTTATTGCGAGCACAATGTTTAAACGTACGTACGTACATTCCCTTTCGCTACC a    P  R  Q  I  T  L  V  L  Q  I  C  M  H  A  C  K  G  K  R  W  -

GTTTCATTGGTGGCTTGGCTTAAGCCTTAAAAACTCCGTCGGGTCTTGCGAACCACCACA
1741 ---------+---------+---------+---------+---------+---------+ 1800
     CAAAGTAACCACCGAACCGAATTCGGAATTTTTGAGGCAGCCCAGAACGCTTGGTGGTGT a    V  S  L  V  A  W  L  K  P  *

TCACTAGTGTTTTGTACTCTACTCCTCAGTGGAAGTGTAGTGACAGCATACAAGTTCATC
1801 ---------+---------+---------+---------+---------+---------+ 1860
     AGTGATCACAAAACATGAGATGAGGAGTCACCTTCACATCACTGTCGTATGTTCAAGTAG

-
                                                 XhoI
                                                  |
     ATATATATTATCCTCTTTCTTAAAAAAAAAAAAAAAAAAAACTCGAG
1861 ---------+---------+---------+---------+------ 1906
     TATATATAATAGGAGAAAGAATTTTTTTTTTTTTTTTTTTTGAGCTC
```

Figure 5A

```
   1  GAATTCCAAG CGAGGCCCTT GTAGCAGAGA GTGTTGCTGA TGCAGTCGGC
  51  GGAAATGAGT GCGTGCTGAG AGCAACGCTG AGGGGTTCCA GGGATGGCAA
 101  TGGCTATGGC AATCGGCTAG AGGTGGAGGA CAAGGTGGTG AGGATTGGGA
 151  GGGCAACCTA TGGCAAGTTG GTGAAGAGGC ACGCAATGAG AGATCTATTC
 201  AGACTTACAC TGGATGCCGC CAACAAATTC AACCTTTAGA TTTTGATACT
 251  GTCACTCCTA CTTTATTCCT TGGTTGGGCA ACTTCCAATA GGCTCATGTT
 301  AATCAATGAT TAGTGATTAT TCAGCAAATA TTCTTGTTTG TTTGACATTT
 351  ATAATATGTG GGGTGAGACG GATTAAATAT CATCCATGAG AGCTTTATCT
 401  TCATGCTCTC TTGATTTTGG TTTCAGATCA TTCTTTCAGT GTTCACAAGA
 451  ATTTTCTCAG TTTGGTCCAT GTAATTTTTG AAGTGAGGTT CCTTAAATTT
 501  CATTATGCTT CCTTTCTTTT CTAGACTAGC AACTGCATGA CTTTTCACTT
 551  TGGGTTCACA AATTGACTCA CAAGAAAACA AATTCACTTT TGGGTTCACA
 601  AATTCCTCTT CAGGATGTAC TTTTCACTTG AACTGTCATG TATAGGAACA
 651  AGGAATGGCT CAGTTTTTAA GGAACAATGT ACAGATTTCA TTTCAGAACT
 701  CTTTCTGGTT GGTTGAGTTT CAGACTTTTT GTACCAAGCT GATGGATCAC
 751  AATACTTGTT TCCAAAGTCT GATAACAGAA ACTGGCAACT CCTAATTGAT
 801  AATAAAAAGA ATAAAATACA GTATCAGATA TCTCATTTTC TTGGTTGGCA
 851  GATCACAAAA AGGAACACAA AGGCTAAGCC TCCTACTTGT TCGGGAGTTA
 901  GGTCAGGGAC ACCATATGAA TGAAAGAAAT CTTAATTTGG GGTCACACCA
 951  AGATTGTCTC TCTCGAGGTT GGGGGGTCCC TAAGGTTGGT AGTAGCAATA
1001  CCCAATATAT CACCTAACAA ACCCAATCCA TGCTACATAC ATACATAGCA
1051  TCCATCACTT GTAGACTGGA CCCTTCATCA AGAGCACCAT GGAGGAAGCT
1101  CACATCACGC CGGCGACGCC ATCGCCATTC TTCCCACTAG CAGGGCCTCA
1151  CAAGTACATC GCGCTCCTCC TGGTTGTCCT CTCATGGATC CTGGTCCAGA
1201  GGTGGAGCCT GAGGAAGCAG AAAGGCCCGA GATCATGGCC AGTCATCGGT
1251  GCAACGGTGG AGCAGCTGAG GAACTACCAC CGGATGCACG ACTGGCTTGT
1301  CGGGTACCTG TCACGGCACA GGACAGTGAC CGTCGACATG CCGTTCACTT
1351  CCTACACCTA CATCGCTGAC CCGGTGAATG TCGAGCATGT CCTCAAGACT
```

Figure 5B

```
1401  AACTTCACCA ATTACCCCAA GGTAAATGAC CTGAACTCAC TGATGTTCAG
1451  TCTTCGGAAA TCAGAGCTGA AAGCTGAATC GAATGTGCCT GAACACCGTG
1501  TAGGGAATCG TGTACAGATC CTACATGGAC GTGCTCCTCG GTGACGGCAT
1551  CTTCAACGCC GACGGCGAGC TGTGGAGGAA GCAGAGGAAG ACGGCGAGTT
1601  TCGAGTTCGC CTCCAAGAAC CTGAGGGATT TCAGCGCCAT TGTGTTCAGA
1651  GAGTACTCCC TGAAGCTGTC GGGTATACTG AGCCAGGCAT CCAAGGCAGG
1701  CAAAGTTGTG GACATGCAGG TGAGATCACT GCTCCCTTGC CATTGCCAAC
1751  ATGAGCATTT CAACCTGAGA CACGAGAGCT ACCTTGCCGA TTCAGGAACT
1801  TTACATGAGG ATGACGCTGG ACTCCATCTG CAAGGTTGGG TTCGGGGTCG
1851  AGATCGGCAC GCTGTCGCCG GATCTCCCCG AGAACAGCTT CGCGCAGGCG
1901  TTCGATGCCG CCAACATCAT CGTCACGCTG CGGTTCATCG ACCCGCTGTG
1951  GCGCATCAAG AGGTTCTTCC ACGTCGGGTC AGAGGCCCTC CTAGCGCAGA
2001  GCATCAAGCT CGTGGACGAG TTCACCTACA GCGTGATCCG CCGGAGGAAG
2051  GCCGAGATCG TCGAGGCCCG GGCCAGCGGC AAACAGGAGA AGGTACGTGC
2101  ACATGACTGT TTCGATTCTT CAGTTCATCG TCTTGGCCGG GATGGACCTG
2151  ATCCTGATTG ATTATATATC CGTGTGACTT GTGAGGACAA ATTAAAATGG
2201  GCAGATGAAG CACGACATCC TGTCACGGTT CATCGAGCTA GGCGAGGCCG
2251  GCGACGACGG CGGCGGCTTC GGGGACGACA AGAGCCTCCG GGACGTGGTG
2301  CTCAACTTCG TGATCGCCGG GCGGGACACG ACGGCGACGA CGCTGTCGTG
2351  GTTCACGCAC ATGGCCATGT CCCACCCGGA CGTGGCCGAG AAGCTGCGCC
2401  GCGAGCTGTG CGCGTTCGAG GCGGAGCGCG CGCGCGAGGA GGGCGTCGCG
2451  CTCGTGCCCT GCGGCGGCGC TGACGCCGAC GACAAGGCGT TCGCCGCCCG
2501  CGTGGCGCAG TTCGCGGGCC TCCTCACCTA CGACAGCCTC GGCAAGCTGG
2551  TCTACCTCCA CGCCTGCGTC ACCGAGACGC TCCGCCTGTA CCCCGCCGTC
2601  CCTCAGGTGA GCGCGCCCGA CACGCGACCT CCGGTCCAGA GCACAGCATG
2651  CAGTGAGTGG ACCTGAATGC AATGCACATG CACTTGCGCG CGCGCAGGAC
2701  CCCAAGGGGA TCCTGGAGGA CGACGTGCTG CCGGACGGGA CGAAGGTGAG
2751  GGCCGGCGGG ATGGTGACGT ACGTGCCCTA CTCGATGGGG CGGATGGAGT
```

Figure 5C

```
2801    ACAACTGGGG CCCCGACGCG GCGAGCTTCC GGCCGGAGCG GTGGATCAAC
2851    GAGGATGGCG CGTTCCGCAA CGCGTCGCCG TTCAAGTTCA CGGCGTTCCA
2901    GGCGGGGCCG AGGATCTGCC TGGGCAAGGA CTCGGCGTAC CTGCAGATGA
2951    AGATGGCGCT GGCCATCCTC TTGCGCTTCT ACAGCTTCCG GCTGCTGGAG
3001    GGGCACCCGG TGCAGTACCG CATGATGACC ATCCTCTCCA TGGCGCACGG
3051    CCTCAAGGTC CGCGTCTCTA GGGCCGTCTG ATGTCATGGC GATTTGGGAT
3101    ATCATCCCGC TTAATCCTTA AAAATTTGCA TGCATGCATG TAAGGGAAAG
3151    CGATGGGTTT CATTGGTGGC TTGGCTTAAG CCTTAAAAAC TCCGTCGGGT
3201    CTTGCGAACC ACCACATCAC TAGTGTTTTG TACTCTACTC CTCAGTGGAA
3251    GTGTAGTGAC AGCATACAAG TTCATCATAT ATATTATCCT CTTTCTTCGC
3301    CGGATGCTTC CCGGGACCTT TTGGAGACCA TTACTGACAG GCGTGTGAAA
3351    AAAAGGCTTC TTCTGCGGCG AAGTTTTGGG TTCAGAGTCT TGGCGTCTTT
3401    GCAGCAGAAA AAAGGTTTGG AAGGATCTGA ACCCTGAACC GAAAATGGCT
3451    TCGGAAATAT GCTCGCATCG GGGCGGGGCC GTCACTCGGG ATGACGACAA
3501    GCCCACAAGC AGTGAGAGCG AAGCGATCTT TGGAGTTTGG AGACACTCTC
3551    GGACCCCTCG GCGCTCCGCG AGCTCATCTT CGCCTCCTCT GTCGTGTCCG
3601    TGGCGGCACC GCGCCCGCCC GCCTCGTGTT CGACCAAATC CCGCGCCCCG
3651    ACCGGTTCGT GTACAACACC CTCATCCGCG GCGCCGCGCG CAGTGACACG
3701    CCCCGGGACG CCGTATACAT CTATAAATCA TGGTATTGTA CTTTATTTTC
3751    AAACGGCCTT AACACAACCA TATTTTTATG GTAAACACGT TCAAAATTGA
3801    CACAAATTTA AAACAGGCAC AAACCGTAGC TAAACATAAG AGAATGAGAG
3851    ACAACCCAAA GGTTAGAGAT GAAATAAGCT GAGTAAACGA CGAATTC
```

Figure 6A

```
1051 TCCATCACTTGTAGACTGGACCCTTCATCAAGAGCACCATGGAGGAAGCT 1100
              |    |  || |   |||||||
   1 ..............................GAATTCGGCACGAGGGAAGCT  21

1101 CACATCACGCCGGCGACGCCATCGCCATTCTTCCCACTAGCAGGGCCTCA 1150
     |||  |||||||||||||||||||||||||||||||||||||||||||||
  22 CACCTCACGCCGGCGACGCCATCGCCATTCTTCCCACTAGCAGGGCCTCA  71

1151 CAAGTACATCGCGCTCCTCCTGGTTGTCCTCTCATGGATCCTGGTCCAGA 1200
     |||||||||||||||||| |||||||||||||||||||||||||||||||
  72 CAAGTACATCGCGCTCCTTCTGGTTGTCCTCTCATGGATCCTGGTCCAGA 121

1201 GGTGGAGCCTGAGGAAGCAGAAAGGCCCGAGATCATGGCCAGTCATCGGT 1250
     ||||||||||||||||||||||||||||||||||||||||||||||||| 
 122 GGTGGAGCCTGAGGAAGCAGAAAGGCCCGAGATCATGGCCAGTCATCGGC 171

1251 GCAACGGTGGAGCAGCTGAGGAACTACCACCGGATGCACGACTGGCTTGT 1300
     ||||||||||||||||||||||||||||||||||||||||||||||||||
 172 GCAACGGTGGAGCAGCTGAGGAACTACCACCGGATGCACGACTGGCTTGT 221

1301 CGGGTACCTGTCACGGCACAGGACAGTGACCGTCGACATGCCGTTCACTT 1350
     ||||||||||||||||||||||||||||||||||||||||||||||||||
 222 CGGGTACCTGTCACGGCACAGGACAGTGACCGTCGACATGCCGTTCACTT 271

1351 CCTACACCTACATCGCTGACCCGGTGAATGTCGAGCATGTCCTCAAGACT 1400
     ||||||||||||||||||||||||||||||||||||||||||||||||||
 272 CCTACACCTACATCGCTGACCCGGTGAATGTCGAGCATGTCCTCAAGACT 321

1401 AACTTCACCAATTACCCCAAGGTAAATGACCTGAACTCACTGATGTTCAG 1450
     |||||||||||||||||| 
 322 AACTTCACCAATTACCCCA................................ 340

.
                              .
                              .

1501 TAGGGAATCGTGTACAGATCCTACATGGACGTGCTCCTCGGTGACGGCAT 1550
      |||||||||||||||||||||||||||||||||||||||||||||||||
 341 .AGGGAATCGTGTACAGATCCTACATGGACGTGCTCCTCGGTGACGGCAT 389

1551 CTTCAACGCCGACGGCGAGCTGTGGAGGAAGCAGAGGAAGACGGCGAGTT 1600
     ||||||||||||||||||||||||||||||||||||||||||||||||||
 390 CTTCAACGCCGACGGCGAGCTGTGGAGGAAGCAGAGGAAGACGGCGAGTT 439

1601 TCGAGTTCGCCTCCAAGAACCTGAGGGATTTCAGCGCCATTGTGTTCAGA 1650
     ||||||||||||||||||||||||||||||||||||||||||||||||||
 440 TCGAGTTCGCCTCCAAGAACCTGAGGGATTTCAGCGCCATTGTGTTCAGA 489

1651 GAGTACTCCCTGAAGCTGTCGGGTATACTGAGCCAGGCATCCAAGGCAGG 1700
     ||||||||||||||||||||||||||||||||||||||||||||||||||
 490 GAGTACTCCCTGAAGCTGTCGGGTATACTGAGCCAGGCATCCAAGGCAGG 539

1701 CAAAGTTGTGGACATGCAGGTGAGATCACTGCTCCCTTGCCATTGCCAAC 1750
     |||||||||||||||||
 540 CAAAGTTGTGGACATG................................... 555
```

Figure 6B

```
1751 ATGAGCATTTCAACCTGAGACACGAGAGCTACCTTGCCGATTCAGGAACT 1800
                                              ||||||||
 556 .........................................CAGGAACT 563

1801 TTACATGAGGATGACGCTGGACTCCATCTGCAAGGTTGGGTTCGGGGTCG 1850
     ||||||||||||||||||||||||||||||||||||||||||||||||||
 564 TTACATGAGGATGACGCTGGACTCCATCTGCAAGGTTGGGTTCGGGGTCG 613

1851 AGATCGGCACGCTGTCGCCGGATCTCCCCGAGAACAGCTTCGCGCAGGCG 1900
     ||||||||||||||||||||| ||||||||||||||||||||||||||||
 614 AGATCGGCACGCTGTCGCCAGATCTCCCCGAGAACAGCTTCGCGCAGGCG 663

1901 TTCGATGCCGCCAACATCATCGTCACGCTGCGGTTCATCGACCCGCTGTG 1950
     |||||||||||||||||||| |||||||||||||||||||||||||||||
 664 TTCGATGCCGCCAACATCATCATCACGCTGCGGTTCATCGACCCGCTGTG 713

1951 GCGCATCAAGAGGTTCTTCCACGTCGGGTCAGAGGCCCTCCTAGCGCAGA 2000
     ||||||||||||||||||||||||||||||||||||||||||||||||||
 714 GCGCATCAAGAGGTTCTTCCACGTCGGGTCAGAGGCCCTCCTAGCGCAGA 763

2001 GCATCAAGCTCGTGGACGAGTTCACCTACAGCGTGATCCGCCGGAGGAAG 2050
     ||||||||||||||||||||||||||||||||||||||||||||||||||
 764 GCATCAAGCTCGTGGACGAGTTCACCTACAGCGTGATCCGCCGGAGGAAG 813

2051 GCCGAGATCGTCGAGGCCCGGGCCAGCGGCAAACAGGAGAAGGTACGTGC 2100
     ||||||||||||||| ||||||||||||||||||||||||||
 814 GCCGAGATCGTCGAGGTCCGGGCCAGCGGCAAACAGGAGA.......... 853
                                  .
                                  .
2201 GCAGATGAAGCACGACATCCTGTCACGGTTCATCGAGCTAGGCGAGGCCG 2250
       ||||||||||||||||||||||||||||||||||||||| ||||||||||
 854 ..AGATGAAGCACGACATCCTGTCACGGTTCATCGAGCTGGGCGAGGCCG 901

2251 GCGACGACGGCGGCGGCTTCGGGGACGACAAGAGCCTCCGGGACGTGGTG 2300
     ||||||||||||||||||||||||||| ||||||||||||||||||||||
 902 GCGACGACGGCGGCGGCTTCGGGGACGATAAGAGCCTCCGGGACGTGGTG 951

2301 CTCAACTTCGTGATCGCCGGGCGGGACACGACGGCGACGACGCTGTCGTG 2350
     ||||||||||||||||||||||||||||||||||||||||||||||||||
 952 CTCAACTTCGTGATCGCCGGGCGGGACACGACGGCGACGACGCTGTCGTG 1001

2351 GTTCACGCACATGGCCATGTCCCACCCGGACGTGGCCGAGAAGCTGCGCC 2400
     ||||||||||||||||||||||||||||||||||||||||||||||||||
1002 GTTCACGCACATGGCCATGTCCCACCCGGACGTGGCCGAGAAGCTGCGCC 1051

2401 GCGAGCTGTGCGCGTTCGAGGCGGAGCGCGCGCGCGAGGAGGGCGTCGCG 2450
     |||||||||||||||||||||||||||||||||||||||||||||| ||
1052 GCGAGCTGTGCGCGTTCGAGGCGGAGCGCGCGCGCGAGGAGGGCGTCACG 1101

2451 CTCGTGCCCTGCGGCGGCGCTGACGCCGACGACAAGGCGTTCGCCGCCCG 2500
     ||||||| ||||||||||||||||||||||||||||||||||||||||||
1102 CTCGTGCTCTGCGGCGGCGCTGACGCCGACGACAAGGCGTTCGCCGCCCG 1151
```

Figure 6C

```
2501 CGTGGCGCAGTTCGCGGGCCTCCTCACCTACGACAGCCTCGGCAAGCTGG 2550
     ||||||||||||||||||||||||||||||||||||||||||||||||||
1152 CGTGGCGCAGTTCGCGGGCCTCCTCACCTACGACAGCCTCGGCAAGCTGG 1201

2551 TCTACCTCCACGCCTGCGTCACCGAGACGCTCCGCCTGTACCCCGCCGTC 2600
     ||||||||||||||||||||||||||||||||||||||||||||||||||
1202 TCTACCTCCACGCCTGCGTCACCGAGACGCTCCGCCTGTACCCCGCCGTC 1251

2601 CCTCAGGTGAGCGCGCCCGACACGCGACCTCCGGTCCAGAGCACAGCATG 2650
     |||
1252 CCT............................................... 1254

2651 CAGTGAGTGGACCTGAATGCAATGCACATGCACTTGCGCGCGCGCAGGAC 2700
                                                ||||||
1255 ..........................................CAGGAC 1260

2701 CCCAAGGGGATCCTGGAGGACGACGTGCTGCCGGACGGGACGAAGGTGAG 2750
     ||||||||||||||||||||||||||||||||||||||||||||||||||
1261 CCCAAGGGGATCCTGGAGGACGACGTGCTGCCGGACGGGACGAAGGTGAG 1310

2751 GGCCGGCGGGATGGTGACGTACGTGCCCTACTCGATGGGGCGGATGGAGT 2800
     ||||||||||||||||||||||||||||||||||||||||||||||||||
1311 GGCCGGCGGGATGGTGACGTACGTGCCCTACTCGATGGGGCGGATGGAGT 1360

2801 ACAACTGGGGCCCCGACGCGGCGAGCTTCCGGCCGGAGCGGTGGATCAAC 2850
     ||||||||||||||||||||||||||||||||||||||||||||||||||
1361 ACAACTGGGGCCCCGACGCGGCGAGCTTCCGGCCGGAGCGGTGGATCAAC 1410

2851 GAGGATGGCGCGTTCCGCAACGCGTCGCCGTTCAAGTTCACGGCGTTCCA 2900
     ||||||||||||||||||||||||||||||||||||||||||||||||||
1411 GAGGATGGCGCGTTCCGCAACGCGTCGCCGTTCAAGTTCACGGCGTTCCA 1460

2901 GGCGGGGCCGAGGATCTGCCTGGGCAAGGACTCGGCGTACCTGCAGATGA 2950
     ||||||||||||||||||||||||||||||||||||||||||||||||||
1461 GGCGGGGCCGAGGATCTGCCTGGGCAAGGACTCGGCGTACCTGCAGATGA 1510

2951 AGATGGCGCTGGCCATCCTCTTGCGCTTCTACAGCTTCCGGCTGCTGGAG 3000
     ||||||||||||||||||||||| ||||||||||||||||||||||||||
1511 AGATGGCGCTGGCCATCCTCTTCCGCTTCTACAGCTTCCGGCTGCTGGAG 1560

3001 GGGCACCCGGTGCAGTACCGCATGATGACCATCCTCTCCATGGCGCACGG 3050
     ||||||||||||||||||||||||||||||||||||||||||||||||||
1561 GGGCACCCGGTGCAGTACCGCATGATGACCATCCTCTCCATGGCGCACGG 1610

3051 CCTCAAGGTCCGCGTCTCTAGGGCCGTCTGATGTCATGGCGATTTG.... 3096
     |||||||||||||||||||||||||||||||||||||||||||||
1611 CCTCAAGGTCCGCGTCTCTAGGGCCGTCTGATGTCATGGCGATTTGGATA 1660

3097 .GGATATCATCCCGCTTAATCC...................TTAAAAATT 3126
      |||||||| |||||||||||||                  ||| |||||
1661 TGGATATCGTCCCGCTTAATCCACGACAAATAACGCTCGTGTTACAAATT 1710

3127 TGCATGCATGCATGTAAGGGAAAGCGATGGGTTTCATTGGTGGCTTGGCT 3176
     ||||||||||||||||||||||||||||||||||||||||||||||||||
1711 TGCATGCATGCATGTAAGGGAAAGCGATGGGTTTCATTGGTGGCTTGGCT 1760
```

Figure 6D

```
3177 TAAGCCTTAAAAACTCCGTCGGGTCTTGCGAACCACCACATCACTAGTGT 3226
     ||||||||||||||||||||||||||||||||||||||||||||||||||
1761 TAAGCCTTAAAAACTCCGTCGGGTCTTGCGAACCACCACATCACTAGTGT 1810

3227 TTTGTACTCTACTCCTCAGTGGAAGTGTAGTGACAGCATACAAGTTCATC 3276
     ||||||||||||||||||||||||||||||||||||||||||||||||||
1811 TTTGTACTCTACTCCTCAGTGGAAGTGTAGTGACAGCATACAAGTTCATC 1860

3277 ATATATATTATCCTCTTTCTTCGCCGGATGCTTCCCGGGACCTTTTGGAG 3326
     ||||||||||||||||||||||       |             ||
1861 ATATATATTATCCTCTTTCTTAAAAAAAAAAAAAAAAAAAACTCGAG.... 1906
```

Figure 8

```
   1  GAATTCCAAG CGAGGCCCTT GTAGCAGAGA GTGTTGCTGA TGCAGTCGGC
  51  GGAAATGAGT GCGTGCTGAG AGCAACGCTG AGGGGTTCCA GGGATGGCAA
 101  TGGCTATGGC AATCGGCTAG AGGTGGAGGA CAAGGTGGTG AGGATTGGGA
 151  GGGCAACCTA TGGCAAGTTG GTGAAGAGGC ACGCAATGAG AGATCTATTC
 201  AGACTTACAC TGGATGCCGC CAACAAATTC AACCTTTAGA TTTTGATACT
 251  GTCACTCCTA CTTTATTCCT TGGTTGGGCA ACTTCCAATA GGCTCATGTT
 301  AATCAATGAT TAGTGATTAT TCAGCAAATA TTCTTGTTTG TTTGACATTT
 351  ATAATATGTG GGGTGAGACG GATTAAATAT CATCCATGAG AGCTTTATCT
 401  TCATGCTCTC TTGATTTTGG TTTCAGATCA TTCTTTCAGT GTTCACAAGA
 451  ATTTTCTCAG TTTGGTCCAT GTAATTTTTG AAGTGAGGTT CCTTAAATTT
 501  CATTATGCTT CCTTTCTTTT CTAGACTAGC AACTGCATGA CTTTTCACTT
 551  TGGGTTCACA AATTGACTCA CAAGAAAACA AATTCACTTT TGGGTTCACA
 601  AATTCCTCTT CAGGATGTAC TTTTCACTTG AACTGTCATG TATAGGAACA
 651  AGGAATGGCT CAGTTTTTAA GGAACAATGT ACAGATTTCA TTTCAGAACT
 701  CTTTCTGGTT GGTTGAGTTT CAGACTTTTT GTACCAAGCT GATGGATCAC
 751  AATACTTGTT TCCAAAGTCT GATAACAGAA ACTGGCAACT CCTAATTGAT
 801  AATAAAAAGA ATAAAATACA GTATCAGATA TCTCATTTTC TTGGTTGGCA
 851  GATCACAAAA AGGAACACAA AGGCTAAGCC TCCTACTTGT TCGGGAGTTA
 901  GGTCAGGGAC ACCATATGAA TGAAAGAAAT CTTAATTTGG GGTCACACCA
 951  AGATTGTCTC TCTCGAGGTT GGGGGGTCCC TAAGGTTGGT AGTAGCAATA
1001  CCCAATATAT CACCTAACAA ACCCAATCCA TGCTACATAC ATACATAGCA
1051  TCCATCACTT GTAGACTGGA CCCTTCATCA AGAGCACCAT GG
```

```
-180  CCCATCTCA TTTCTTGGT TGGCAGATCA CAAAAGGAA CACAAAGGCT
       LS01       LS02       LS03       LS04       LS05
-130  AAGCCTCCTA CTTGTTCGGG AGTTAGGTCA GGGACACCAT ATGAATGAAA
       LS06       LS07       LS08       LS09       LS10
 -80  GAAATCTTAA TTTGGGGTCA CACCAAGATT GTCTCTCTCG AGGTTGGGGG
       LS11       LS12       LS13       LS14       LS15
 -30  GTCCCTAAGG TTGGTAGTAG CAATACCCAA TATATCACCT AACAAACCCA
       LS16       LS17       LS18
  20  ATCCATGCTA CATACATACA TAGCATCCAT CACTTGTAGA CTGGACCCTT
  70  CATCAAGAGC ACCATGG
```

☐ = DEL −176/−92
☐ = DEL −89/−44
☐ = DEL −39/−8

```
  1 ..............................................GGAA   4
                                                  | |
201 CCGGATGCACGACTGGCTTGTCGGGTACCTGTCACGGCACAGGACAGTGA 250

5 TTCGGCTTATGCCGTTCACTTCCTACACCTACATCGCTGACCCGGTGAAT  54
              ||||||||||||||||||||||||||||||||||||||||
251 CCGTCGACATGCCGTTCACTTCCTACACCTACATCGCTGACCCGGTGAAT 300

55 GTCGAGCATGTCCTCAAGACTAACTTCACCAATTACCCCAAGGGGGACGT 104
    ||||||||||||||||||||||||||||||||||||||||||||   |||
301 GTCGAGCATGTCCTCAAGACTAACTTCACCAATTACCCCAAGGGAATCGT 350

105 GTACAGATCCTACATGGATGTGCTCCTCGGTGACGGCATATTCAACGCTG 154
    ||||||||||||||||||| |||||||||||||||||||| ||||||| |
351 GTACAGATCCTACATGGACGTGCTCCTCGGTGACGGCATCTTCAACGCCG 400

155 ACGGCGAGCTGTGGAGGAAGCAGAGGAAGACGGCGAGTTTCGAGTTCGCC 204
    ||||||||||||||||||||||||||||||||||||||||||||||||||
401 ACGGCGAGCTGTGGAGGAAGCAGAGGAAGACGGCGAGTTTCGAGTTCGCC 450

205 TCCAAGAACCTGAGGGATTTCAGTGCCAATGTTTTCAGAGAGTACTCCCT 254
    ||||||||||||||||||||||||| |||| ||| |||||||||||||||
451 TCCAAGAACCTGAGGGATTTCAGCGCCATTGTGTTCAGAGAGTACTCCCT 500

255 GAAGCTGTCGGGCATACTGAGTCAGGCATCCAAGGCAGGCAAAGTTGTTG 304
    ||||||||||||| |||||||| ||||||||||||||||||||||||| |
501 GAAGCTGTCGGGTATACTGAGCCAGGCATCCAAGGCAGGCAAAGTTGTGG 550

305 ACATGCAGGAACTTTACATGAGGATGACACTGGACTCGATCTGCAANGTT 354
    |||||||||||||||||||||||||||| |||||||| |||||||:|||
551 ACATGCAGGAACTTTACATGAGGATGACGCTGGACTCCATCTGCAAGGTT 600

355 GGGTTCGGGGTCNANATCGGCACGCTGTCNCCGGATCTCCCCGAGAACAG 404
    |||||||||||:|:|||||||||||||||:|| ||||||||||||||||
601 GGGTTCGGGGTCGAGATCGGCACGCTGTCGCCAGATCTCCCCGAGAACAG 650

405 CTTCNCCCAAGCGTTCGATGCCGCTAACATCATCGTCACNCTGCGGTTCA 454
    ||||:| || ||||||||||||||| ||||||||| ||||:|||||||||
651 CTTCGCGCAGGCGTTCGATGCCGCCAACATCATCATCACGCTGCGGTTCA 700

455 TCCACCCNCTGTGGCGCATCCAGAAGTTCTTCCCCNGTCA..........  494
    || ||||:||||||||||||| ||| ||||||||| |:
701 TCGACCCGCTGTGGCGCATCAAGAGGTTCTTCCACGTCGGGTCAGAGGCC 750
```

Percent Similarity: 92.510 Percent Identity: 90.891
Sb200-Sorghr.Pep x Sb20081.Pep February 13, 1997 11:29 ..

```
  5 MPFTSYTYIADPVNVEHVLKTNFTNYPKGDVYRSYMDVLLGDGIFNADGE  54
    |||||||||||||||||||||||||||||| |||||||||||||||||||
 87 MPFTSYTYIADPVNVEHVLKTNFTNYPKGIVYRSYMDVLLGDGIFNADGE 136

55 LWRKQRKTASFEFASKNLRDFSANVFREYSLKLSGILSQASKAGKVVDMQ 104
    |||||||||||||||||||||||:||||||||||||||||||||||||||
137 LWRKQRKTASFEFASKNLRDFSAIVFREYSLKLSGILSQASKAGKVVDMQ 186
```

Figure 12B

```
105 ELYMRMTLDSICXVGFGVXIGTLSPDLPENSFXQAFDAANIIVTLRFIHP 154
    |||||||||||| ||||| |||||||||||| |||||||||:|||||.|
187 ELYMRMTLDSICKVGFGVEIGTLSPDLPENSFAQAFDAANIIITLRFIDP 236

155 LWRIQKFF 162
    ||||.:||
237 LWRIKRFF 244
```

Figure 14

Comparison of *ms26* excision and wild-type *Ms26*

```
excis:  798 caggaccccaaggggatcctggaggacgacgtgctgccggacgggacgaaggtgagggcc  857
            ||||||||||||||||||||||||||||||||||||||||||||||||||||||||||||
Wtype: 1246 caggaccccaaggggatcctggaggacgacgtgctgccggacgggacgaaggtgagggcc 1305 excis:  858 ggcgggatggtgacgtacgtgccctactcgatggggcggatggagtacaactggggcccc  917
            ||||||||||||||||||||||||||||||||||||||||||||||||||||||||||||
Wtype: 1306 ggcgggatggtgacgtacgtgccctactcgatggggcggatggagtacaactggggcccc 1365
                                                 NciI
                                                 -----
excis:  918 gacgcggcgagcttccggccggaggcccggagcggtggatcaacgaggatggcgcgttcc  977
            |||||||||||||||||||||||||        ||||||||||||||||||||||||||||
Wtype: 1366 gacgcggcgagcttccggccgg--------agcggtggatcaacgaggatggcgcgttcc 1417 excis:  978 gcaacgcgtcgccgttcaagttcacggcgttccaggcggggccgaggatctgcctgggca 1037
            ||||||||||||||||||||||||||||||||||||||||||||||||||||||||||||
Wtype: 1418 gcaacgcgtcgccgttcaagttcacggcgttccaggcggggccgaggatctgcctgggca 1477 excis: 1038 aggactcggcgtacctgcagatgaagatggcgctggccatcctcttgcgcttctacagct 1097
            |||||||||||||||||||||||||||||||||||||||||||||| |||||||||||||
Wtype: 1478 aggactcggcgtacctgcagatgaagatggcgctggccatcctcttccgcttctacagct 1537 excis: 1098 tccggctgctggaggggcacccggtgcagtaccgcatgatgaccatcctctccatggcgc 1157
            ||||||||||||||||||||||||||||||||||||||||||||||||||||||||||||
Wtype: 1538 tccggctgctggaggggcacccggtgcagtaccgcatgatgaccatcctctccatggcgc 1597
```

Figure 15 ms26 transposon

```
CGGAGCTAGGGGTGAAAACGGGTAGGGTACCCGAAACGGGTACCGGATACGGATACTGAT
TCGGGACCATTTTTCGGATACGGATACGGGTATTTTTTAGATTCGGGACGGATACGGGTA
ATACCCGGATAGTATGGCTTCGGATTCGGGTCGGATACGGAGCGAGTACTACCCGGTAAA
TACCCGGATACTCGGGTCGGATACCGGGTACCCGGAATTCGGGTACCCGTTTTTTCTTTT
TCTGCAAAATAATATAGTTATAAAATCATAACTTTACATATGAAATCGGATGAAGATAA
AGTTTATATGAAAATTGTAGAGCTCGAAGAGATCTATAACTTTGTAGTACATCACATTTT
TGTTTAAACATATCTTTAGGCCAAAATCATTAAAATAATGTCTAAATTTATATCAAAATA
ATAGACTTTATCATTTTCATGTGGGGACTTAAGATTATATCCATGTGGGAACTTAGGATT
ATCTTTTATAAACTATTTATTAATATTGGTAACTTATTTGCAATTTTCGGTCGACGCTA
CAATATTTTTATGAATTTAATTGTATTTGATGATTTTCTACAACAAGAAATTAATAATA
CACCAAATAGCCTAAAAAATTCATGGATTTTTACGGGGACACAACATATATCCACATATA
GTTCTCAAAAACATTTGGACTATAAAATCCACAAGATGTTGGTGTTTCTTCCATTCTACT
CCCACTTATTGCGTGAGTTACATGTGAAATCATTTTATGTATCGAAGTTTCAACATAATT
AATATTTCACTTATCATTTTCATGTGGCGACTTGAGGTTTTATTTGAATAGAATGTTTAT
TTGTTTTGGTAAGCTTTTGCATTTTGGATCAAACTAGTGTATTTATGAATTTTAATTAT
ACTTTGATGATTTTATGTAGAAAGAAATTAATAATGTATAAATAGCCTCAGAAATCTATG
AAATTATACGAAGGTACAACATATGGCCACATATAGTCATAACAAATAATGGGACCATAA
AATCCACAGGATGTCAACGTTTCTTCTATTTTATTTCCACTTATTGCGTGAGTTACACGT
GAAATCACTCTAAGTATCCAAGTTTCAACATAATCAATACTTCACTTTACCATTTTTACG
TGGGAACTTGAGATTATCTTCTATTAAATGCTTATTAGTATTAATTTACTTGCAATTTCG
TGGTCGAACAAGAATATTTTTTGATAACCAATTAATGCATTATCCGACAAGTATCCGATA
TCCGATCAAATAATATCCGTATCCGTCACTTATCCGCTCGGATAAATATCCGGTCCCTGT
ATCCGTATCCGTCCCGTTTCTAACTATCCGTATCCGATCCCGAATCCGTTTTAAATACAT
TAGGGTAGGATACAGGATGAGCTAATATCCGTCCGTATCCGCCCGTTTTCACCCCTAGCC
```

```
AACTGCATGACTTTTCACTTTGGGTTCACAAATTGACTCACAAGAAAACAAATTCACTTT
TGGGTTCACAAATTCCTCTTCAGGATGTACTTTTCACTTGAAACTGTCATGTATAGGAAC
AAGGAATGGCTCAGTTTTTAAGGAACAATGTACAGATTTCATTTCAGAACTCTTTCTGGT
TGGTTGAGTTTCAGACTTTTTGTACCAAGCTGATGGATCACAATACTTGTTTCCAAAGTC
TGATAACAGAAACTGGCAACTCCTAATTGATAATAAAAAGAATAAAATACAGTATCAGAT
ATCTCATTTTCTTGGTTGGCAGATCACAAAAAGGAACACAAAGGCTAAGCCTCCTACTTG
TTCGGGAGTTAGGTCAGGGACACCATATGAATGAAAGAAATCTTAATTTGGGGTCACACC
AAGATTGTCTCTCTCGAGGTTGGGGGGTCCCTAAGGTTGGTAGTAGCAATACCCAATATA
TCACCTAACAAACCCAATCCATGCTACATACATACATAGCATCCATCACTTGTAGACTGG
ACCCTTCATCAAGAGCACCATGGAGGAAGCTCACATCACGCCGGCGACGCCATCGCCATT
CTTCCCACTAGCAGGGCCTCACAAGTACATCGCGCTCCTCCTGGTTGTCCTCTCATGGAT
CCTGGTCCAGAGGTGGAGCCTGAGGAAGCAGAAAGGCCCGAGATCATGGCCAGTCATCGG
TGCAACGGTGGAGCAGCTGAGGAACTACCACCGGATGCACGACTGGCTTGTCGGGTACCT
GTCGCGGCACAGGACAGTGACCGTCGACATGCCGTTCACTTCCTACACCTACATCGCTGA
CCCGGTGAATGTCGAGCATGTCCTCAAGACTAACTTCACCAATTACCCCAAGGTAAATGA
CCTGAACTCACTGATGTTCAGTCTTCGGAAATCAGAGCTGAAAGCTGAATCGAATGTGCC
TGAACACCGTGTAGGGAATCGTGTACAGATCCTACATGGACGTGCTCCTCGGTGACGGCA
TCTTCAACGCCGACGGCGAGCTGTGGAGGAAGCAGAGGAAGACGGCGAGTTTCGAGTTCG
CCTCCAAGAACCTGAGGGATTTCAGCGCCATTGTGTTCAGAGAGTACTCCCTGAAGCTGT
CGGGTATACTGAGCCAGGCATCCAAGGCAGGCAAAGTTGTGGACATGCAGGTGAGATCAC
TGCTCCCTTGCCATTGCCAACATGAGCATTTCAACCTGAGACACGAGAGCTACCTTGCCG
ATTCAGGAACTTTACATGAGGATGACGCTGGACTCCATCTGCAAGGTTGGGTTCGGGGTC
GAGATCGGCACGCTGTCGCCGGATCTCCCCGAGAACAGCTTCGCGCAGGCGTTCGATGCC
GCCAACATCATCGTCACGCTGCGGTTCATCGACCCGCTGTGGCGCATCAAGAGGTTCTTC
CACGTCGGGTCAGAGGCCCTCCTAGCGCAGAGCATCAAGCTCGTGGACGAGTTCACCTAC
AGCGTGATCCGCCGGAGGAAGGCCGAGATCGTCGAGGTCCGGGCCAGCGGCAAACAGGAG
AAGGTACGTGTACATGACTGTTTCGATTCTTCAGTTCATCGTCTTGGCCGGGATGGACCT
GATCCTGATTGATTATATATCCGTGTGACTTGTGAGGACAAATTAAAATGGGCAGATGAA
GCACGACATCCTGTCACGGTTCATCGAGCTAGGCGAGGCCGGCGACGACGGCGGCGGCTT
CGGGGACGACAAGAGCCTCCGGGACGTGGTGCTCAACTTCGTGATCGCCGGGCGGGACAC
GACGGCGACGACGCTGTCGTGGTTCACGCACATGGCCATGTCCCACCCGGACGTGGCCGA
GAAGCTGCGCCGCGAGCTGTGCGCGTTCGAGGCGGAGCGCGCGCGCGAGGAGGGCGTCGC
GCTCGTGCCCTGCGGCGGCGCTGACGCCGACGACAAGGCGTTCGCCGCCCGCGTGGCGCA
GTTCGCGGGCCTCCTCACCTACGACAGCCTCGGCAAGCTGGTCTACCTCCACGCCTGCGT
CACCGAGACGCTCCGCCTGTACCCCGCCGTCCCTCAGGTGAGCGCGCCCGACACGACCTC
CGGTCCGCGATGCAACGCATATGTGGCTGTCCGCAGAGCACAGCATGCAGTGAGTGGACC
TGAATGCACTATGCAATGCACTTGCGCGCGCGCAGGACCCCAAGGGGATCCTGGAGGACG
ACGTGCTGCCGGACGGGACGAAGGTGAGGGCCGGCGGGATGGTGACGTACGTGCCCTACT
CGATGGGGCGGATGGAGTACAACTGGGGCCCCGACGCGGCGAGCTTCCGGCCGGAGCTAG
GGGTGAAAACGGGTAGGGTACCCGAAACGGGTACCGGATACGGATACTGATTCGGGACCA
TTTTCGGATACGGATACGGGTATTTTTTAGATTCGGGACGGATACGGGTAATACCCGGA
TAGTATGGCTTCGGATTCGGGTCGGATACGGAGCGAGTACTACCCGGTAAATACCCGGAT
ACTCGGGTCGGATACCGGGTACCCGGAATTCGGGTACCCGTTTTTCTTTTCTGCAAAA
TAATATAGTTATAAAATCATAACTTTACATATGAAATCGGATGAAGATAAAGTTTATAT
GAAAATTGTAGAGCTCGAAGAGATCTATAACTTTGTAGTACATCACATTTTTGTTTAAAC
ATATCTTAGGCCAAAATCATTAAAATAATGTCTAAATTTATATCAAAATAATAGACTTT
ATCATTTCATGTGGGACTTAAGATTATATCCATGTGGGAACTTAGGATTATCTTTTTA
TAAACTATTTATTAATATTGGTAACTTATTTGCAATTTTCGGTCGACGCTACAATATTTT
TATGAATTTAATTGTATTTTGATGATTTTCTACAACAAGAAATTAATAATACACCAAATA
GCCTAAAAAATTCATGGATTTTTACGGGACACAACATATATCCACATATAGTTCTCAAA
AACATTTGGACTATAAAATCCACAAGATGTTGGTGTTTCTTCCATTCTACTCCCACTTAT
TGCGTGAGTTACATGTGAAATCATTTTATGTATCGAAGTTTCAACATAATTAATATTTCA
```

Figure 16B

```
CTTATCATTTTCATGTGGCGACTTGAGGTTTTATTTGAATAGAATGTTTATTTGTTTTGG
TAAGCTTTTTGCATTTTGGATCAAACTAGTGTATTTATGAATTTTAATTATACTTTGATG
ATTTTATGTAGAAAGAAATTAATAATGTATAAATAGCCTCAGAAATCTATGAAATTATAC
GAAGGTACAACATATGGCCACATATAGTCATAACAAATAATGGGACCATAAAATCCACAG
GATGTCAACGTTTCTTCTATTTTATTTCCACTTATTGCGTGAGTTACACGTGAAATCACT
CTAAGTATCCAAGTTTCAACATAATCAATACTTCACTTTACCATTTTTACGTGGGAACTT
GAGATTATCTTCTATTAAATGCTTATTAGTATTAATTTACTTGCAATTTCGTGGTCGAAC
AAGAATATTTTTGATAACCAATTAATGCATTATCCGACAAGTATCCGATATCCGATCAA
ATAATATCCGTATCCGTCACTTATCCGCTCGGATAAATATCCGGTCCCTGTATCCGTATC
CGTCCCGTTTCTAACTATCCGTATCCGATCCCGAATCCGTTTTAAATACATTAGGGTAGG
ATACAGGATGAGCTAATATCCGTCCGTATCCGCCCGTTTTCACCCCTAGCCGGAGCGGTG
GATCAACGAGGATGGCGCGTTCCGCAACGCGTCGCCGTTCAAGTTCACGGCGTTCCAGGC
GGGGCCGAGGATCTGCCTGGGCAAGGACTCGGCGTACCTGCAGATGAAGATGGCGCTGGC
CATCCTTCTTGCGCTTCTACAGCTTCCGGCTGCTGGAGGGGCACCCGGTGCAGTACCGCA
TGATGACCATCCTCTCCATGGCGCACGGCCTCAAGGTCCGCGTCTCTAGGGCCGTCTGAT
GTCATGGCGATTTGGGATATCATCCCGCTTAATCCACGACAAATAACGTTCGTGTTACAA
ATTTGCATGCATGCATGTAAGGGAAAGCGATGGGTTTCATTGGTGGCTTGGCTTAAGCCT
TAAAAACTCCGTCGGGTTCTTGCGAACCACCACATCACTAGA
```

Ms26 Exon 5 Comparison

```
CDNA     QDPKGILEDDVLPDGTKVRAGGMVTYVPYSMGRMEYNWGPDAASFRPERW
Exon5-F  QDPKGILEDDVLPDGTKVRAGGMVTYVPYSMGRMEYNWGPDAASFRPERW
Exon5-S  QDPKGILEDDVLPDGTKVRAGGMVTYVPYSMGRMEYNWGPDAASFRPEAR Heme Binding Domain
CDNA     INEDGAFRNASPFKFTAFQAGPRICLGKDSAYLQMKMALAILFRFYSFRL
Exon5-F  INEDGAFRNASPFKFTAFQAGPRICLGKDSAYLQMKMALAILFRFYSFRL
Exon5-S  SGGSTRMARSATRRRSSSRRSRRGRGSAWARTRRTCR*RWRWPSSCASTA CDNA     LEGHPVQYRMMTILSMAHGLKVRVSRAV*CHGDLDMDIVPLNPRQITLVL
Exon5-F  LEGHPVQYRMMTILSMAHGLKVRVSRAV*CHGDLDMDIVPLNPRQITLVL
Exon5-S  SGCWRGTRCSTA**PSSPWRTKGEF CDNA     QICMHACKGKRWVSLVAWLKP*KLRRVLRTTTSLVFCTLLLSGSVVTAYK
Exon5-F  QICMHACKGKRWVSLVAWLKP*KLRRVLRTTTSLVF
```

Rice Ms26

>GRMT00000036836
ATGAAGAGCCCCATGGAGGAAGCTCATGCAATGCCAGTGACATCATTCTTCCCAGTAGCAGGAATCCACAAGCTCATAGCTATCTTCCTTGTCCTCTCATGGATCTTG
GTCCACAAGTGGAGCCTGAGGAACCAGAAGTGCCAAGATCATGCCCGACAGTGGAGCAACTCATGCAGGAACTACCACAGGATGCAACTGGCTTGTCGA
GTACTTGTCCAAGGACAGCGTCACCGTCGAAGTTCGTACAGTCTTCACTGTCTCCGTGATGCAAGTCCGAGATCGAGACCAATTCACCAATTA
CCCAAGGGTGAAGTTCTACAGTCTTCAACTGGTAGAGACTTCAGCACTGTGGCAATTCAATGCCAGATGTGGAGAACAAAGGAAGAACGGCGAGCTTCGAGT
TTGCCTCCAAGAACTTGAGGAGATGACACTCGGTTGACACTTGCTCCCTGAAGAAGCATTCTCCGAGAACAGCTTGCCAGGCATTC
AGGAATTGTTCATGAGGATGACATCGTCACCCTTCATGCAGCTGGCGAACGAGACCACAGAATGAGAAACCTCGAGTTCGAGTCGTT
GATGACTTCACTGTTCACTGTTCTGTGGCGGCGGCGATGGCAGCAGCCCAAGCAAGCAGAAGATCAACAACATACTGCCGGTTCATCGA
GCTGTCTGTCCCGAGCCGGCGGACGCTGTCACTGACATGGCAGGCGTCTTGCGGCCGGGCCCAGCTGTGCCCCCGCCCCGAGGAGCGCCC
CGTTGGCCCGACGCCGCGGCTCCGCCTCCGCTACTCGGAGGATGCAGTGCGTGCAAGTTCGCTGTGTGAGCAGTCGTGAGAAGTCTGCGGGCTGTCTCC
GACGAGGGATGGCCTACTCCAGGAGGATGCAGTAGAATCGGACCGGGCCCCTGCTGCGGCAAGATGAAGCGGGATCCGGAAGACGCGT
TACGCGTCCCTCAAGTTCGACGTTCACCGGGTTCCAGCCGGATGCCCGGGCAAGATGCCCGGCATCTCAGATGAAGATGCGGCTACCAG
CGCGCTTGAAGCTGTCGAGGACCACCCGGTCAAGGTCCAGCATCCTCCATGGATGATGACCGGATACCGGCCTCAAGGTCCGGTCCCCACCTCCGTCTGA

>GRMT00000036836 Rice Ms26 protein

MKSPMEEAHAMPVTSFFPVAGIHKLIAIFLVVLSWILVHKWSLRNQKGPRSWPIIGATVE QLKNYHRMHDWLVEYLSKDRTVTVDMPFTSYTYIADPVNVEHVLKTNFTNYPKGEVYRSY
MDVLLGDGIFNADGEMWRKQRKTASFEFASKNLRDFSTVFREYSLKLSILSQACKAGR VVDMQELFMRMTLDSICKVGFGVEIGTLSPDLPENSFAQAFDAANIIVTLRFIDPLWRLK
KFLHVGSEALLEQSMKLVDDFTYSVIRRRKAEILQARASGKQEKIKHDILSRFIELGEAG GDEGGSFGDDKSLRDVVLNFVIAGRDTTATTILSWFTYMAMTHPAVADKLRRELAAFEDE
RAREEGVALADAAGEASFAARVAQFASLLSYDAVGKLVYLHACVTETLRLYPAVPQDPKG
IVEDDVLPDGTKVRAGGMVTYVPYSMGRMEYNWGPDAASFRPERWLSGDGAFRNASPFK
FTAFQAGPRICLGKDSAYLQMKMALAILFRFYTFDLVEDHPVKYRMMTILSMAHGLKVRV STSV

Figure 19

Maize, rice and sorghum MS26 promoter alignment

```
                                     651                                                                          700
gi_14030555_gb_AF366296.1_AF366296 (650) AAGGAATGCTCAGTTTTTAAGGAACAATGTACAGATTTCATTTCAGAAC
        sorghum ms26 promoter      (114) AACGAATCTATCA---TTGTGCCTAAATTTTAAAGCAATTCT------GGAC
             riceMS26promoter        (1) AAGCCTGGTTTCAG---TTGGTGACAATTAACAGAATTCAGATG-GATA
                 Consensus         (651) AAGGAATGT TCAG TTTTG  GAAAATTTTACAGAATTCA  T  GAAC
                                     701                                                                          750
gi_14030555_gb_AF366296.1_AF366296 (700) TCTTTCTCGGTTGGTTGAGTTT-CAGACTTTTGTACCAAGCTGATGGATC
        sorghum ms26 promoter      (157) AATTTCTCGTAGGCTGAGTTT-CAGACTTTCACTACCAAGCTGATGGATC
             riceMS26promoter       (47) TGGTTCTGATATTAGAAGGTGGCATACCTTTAGTCGCT-GCAAACGCTTC
                 Consensus         (701) T TTTCTCGGTAGG TGAGTTT CAGACTTTTAGTACCAAGCTGATGGATC
                                     751                                                                          800
gi_14030555_gb_AF366296.1_AF366296 (749) ACAATACTTGTTTCCAAAGTCTGATAACAGAAACTGGCAACTCCTAATTG
        sorghum ms26 promoter      (206) ACATT---CTGGATCCGAAGTATGATAACATAATCTGGCAACTCCTAATTG
             riceMS26promoter       (96) AG-TTATCTGAA---CAAA------ACAAC-GAACTTGGCTGAGC--AGGGG
                 Consensus         (751) ACATTA CTG ATCCAAAGT TGATAACAGAA CTGGCAACTCCTAATTG
                                     801                                                                          850
gi_14030555_gb_AF366296.1_AF366296 (799) ATAATAAAAA-GAATAA-------AATACAGTATCAGA-TATC--TCATTT
        sorghum ms26 promoter      (254) -TAATAACAAATGAATAACCTGCAAATACATAATAAGAGTGGC--TCATTT
             riceMS26promoter      (135) AAAAAATACTGTAGCATTCATTTGTGTTTACATGAGTAACGATTCTTT
                 Consensus         (801) ATAATAA AATGAATAA      AATACAGTATAAGAGTA  C  TCATTT
                                     851                                                                          900
gi_14030555_gb_AF366296.1_AF366296 (839) TCTTGTTCTGCAGATCACAAAAAGGAACAACAAAGCTAAGCCTCCTACTT
        sorghum ms26 promoter      (301) TCTTGTTGGCAGATCACAAAAAGGAACAACAAAGCTAAGCG--CCAACTT
             riceMS26promoter      (185) TCTTAGGTGACAGATCACAAAAAG-AAAACTAAAGCTAAGAT-CCAACTC
                 Consensus         (851) TCTTGGTTGGCAGATCACAAAAAGGAACACAAAGCTAAGC  CCAACTT
                                     901                                                                          950
gi_14030555_gb_AF366296.1_AF366296 (889) GTTCGGGAGTTAGGTCAGGGACCACCATATGAATGAAAAGAAATCTTAATTT
        sorghum ms26 promoter      (350) GTCCGGAGTTAGGTCATGGATTACCATATGAATGAATGAAAGAAATCTTAATTT
             riceMS26promoter      (233) CTAAGGGTGTTAGGTTAGGGACCACCATATGAATGAATGAGACAA-TCTTAATTC
                 Consensus         (901) GT CGGGAGTTAGGTCAGGGACCACCATATGAATGAATGAAAGAAATCTTAATTT
                                     951                                                                         1000
gi_14030555_gb_AF366296.1_AF366296 (939) GGGGTCACACCAAGATTGTCTCTCTCGAGGTTGGGGGGTCCCTAAGGTTG
        sorghum ms26 promoter      (400) CCGGTCACACCAAGATTGTCTCTC--------------------AAGGTTG
             riceMS26promoter      (282) TTGGTCACACCAAAGATTGTCTC--------------------AAGGTTG
                 Consensus         (951) GGTCACACCAAGATTGTCTCTCTC                    AAGGTTG
                                    1001                                                                         1050
gi_14030555_gb_AF366296.1_AF366296 (989) GTAGTAGCAATACCCAATATATCACCTAACAAACCCAATCCATGCTACAT
        sorghum ms26 promoter      (433) GTAACAGCAATATCCCAATATATCACCTAACAAACCCAGACAACACTACAT
             riceMS26promoter      (311) GTAGCATCAGTGCCCAATATATCACCTAACTATGCCA-TCCAAAATGC-T
                 Consensus        (1001) GTAGCAGCAATACCCAATATATCACCTAACAAACCCA TCCA ACTACAT
                                    1051                                                                         1100
gi_14030555_gb_AF366296.1_AF366296 (1039) ACATACATAGCATCATCACTTGTAGACTGGACCCTTCATCAAGAGCACC
        sorghum ms26 promoter      (483) ACATA-----ACATCCATCACTTGGAGACTGGACCCTTCATCAAGAGCACC
             riceMS26promoter      (359) ACATA-----G---CATCTCTTGTAGACTGAACCCTTCATGAAGAGCCCC
                 Consensus        (1051) ACATA     CATCCATCACTTGTAGACTGGACCCTTCATCAAGAGCACC
                                    1101                                                                         1150
gi_14030555_gb_AF366296.1_AF366296 (1089) ATG-------------------------------------------
        sorghum ms26 promoter      (529) ATGGAGGAAGCTTCACCTCATG----------------------------
             riceMS26promoter      (401) ATGGAGGAAGCTCATGCAATGCCAGTGACATCATTCTTCCCAGTAGCAGG
                 Consensus        (1101) ATGGAGGAAGCTCA    ATG
```

Figure 20

```
                                             50
              MS26    (1)  --MEEAHLTPATPSPFFPLAGPHKYIALLLVVLSWIIVQRWSLRKQKGPR
         RICE-MS26    (1)  MKSPMEEAHAMPVTSFFPVAGIHKLIAIFLVVLSWIIVHKWSLRNQKGPR
sorghum contig-made-by-aligning-top7hits
                      (1)  -------MPATPLPFLAGLHKYIAILLVVLSWAIVHRWSLRKQKGPR
         Consensus    (1)           MP TPFFPLAGIHKYIAILLVVLSWIIVHRWSLRKQKGPR
                                                                    100
                            51
              MS26   (49)  SWPVIGATVEQLRNYHRMHDWLVGYLSRHRTVTVDMPFTSYTYIADPVNV
         RICE-MS26   (51)  SWPIIGATVEQLKNYHRMHDWLVEYLSKDRTVTVDMPFTSYTYIADPVNV
sorghum contig-made-by-aligning-top7hits
                     (41)  SWPVIGATLEQLRNYHRMHDWLVGYLSRHKTVTVDMPFTSYTYIADPVNV
         Consensus   (51)  SWPVIGATVEQLRNYHRMHDWLVGYLSRHRTVTVDMPFTSYTYIADPVNV
                            101                                      150
              MS26   (99)  EHVLKTNFTNYPKGIVRSYMDVLLGDGIFNADGELWRKQRKTASFEFAS
         RICE-MS26  (101)  EHVLKTNFTNYPKGEVYRSYMDVLLGDGIFNADGEMWRKQRKTASFEFAS
sorghum contig-made-by-aligning-top7hits
                     (91)  EHVLKTNFTNYPKGDVYRSIMDVLLGDGIFNADGELWRKQRKTASFEFAS
         Consensus  (101)  EHVLKTNFTNYPKGDVYRSYMDVLLGDGIFNADGELWRKQRKTASFEFAS
                            151                                      200
              MS26  (149)  KNLRDFSAIVFREYSLKLSGILSQASKAGKVVDMQELYMRMTLDSICKVG
         RICE-MS26  (151)  KNLRDFSTVVFREYSLKLSGILSQACKAGKVVDMQELFMRMTLDSICKVG
sorghum contig-made-by-aligning-top7hits
                    (141)  KNLRDFSANVFREYSLKLSGILSQASKAGKVVDMQELYMRMTLDSICKVG
         Consensus  (151)  KNLRDFSAIVFREYSLKLSGILSQASKAGKVVDMQELYMRMTLDSICKVG
                            201                                      250
              MS26  (199)  FGVEIGTLSPDLPENSFAQAFDAANIIITLRFIDPLWRIKRFFHVGSEAL
         RICE-MS26  (201)  FGVEIGTLSPDLPENSFAQAFDAANIIVTLRFIDPLWRLKKFLHVGSEAL
sorghum contig-made-by-aligning-top7hits
                    (191)  FGVEIGTLSPDLPENSFAQAFDAANIIVTLRFIDPLWRVKRFFHVGSEAL
         Consensus  (201)  FGVEIGTLSPDLPENSFAQAFDAANIIVTLRFIDPLWRIKRFFHVGSEAL
                            251                                      300
              MS26  (249)  LAQSIKLVDEFTYSVIRRRKAEIVEVRASGKQEKMKHDILSRFIELGEAG
         RICE-MS26  (251)  LEQSMKLVDDFTYSVIRRRKAEIIQARASGKQEKIKHDILSRFIELGEAG
sorghum contig-made-by-aligning-top7hits
                    (241)  LAQSIKLVDEFTYSVIRRRKAEIVEARASGKQEKMKHDILSRFIELGEAG
         Consensus  (251)  LAQSIKLVDEFTYSVIRRRKAEIVEARASGKQEKMKHDILSRFIELGEAG
                            301                                      350
              MS26  (299)  DDGGG---FGDDKSLRDVVLNFVIAGRDTTATTLSWFTHMAMSHPDVAEKL
         RICE-MS26  (301)  GDEGGSFGDDKSLRDVVLNFVIAGRDTTATTLSWFTYMAMTHPAVADKL
sorghum contig-made-by-aligning-top7hits
                    (291)  DDGF----GDDKSLRDVVLNFVIAGRDTTATTLSWFTHMAMSHPDVAEKL
         Consensus  (301)  DDGGG   FGDDKSLRDVVLNFVIAGRDTTATTLSWFTHMAMSHPDVAEKL
                            351                                      400
              MS26  (347)  RRELCAFEAERAREEGVTLVLCGGADADDKAFAARVAQFAGLLTYDSLGK
         RICE-MS26  (351)  RRELAAFEDERAREEGVALADAA----GRASFAARVAQFASLLSYDAVGK
sorghum contig-made-by-aligning-top7hits
                    (338)  RRELCAFEAERAREEGVAVPCCG---PDDKAFAARVAQFAGLLTYDSLGK
         Consensus  (351)  RRELCAFEAERAREEGVAL  CG   DDKAFAARVAQFAGLLTYDSLGK
                            401                                      450
              MS26  (397)  LVYLHACVTETLRLYPAVPQDPKGILEDDVLPDGTKVRAGGMVTYVPYSM
         RICE-MS26  (397)  LVYLHACVTETLRLYPAVPQDPKGIVEDDVLPDGTKVRAGGMVTYVPYSM
sorghum contig-made-by-aligning-top7hits
                    (386)  LVYLHACVTETLRLYPAVPQDPKGILEDDVLPDGTKVRAGGMVTYVPYSM
         Consensus  (401)  LVYLHACVTETLRLYPAVPQDPKGILEDDVLPDGTKVRAGGMVTYVPYSM
                            451                                      500
              MS26  (447)  GRMEYNWGPDAASFRPERWINEDG-AFRNASPFKFTAFQAGPRICLGKDS
         RICE-MS26  (447)  GRMEYNWGPDAASFRPERWLSGDGGAFRNASPFKFTAFQAGPRICLGKDS
sorghum contig-made-by-aligning-top7hits
                    (436)  GRMEYNWGPDAASFRPERWINEEG-AFRNASPFKFTAFQAGPRICLGKDS
         Consensus  (451)  GRMEYNWGPDAASFRPERWINEDG AFRNASPFKFTAFQAGPRICLGKDS
                            501                         548
              MS26  (496)  AYILQMKMALAILPFYSFRLLEGHPVQYRMMTILSMAHGLKVRSRAV
         RICE-MS26  (497)  AYILQMKMALAILPRFYTFDLVEDHPVKYRMMTILSMAHGLKVRVSTSV
sorghum contig-made-by-aligning-top7hits
                    (485)  AYILQMKMALAILPFPYSFQLLEGHPVQYRMMTILSMAHGLKVRVSRAV
         Consensus  (501)  AYILQMKMALAILPFPYSF LLEGHPVQYRMMTILSMAHGLKVRVSRAV
```

Figure 21

Maize, rice and sorghum MS26 alignment

Figure 24

```
   1 GGCACGAGCC GGCGAGCCCA CTCGGCAGTC GGCACAACCA CACACACTC CTGAGATAAG TGAAGCATCT CGGCACTGT CGCAGTCGCA
                                                         . . . . . . .
 101 GACGGAGATG ATGAAGCACT CGAGCAGCTT GTGCTTGCTC TTCCTCTTGG CGCTCTGCTG CACCCTGCTG GCCTGCGGCC TGGTCCAGGC ACAAGTCTC
      M  M  K  H  S  S  S  L  C  L  L  F  L  L  A  L  C  T  T  L  L  A  C  G  L  V  Q  A  Q  V  L
 201 TTCCAGGGGT TTAACTGGGA GTCTGCAAG CAGCAGGGAG GCTGGTACAA CAGGCTCAAG GCCCAGTCG ACGACATCGC CAAGGCCCGC GTCACGCACG
      F  Q  G  F  N  W  E  S  C  K  Q  Q  G  W  Y  N  R  L  K  A  Q  V  D  D  I  A  K  A  G  V  T  H  V
 301 TCTGGCTGCC TCCACCCTCG CACTCCGTCT CGGCACAAGG CTACATGCCA GGCCGCCTAT ACGACCTGGA CGCGTCCAAG TACGGCACGG CGGCGGAGCT
      . W  L  P  P  S  H  S  V  S  P  Q  G  Y  M  P  G  R  L  Y  D  L  D  A  S  K  Y  G  T  A  A  E  L
 401 CAAGTCCCTG ATAGCGGCGT TCCACGGCGG GGGCGTGCAG TGCGTGGCGG ACATCGTCAT CAACCACCGG TGCGCGGAAA AGAAGGACGC GCGCGGCGTG
      . K  S  L  I  A  A  F  H  G  R  G  V  Q  C  V  A  D  I  V  I  N  H  R  C  A  E  K  K  D  A  R  G  V
 501 TACTGCATCT TCGAGGGCGG GACTCCCGAC GACCGCCTGG ACTGGGGCCC CGGGATGATC TGCAGCGACG ACACGCAGTA CTCGGACGGG ACGGGGCACC
      Y  C  I  F  E  G  G  T  P  D  D  R  L  D  W  G  P  G  M  I  C  S  D  D  T  Q  Y  S  D  G  T  G  H  R
 601 GCGACACGGG CGAGGGGTTC GCGGGCGCGC CCGACATCGA CCACCTCAAC CCGGCGGTGC AGCGGGAGCT CTCCGCCTGG CTCAACTGGC TCAGGTCCGA
      . D  T  G  E  G  F  A  A  A  P  D  I  D  H  L  N  P  R  V  Q  R  E  L  S  A  W  L  N  W  L  R  S  D
 701 CGCCGTGGGG TTCGACGGCT GGCGCCTCGA CTTCGCCAAG GGCTACTCGC CGGCCTCGCC CAGAATGTAC GTGGAGAGCA CGGGGCCGCC GAGCTTCGTC
      . A  V  G  F  D  G  W  R  L  D  F  A  K  G  Y  S  P  A  V  A  R  M  Y  V  E  S  T  G  P  P  S  F  V
 801 GTCGCGGAGA TATGGAACTC GCTGAGCTAC AGCGGGGACG GCAAGCCCGC GCCCAACCAG GACCAGTGCC GGCAGGAGCT GCTGGACTGG ACGCGGGCCG
      V  A  E  I  W  N  S  L  S  Y  S  G  D  G  K  P  A  P  N  Q  D  Q  C  R  Q  E  L  L  D  W  T  R  A  V
 901 GGGGCCCGGCC CGCTGAGCCG TTCGACTTCC CCACCAAGGG CGCCGTCACC TTCGTCGACA ACCATGACAC CGGGTCGACG CAGAAGCTCT GGCCGTTCCC ATCCGACAAG
      . G  G  P  A  M  A  F  D  F  P  T  K  G  A  V  T  F  V  D  N  H  D  T  G  S  T  Q  K  L  W  P  F  P  S  D  K
1001 GCCCGGCCC ATCGGGTGGG CGCCCAGAA ATCCTCACC CATCCAGGAG TCCCCTGCAT TTTCTACGAC CACATGTTCG ACTGAACCT GAAGCAGGAG ATATCCACGC
      . A  G  L  I  G  W  A  P  E  K  A  Y  I  L  T  H  P  G  V  P  C  I  F  Y  D  H  M  F  D  W  N  L  K  Q  E  I  S  T  L
1101 GTCATGCAGG GCTACGCCTA CATCCTCACC CATCCAGGAG TCCCCTGCAT TTTCTACGAC CACATGTTCG ACTGGAACCT GAAGCAGGAG ATATCCACGC
      . S  A  I  R  A  R  N  G  I  R  A  G  S  K  L  R  I  L  V  A  D  A  D  A  Y  V  A  V  D  E  K  V
1201 TGTCTGCCAT CAGGGCGCGG AACGGCATCC GCGCCGGGAG CAAGCTGCGC ATCCTCGTGG CGGACGCGGA CGCGTACGTG GCCGTCGTCG ACGAGAAGGT
      . M  V  K  I  G  T  R  Y  G  V  S  S  V  V  P  S  D  F  H  P  A  A  H  G  K  D  Y  C  V  W  E  K  A
1301 CATGGTGAAG ATCGGGACAA GGTACGGCGT GAGCAGCGTG GTCCCGTCGG ATTTCCACCC GCCGGCGCAC GGCAAGGACT ACTGCGTCTG GGAGAAAGCG
      . S  L  R  V  P  A  G  R  H  L
1401 AGCTCCGCG TCCCGCGGG GCGCCACCTC TAGCAGCTCA GATTGCTCAG TCTTGTGCTG CATTGCAAAC ACAGAGCAC GACACTGCAT AACGTCTTTT
1501 CCTTAATTTC CTGAATTTTA CCTTTTCCTA GTTCAATTTC ATATATGTAT TTCTACATGT ACACACTATC ACAATCAGAT AAATAAACAA GCTTGGTCAA
1601 AAAAAAAAAA AAAAAAAA
```

NUCLEOTIDE SEQUENCES MEDIATING PLANT MALE FERTILITY AND METHOD OF USING SAME

REFERENCE TO RELATED APPLICATIONS

This application is a divisional application of previously filed and U.S. Ser. No. 11/471,202, filed Jun. 20, 2006, now U.S. Pat. No. 7,612,251, which is a continuation-in-part of U.S. Ser. No. 11/166,609 filed Jun. 24, 2005, now patented as U.S. Pat. No. 7,517,975, which is a continuation-in-part of U.S. Ser. No. 10/412,000 filed Apr. 11, 2003, now issued as U.S. Pat. No. 7,151,205, which is a continuation of previously filed application U.S. Ser. No. 09/670,153, now abandoned, filed Sep. 26, 2000, now abandoned, all of which are incorporated by reference in their entirety.

BACKGROUND OF THE INVENTION

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

In *Brassica*, the plant is normally self-sterile and can only be cross-pollinated. In self-pollinating species, such as soybeans and cotton, the male and female plants are anatomically juxtaposed. During natural pollination, the male reproductive organs of a given flower pollinate the female reproductive organs of the same flower.

Maize plants (*Zea mays* L.) present a unique situation in that they can be bred by both self-pollination and cross-pollination techniques. Maize has male flowers, located on the tassel, and female flowers, located on the ear, on the same plant. It can self or cross pollinate. Natural pollination occurs in maize when wind blows pollen from the tassels to the silks that protrude from the tops of the incipient ears.

A reliable method of controlling fertility in plants would offer the opportunity for improved plant breeding. This is especially true for development of maize hybrids, which relies upon some sort of male sterility system and where a female sterility system would reduce production costs.

The development of maize hybrids requires the development of homozygous inbred lines, the crossing of these lines, and the evaluation of the crosses. Pedigree breeding and recurrent selection are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid ($F_1$) and will form hybrid plants.

Environmental variation in plant development can result in plants tasseling after manual detasseling of the female parent is completed. Or, a detasseler might not completely remove the tassel of a female inbred plant. In any event, the result is that the female plant will successfully shed pollen and some female plants will be self-pollinated. This will result in seed of the female inbred being harvested along with the hybrid seed which is normally produced. Female inbred seed is not as productive as $F_1$ seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

A reliable system of genetic male sterility would provide advantages. The laborious detasseling process can be avoided in some genotypes by using cytoplasmic male-sterile (CMS) inbreds. In the absence of a fertility restorer gene, plants of a CMS inbred are male sterile as a result of factors resulting from the cytoplasmic, as opposed to the nuclear, genome. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS produced seed of the same hybrid must be blended to insure that adequate pollen loads are available for fertilization when the hybrid plants are grown and to insure cytoplasmic diversity.

There can be other drawbacks to CMS. One is an historically observed association of a specific variant of CMS with susceptibility to certain crop diseases. This problem has discouraged widespread use of that CMS variant in producing hybrid maize and has had a negative impact on the use of CMS in maize in general.

One type of genetic sterility is disclosed in U.S. Pat. Nos. 4,654,465 and 4,727,219 to Brar, et al. However, this form of genetic male sterility requires maintenance of multiple mutant genes at separate locations within the genome and requires a complex marker system to track the genes and make use of the system convenient. Patterson also described a genic system of chromosomal translocations which can be effective, but which are complicated. (See, U.S. Pat. Nos. 3,861,709 and 3,710,511.)

Many other attempts have been made to improve on these drawbacks. For example, Fabijanski, et al., developed several methods of causing male sterility in plants (see EPO 89/3010153.8 publication no. 329,308 and PCT application PCT/CA90/00037 published as WO 90/08828). One method includes delivering into the plant a gene encoding a cytotoxic substance associated with a male tissue specific promoter. Another involves an antisense system in which a gene critical to fertility is identified and an antisense to the gene inserted in the plant. Mariani, et al. also shows several cytotoxic antisense systems. See EP 89/401, 194. Still other systems use "repressor" genes which inhibit the expression of another gene critical to male sterility. PCT/GB90/00102, published as WO 90/08829.

A still further improvement of this system is one described at U.S. Pat. No. 5,478,369 in which a method of imparting controllable male sterility is achieved by silencing a gene native to the plant that is critical for male fertility and replacing the native DNA with the gene critical to male fertility linked to an inducible promoter controlling expression of the gene. The plant is thus constitutively sterile, becoming fertile only when the promoter is induced and its attached male fertility gene is expressed.

In a number of circumstances, a male sterility plant trait is expressed by maintenance of a homozygous recessive condition. Difficulties arise in maintaining the homozygous condition, when a transgenic restoration gene must be used for maintenance. For example, a natural mutation in a gene critical to male sterility can impart a male sterility phenotype to plants when this mutant allele is in the homozygous state. This sterility can be restored when the non-mutant form of the gene is introduced into the plant. However, this form of restoration removes the desired homozygous recessive condition, restores full male fertility and prevents maintenance of pure male sterile maternal lines. This issue can be avoided where production of pollen containing the restoration gene is eliminated, thus providing a maintainer plant producing only pollen not containing the restoration gene, and the progeny retains the homozygous condition. An example of one approach is shown in Dellaporta et al., U.S. Pat. No. 6,743,968, in which a plant is produced having a hemizygotic construct comprising a gene that produces a product fatal to a cell, linked with a pollen-specific promoter, and the restoration gene. When crossed with the homozygous recessive male sterile plant, the progeny thus retains the homozygous recessive condition.

As noted, an essential aspect of much of the work underway with male sterility systems is the identification of genes impacting male fertility.

Such a gene can be used in a variety of systems to control male fertility including those described herein. Previously, a male fertility gene has been identified in *Arabidopsis thaliana* and used to produce a male sterile plant. Aarts, et al., "Transposon Tagging of a Male Sterility Gene in *Arabidopsis*", *Nature*, 363:715-717 (Jun. 24, 1993). U.S. Pat. No. 5,478,369 discloses therein one such gene impacting male fertility. In the present invention the inventors provide novel DNA molecules and the amino acid sequence encoded that are critical to male fertility in plants. These can be used in any of the systems where control of fertility is useful, including those described above.

Thus, one object of the invention is to provide a nucleic acid sequence, the expression of which is critical to male fertility in plants.

Another object of the invention is to provide a DNA molecule encoding an amino acid sequence, the expression of which is critical to male fertility in plants.

Yet another object of the invention is to provide a promoter of such nucleotide sequence and its essential sequences.

A further object of the invention is to provide a method of using such DNA molecules to mediate male fertility in plants.

Further objects of the invention will become apparent in the description and claims that follow.

SUMMARY OF THE INVENTION

This invention relates to nucleic acid sequences, and, specifically, DNA molecules and the amino acid encoded by the DNA molecules, which are critical to male fertility. A promoter of the DNA is identified, as well as its essential sequences. It also relates to use of such DNA molecules to mediate fertility in plants.

BRIEF DESCRIPTION OF THE DRAWINGS

FIG. 4A-4D is the sequence of Ms26 (The cDNA is SEQ ID NO: 1, the protein is SEQ ID NOS: 2 and 34)

FIG. 5A-5C is the genomic Ms26 sequence (also referred to as SEQ ID NO: 7).

FIG. 6A-6D is a comparison of the genomic Ms26 sequence (Residues 1051-1450, 1501-2100 and 2201-3326 of SEQ ID NO: 7) with the cDNA of Ms26 (SEQ ID NO: 1).

FIG. 8 is the full length promoter of Ms26 (SEQ ID NO: 5)

FIG. 10 shows essential regions of the Ms26 promoter (SEQ ID NO: 6).

FIGS. 12A and 12B is a comparison of the nucleotide sequence (SEQ ID NO: 3) from the Ms26 orthologue from a *sorghum* panicle and Ms26 maize cDNA (Residues 201-750 of SEQ ID NO: 1), and the *sorghum* protein sequence (SEQ ID NO: 4) and Ms26 maize protein (Residues 87-244 of SEQ ID NO: 2).

FIG. 14 shows a sequence comparison of the region of excision of the ms26-ref allele (SEQ ID NO: 8) with wild-type Ms26 (SEQ ID NO: 9).

FIG. 15 shows the transposon sequence within ms26-ref (SEQ ID NO: 10).

FIG. 16 shows the entire ms26-ref sequence (SEQ ID NO: 11).

FIG. 17A shows a translated protein sequence alignment between regions of the CYP704B1, a P450 gene (SEQ ID NO: 12) and Ms26 (SEQ ID NO: 13); FIG. 17B shows the phylogenetic tree analysis of select P450 genes.

FIG. 18 demonstrates the heme binding domain frame shift, showing the translated sequence alignment of regions of the Ms26 cDNA (SEQ ID NOS: 14 and 28-29), the genomic regions of exon 5 in fertile plants (SEQ ID NOS: 15 and 30-31) and sterile plants (SEQ ID NOS: 16 and 32-33).

FIG. 19 shows the rice Ms26 cDNA (SEQ ID NO: 17) and protein (SEQ ID NO: 18).

FIG. 20 shows alignment of the Ms26 promoter of corn (Residues 650-1091 of SEQ ID NO: 5), sorghum SEQ ID NO: 19) and rice (SEQ ID NO: 20).

FIG. 21 shows alignment of the maize Ms26 protein (SEQ ID NO: 21); rice Ms26 protein (SEQ ID NO: 18) and sorghum Ms26 protein (SEQ ID NO: 22) along with a consensus sequence.

FIG. 24 shows a sequence of the Zea mays α-amylase 1 coding region (SEQ ID NOS: 26 (DNA) and 36 (protein)).

DISCLOSURE OF THE INVENTION

Figure 1:
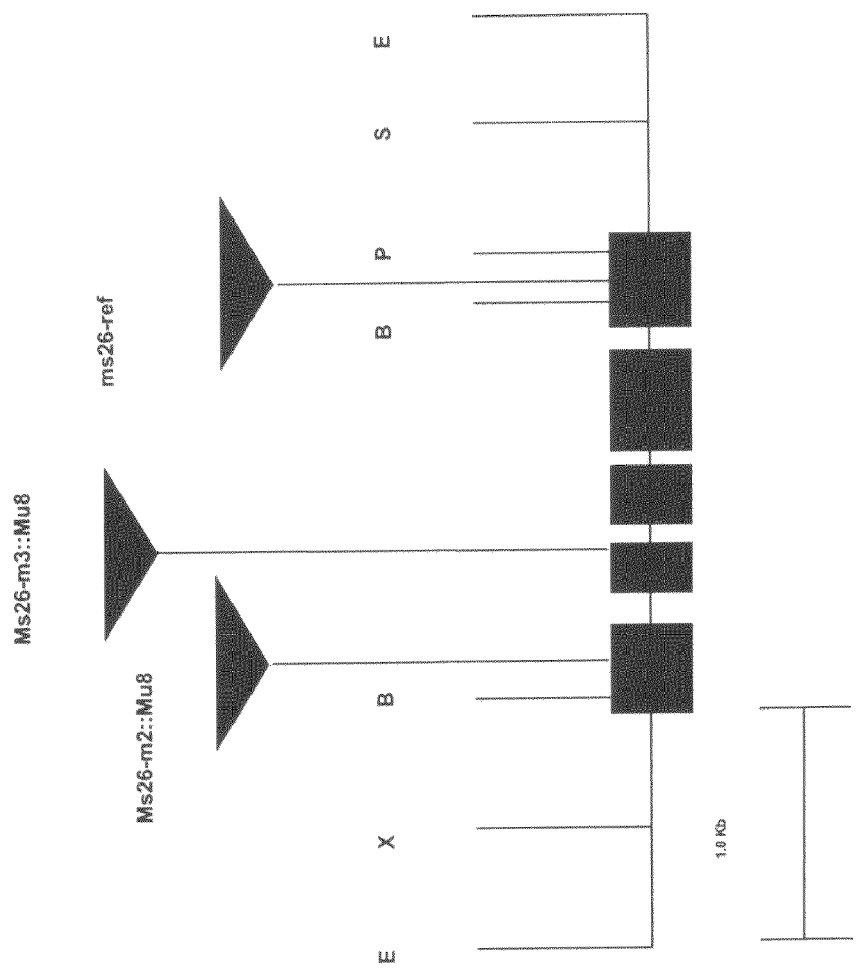
FIG. 1 is a locus map of the male fertility gene Ms26.

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated therein are standard methodologies well known to one of ordinary skill in the art. The materials, methods and examples are illustrative only and not limiting.

Genetic male sterility results from a mutation, suppression, or other impact to one of the genes critical to a specific step in microsporogenesis, the term applied to the entire process of pollen formulation. These genes can be collectively referred to as male fertility genes (or, alternatively, male sterility genes). There are many steps in the overall pathway where gene function impacts fertility. This seems aptly supported by the frequency of genetic male sterility in maize. New alleles of male sterility mutants are uncovered in materials that range from elite inbreds to unadapted populations.

At U.S. Pat. No. 5,478,369 there is described a method by which the Ms45 male sterility gene was tagged and cloned on maize chromosome 9. Previously, there had been described a male sterility gene on chromosome 9, ms2, which had never been cloned and sequenced. It is not allelic to the gene referred to in the '369 patent. See Albertsen, M. and Phillips, R. L., "Developmental Cytology of 13 Genetic Male Sterile Loci in Maize" *Canadian Journal of Genetics & Cytology* 23:195-208 (January 1981). The only fertility gene cloned before that had been the *Arabadopsis* gene described at Aarts, et al., supra.

Examples of genes that have been discovered subsequently that are critical to male fertility are numerous and include the *Arabidopsis* ABORTED MICROSPORES (AMS) gene, Sorensen et al., *The Plant Journal* (2003) 33(2):413-423); the *Arabidopsis* MS1 gene (Wilson et al., *The Plant Journal* (2001) 39(2):170-181); the NEF1 gene (Ariizumi et al., *The Plant Journal* (2004) 39(2):170-181); *Arabidopsis* AtGPAT1 gene (Zheng et al., *The Plant Cell* (2003) 15:1872-1887); the *Arabdiopsis* dde2-2 mutation was shown to be defective in the allene oxide syntase gene (Malek et al., *Planta* (2002) 216: 187-192); the *Arabidopsis* faceless pollen-1 gene (flp1) (Ariizumi et al, Plant Mol. Biol. (2003) 53:107-116); the *Arabidopsis* MALE MEIOCYTE DEATH1 gene (Yang et al., *The Plant Cell* (2003) 15: 1281-1295); the tapetum-specific zinc finger gene, TAZ1 (Kapoor et al., *The Plant Cell* (2002) 14:2353-2367); and the TAPETUM DETERMINANT1 gene (Lan et al, *The Plant Cell* (2003) 15:2792-2804).

The table below lists a number of known male fertility mutants or genes from *Zea mays*.

| GENE NAME | ALTERNATE NAME | REFERENCE |
| --- | --- | --- |
| ms1 male sterile1 | male sterile1, ms1 | Singleton, W R and Jones, D F. 1930. J Hered 21: 266-268 |
| ms10 male sterile10 | male sterile10, ms10 | Beadle, G W. 1932. Genetics 17: 413-431 |
| ms11 male sterile11 | ms11, male sterile11 | Beadle, G W. 1932. Genetics 17: 413-431 |
| ms12 male sterile12 | ms12, male sterile12 | Beadle, G W. 1932. Genetics 17: 413-431 |
| ms13 male sterile13 | ms*-6060, male sterile13, ms13 | Beadle, G W. 1932. Genetics 17: 413-431 |
| ms14 male sterile14 | ms14, male sterile14 | Beadle, G W. 1932. Genetics 17: 413-431 |
| ms17 male sterile17 | ms17, male sterile17 | Emerson, R A. 1932. Science 75: 566 |
| ms2 male sterile2 | male sterile2, ms2 | Eyster, W H. 1931. J Hered 22: 99-102 |
| ms20 male sterile20 | ms20, male sterile20 | Eyster, W H. 1934. Genetics of *Zea mays*. Bibliographia Genetica 11: 187-392 |
| ms23 male sterile23 | : ms*-6059, ms*-6031, ms*-6027, ms*-6018, ms*-6011, ms35, male sterile23, ms*-Bear7, ms23 | West, D P and Albertsen, M C. 1985. MNL 59: 87 |
| ms24 male sterile24 | ms24, male sterile24 | West, D P and Albertsen, M C. 1985. MNL 59: 87 |
| ms25 male sterile25 | ms*-6065, ms*-6057, ms25, male sterile25, ms*-6022 | Loukides, C A; Broadwater, A H; Bedinger, P A. 1995. Am J Bot 82: 1017-1023 |
| ms27 male sterile27 | ms27, male sterile27 | Albertsen, M C. 1996. MNL 70: 30-31 |
| ms28 male sterile28 | ms28, male sterile28 | Golubovskaya, I N. 1979. MNL 53: 66-70 |

-continued

| GENE NAME | ALTERNATE NAME | REFERENCE |
|---|---|---|
| ms29 male sterile29 | male sterile29, ms*-JH84A, ms29 | Trimnell, M R et al. 1998. MNL 72: 37-38 |
| ms3 male sterile3 | Group 3, ms3, male sterile3 | Eyster, W H. 1931. J Hered 22: 99-102 |
| ms30 male sterile30 | ms30, msx, ms*-6028, ms*-LI89, male sterile30, ms*-LI89 | Albertsen, M C et al. 1999. MNL 73: 48 |
| ms31 male sterile31 | ms*-CG889D, ms31, male sterile31 | Trimnell, M R et al. 1998. MNL 72: 38 |
| ms32 male sterile32 | male sterile32, ms32 | Trimnell, M R et al. 1999. MNL 73: 48-49 |
| ms33 male sterile33 | : ms*-6054, ms*-6024, ms33, ms*-GC89A, ms*-6029, male sterile6019, Group 7, ms*-6038, ms*-Stan1, ms*-6041, ms*-6019, male sterile33 | Patterson, E B. 1995. MNL 69: 126-128 |
| ms34 male sterile34 | Group 1, ms*-6014, ms*-6010, male sterile34, ms34, ms*-6013, ms*-6004, male sterile6004 | Patterson, E B. 1995. MNL 69: 126-128 |
| ms36 male sterile36 | male sterile36, ms*-MS85A, ms36 | Trimnell, M R et al. 1999. MNL 73: 49-50 |
| ms37 male sterile 37 | ms*-SB177, ms37, male sterile 37 | Trimnell, M R et al. 1999. MNL 73: 48 |
| ms38 male sterile38 | ms30, ms38, ms*-WL87A, male sterile38 | Albertsen, M C et al. 1996. MNL 70: 30 |
| ms43 male sterile43 | ms43, male sterile43, ms29 | Golubovskaya, I N. 1979. Int Rev Cytol 58: 247-290 |
| ms45 male sterile45 | Group 6, male sterile45, ms*-6006, ms*-6040, ms*-BS1, ms*-BS2, ms*-BS3, ms45, ms45'-9301 | Albertsen, M C; Fox, T W; Trimnell, M R. 1993. Proc Annu Corn Sorghum Ind Res Conf 48: 224-233 |
| ms48 male sterile48 | male sterile48, ms*-6049, ms48 | Trimnell, M et al. 2002. MNL 76: 38 |
| ms5 male sterile5 | : ms*-6061, ms*-6048, ms*-6062, male sterile5, ms5 | Beadle, G W. 1932. Genetics 17: 413-431 |
| ms50 male sterile50 | ms50, male sterile50, ms*-6055, ms*-6026 | Trimnell, M et al. 2002. MNL 76: 39 |
| ms7 male sterile7 | ms7, male sterile7 | Beadle, G W. 1932. Genetics 17: 413-431 |
| ms8 male sterile8 | male sterile8, ms8 | Beadle, G W. 1932. Genetics 17: 413-431 |
| ms9 male sterile9 | Group 5, male sterile9, ms9 | Beadle, G W. 1932. Genetics 17: 413-431 |
| ms49 male sterile49 | ms*-MB92, ms49, male sterile49 | Trimnell, M et al. 2002. MNL 76: 38-39 |

Thus the invention includes using the sequences shown herein to impact male fertility in a plant, that is, to control male fertility by manipulation of the genome using the genes of the invention. By way of example, without limitation, any of the methods described infra can be used with the sequence of the invention such as introducing a mutant sequence into a plant to cause sterility, causing mutation to the native sequence, introducing an antisense of the sequence into the plant, use of hairpin formations, linking it with other sequences to control its expression, or any one of a myriad of processes available to one skilled in the art to impact male fertility in a plant.

The Ms26 gene described herein is located on maize chromosome 1 and its dominant allele is critical to male fertility. The locus map is represented at FIG. 1. It can be used in the systems described above, and other systems impacting male fertility.

Figure 2:
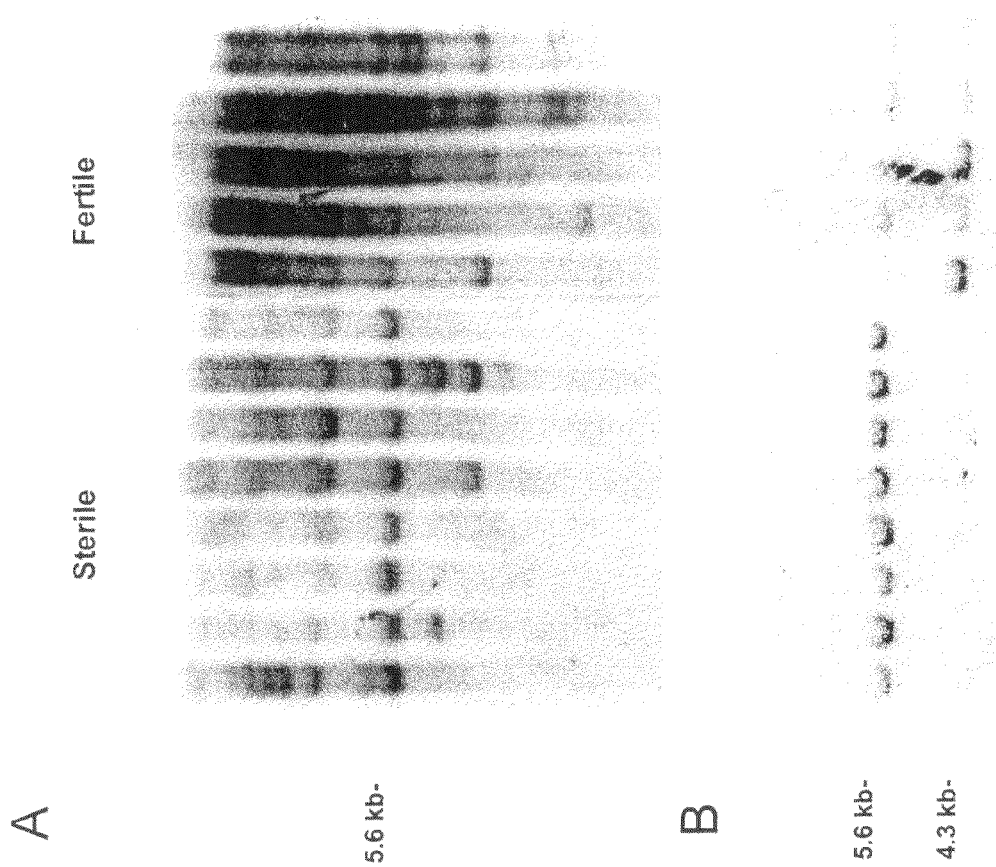
FIG. 2A is a Southern blot of the ms26-m2::Mu8 family hybridized with a Mu8 probe.
FIG. 2B is a Southern blot of the ms26-m2::Mu8 family hybridized with a PstI fragment isolated from the ms26 clone.

The maize family cosegregating for sterility was named ms*-SBMu200 and was found to have an approximately 5.5 Kb EcoRI fragment that hybridized with a Mu8 probe (FIG. 2A). A genomic clone from the family was isolated which contained a Mu8 transposon. A probe made from DNA bordering the transposon was found to hybridize to the same ~5.5 Kb EcoR1 fragment (FIG. 2B). This probe was used to isolate cDNA clones from a tassel cDNA library. The cDNA is 1906 bp, and the Mu insertion occurred in exon 1 of the gene. This probe was also used to map the mutation in an RFLP mapping population. The mutant mapped to the short arm of chromosome 1, near Ms26. Allelism crosses between ms26-ref and ms*-SBMu200 showed that these were allelic, indicating that the mutations occurred in the same gene. The ms*-SBMu200 allele was renamed ms26-m2::Mu8. Two additional alleles for the Ms26 gene were cloned, one containing a Mutator element in the second exon, named ms26-m3::Mu*, and one containing an unknown transposon in the fifth exon from the ms26-ref allele. FIG. 5 (discussed further below) represents the genomic nucleotide sequence. Expression patterns, as determined by Northern analysis, show tassel specificity with peak expression at about the quartet to quartet release stages of microsporogenesis.

It will be evident to one skilled in the art that variations, mutations, derivations including fragments smaller than the entire sequence set forth may be used which retain the male sterility controlling properties of the gene. One of ordinary skill in the art can readily assess the variant or fragment by introduction into plants homozygous for a stable male sterile allele of Ms26, followed by observation of the plant's male tissue development.

The sequences of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa, rice, cotton and *sorghum*.

Sequences from other plants may be isolated according to well-known techniques based on their sequence homology to the homologous coding region of the coding sequences set forth herein. In these techniques, all or part of the known coding sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

Thus the invention also includes those nucleotide sequences which selectively hybridize to the Ms26 nucleotide sequences under stringent conditions. In referring to a sequence that "selectively hybridizes" with Ms26, the term includes reference to hybridization, under stringent hybridization conditions, of a nucleic acid sequence to the specified nucleic acid target sequence to a detectably greater degree than its hybridization to non-target nucleic acid.

The terms "stringent conditions" or "stringent hybridization conditions" includes reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Generally, probes of this type are in a range of about 1000 nucleotides in length to about 250 nucleotides in length.

An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). See also Sambrook et al. (1989) *Molecular Cloning: A Laboratory Manual* (2nd ed. Cold Spring Harbor Laboratory, Cold Spring Harbor, N.Y.).

In general, sequences that correspond to the nucleotide sequences of the present invention and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

Preferred hybridization conditions for the nucleotide sequence of the invention include hybridization at 42° C. in 50% (w/v) formamide, 6×SSC, 0.5% (w/v) SDS, 100 (g/ml salmon sperm DNA. Exemplary low stringency washing conditions include hybridization at 42° C. in a solution of 2×SSC, 0.5% (w/v) SDS for 30 minutes and repeating. Exemplary moderate stringency conditions include a wash in 2×SSC, 0.5% (w/v) SDS at 50° C. for 30 minutes and repeating. Exemplary high stringency conditions include a wash in 0.1× SSC, 0.1% (w/v) SDS, at 65° C. for 30 minutes to one hour and repeating. Sequences that correspond to the promoter of the present invention may be obtained using all the above conditions. For purposes of defining the invention, the high stringency conditions are used.

The following terms are used to describe the sequence relationships between two or more nucleic acids or polynucleotides: (a) "reference sequence", (b) "comparison window", (c) "sequence identity", and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, or 100 nucleotides in length, or longer. Those of skill in the art understand that to avoid a high similarity to a reference sequence due to inclusion of gaps in the polynucleotide sequence a gap penalty is typically introduced and is subtracted from the number of matches.

Methods of aligning sequences for comparison are well-known in the art. Thus, the determination of percent sequence identity between any two sequences can be accomplished using a mathematical algorithm. Non-limiting examples of such mathematical algorithms are the algorithm of Myers and Miller (1988) *CABIOS* 4: 11-17; the local alignment algorithm of Smith et al. (1981) *Adv. Appl. Math.* 2: 482; the global alignment algorithm of Needleman and Wunsch (1970) *J. Mol. Biol.* 48: 443-453; the search-for-local-alignment-method of Pearson and Lipman (1988) *Proc. Natl. Acad. Sci.* 85: 2444-2448; the algorithm of Karlin and Altschul (1990) *Proc. Natl. Acad. Sci. USA* 87: 2264, modified as in Karlin and Altschul (1993) *Proc. Natl. Acad. Sci. USA* 90: 5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73: 237-244 (1988); Higgins et al. (1989) *CABIOS* 5: 151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215: 403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25: 3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2; and the BLOSUM62 scoring matrix or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

Promoter regions can be readily identified by one skilled in the art. The putative start codon containing the ATG motif is identified and upstream from the start codon is the presumptive promoter. By "promoter" is intended a regulatory region of DNA usually comprising a TATA box capable of directing RNA polymerase II to initiate RNA synthesis at the appropriate transcription initiation site for a particular coding sequence. A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the region upstream of the TATA box from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as male tissue can be identified, isolated, and used with other core promoters to confirm male tissue-preferred expression. By core promoter is meant the minimal sequence required to initiate transcription, such as the sequence called the TATA box which is common to promoters in genes encoding proteins. Thus the upstream promoter of Ms26 can optionally be used in conjunction with its own or core promoters from other sources. The promoter may be native or non-native to the cell in which it is found.

The isolated promoter sequence of the present invention can be modified to provide for a range of expression levels of the heterologous nucleotide sequence. Less than the entire promoter region can be utilized and the ability to drive anther-preferred expression retained. However, it is recognized that expression levels of mRNA can be decreased with deletions of portions of the promoter sequence. Thus, the promoter can be modified to be a weak or strong promoter. Generally, by "weak promoter" is intended a promoter that drives expression of a coding sequence at a low level. By "low level" is intended levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts. Generally, at least about 30 nucleotides of an isolated promoter sequence will be used to drive expression of a nucleotide sequence. It is recognized that to increase transcription levels, enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region of 5' untranslation region (5'UTR). Likewise the terminator can be isolated from the 3' region flanking its respective stop codon. The term "isolated" refers to material such as a nucleic acid or protein which is substantially or essentially free from components which normally accompany or interact with the material as found in it naturally occurring environment or if the material is in its natural environment, the material has been altered by deliberate human intervention to a composition and/or placed at a locus in a cell other than the locus native to the material. Methods for isolation of promoter regions are well known in the art.

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" of the regulatory sequence is a nucleotide sequence that is a regulatory sequence variant formed by one or more deletions from a larger sequence. For example, the 5' portion of a promoter up to the TATA box near the transcription start site can be deleted without abolishing promoter activity, as described by Opsahl-Sorteberg, H-G. et al., "Identification of a 49-bp fragment of the HvLTP2 promoter directing aleruone cell specific expression" *Gene* 341:49-58 (2004). Such variants should retain promoter activity, particularly the ability to drive expression in male tissues. Activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) *Methods Enzymol.* 155:335-350, and Erlich, ed. (1989) *PCR Technology* (Stockton Press, New York).

Sequences which hybridize to the regulatory sequences of the present invention are within the scope of the invention. Sequences that correspond to the promoter sequences of the present invention and hybridize to the promoter sequences disclosed herein will be at least 50% homologous, 70% homologous, and even 85% 86%, 87%, 88%, 89%, 90%, 91%, 92%, 93%, 94%, 95%, 96%, 97%, 98%, 99% homologous or more with the disclosed sequence.

Smaller fragments may yet contain the regulatory properties of the promoter so identified and deletion analysis is one method of identifying essential regions. Deletion analysis can occur from both the 5' and 3' ends of the regulatory region. Fragments can be obtained by site-directed mutagenesis, mutagenesis using the polymerase chain reaction and the like. (See, *Directed Mutagenesis: A Practical Approach* IRL Press (1991)). The 3' deletions can delineate the essential region and identify the 3' end so that this region may then be operably linked to a core promoter of choice. Once the essential region is identified, transcription of an exogenous gene may be controlled by the essential region plus a core promoter. By core promoter is meant the sequence called the TATA box which is common to promoters in all genes encoding proteins. Thus the upstream promoter of Ms26 can optionally be used in conjunction with its own or core promoters from other sources. The promoter may be native or non-native to the cell in which it is found.

The core promoter can be any one of known core promoters such as the Cauliflower Mosaic Virus 35S or 19S promoter (U.S. Pat. No. 5,352,605), ubiquitin promoter (U.S. Pat. No. 5,510,474) the IN2 core promoter (U.S. Pat. No. 5,364,780) or a Figwort Mosaic Virus promoter (Gruber, et al. "Vectors for Plant Transformation" *Methods in Plant Molecular Biology and Biotechnology*) et al. eds, CRC Press pp. 89-119 (1993)).

The regulatory region of Ms26 has been identified as including the 1005 bp region upstream of the putative TATA box. See FIG. 8. Further, using the procedures outlined above, it has been determined that an essential region of the promoter includes the −180 bp upstream of the TATA box and specifically, the −176 to −44 region is particularly essential.

Promoter sequences from other plants may be isolated according to well-known techniques based on their sequence homology to the promoter sequence set forth herein. In these techniques, all or part of the known promoter sequence is used as a probe which selectively hybridizes to other sequences present in a population of cloned genomic DNA fragments (i.e. genomic libraries) from a chosen organism. Methods are readily available in the art for the hybridization of nucleic acid sequences.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al., eds., (1990) *PCR Protocols, A Guide to Methods and Applications*, Academic Press).

Further, a promoter of the present invention can be linked with nucleotide sequences other than the Ms26 gene to express other heterologous nucleotide sequences. The nucleotide sequence for the promoter of the invention, as well as fragments and variants thereof, can be provided in expression cassettes along with heterologous nucleotide sequences for expression in the plant of interest, more particularly in the male tissue of the plant. Such an expression cassette is provided with a plurality of restriction sites for insertion of the nucleotide sequence to be under the transcriptional regulation of the promoter. These expression cassettes are useful in the genetic manipulation of any plant to achieve a desired phenotypic response.

Examples of other nucleotide sequences which can be used as the exogenous gene of the expression vector with the Ms26 promoter, or other promoters taught herein or known to those of skill in the art, or other promoters taught herein or known to those of skill in the art complementary nucleotidic units such as antisense molecules (callase antisense RNA, barnase antisense RNA and chalcone synthase antisense RNA, Ms45 antisense RNA), ribozymes and external guide sequences, an aptamer or single stranded nucleotides. The exogenous nucleotide sequence can also encode carbohydrate degrading or modifying enzymes, amylases, debranching enzymes and pectinases, such as the alpha amylase gene of FIG. 24, auxins, rol B, cytotoxins, diptheria toxin, DAM methylase, avidin, or may be selected from a prokaryotic regulatory system. By way of example, Mariani, et al., *Nature* Vol. 347; pp. 737; (1990), have shown that expression in the tapetum of either *Aspergillus oryzae* RNase-T1 or an RNase of *Bacillus amyloliquefaciens*, designated "barnase," induced destruction of the tapetal cells, resulting in male infertility. Quaas, et al., *Eur. J. Biochem.* Vol. 173: pp. 617 (1988), describe the chemical synthesis of the RNase-T1, while the nucleotide sequence of the barnase gene is disclosed in Hartley, *J. Molec. Biol.*; Vol. 202: pp. 913 (1988). The rolB gene of *Agrobacterium rhizogenes* codes for an enzyme that interferes with auxin metabolism by catalyzing the release of free indoles from indoxyl-β-glucosides. Estruch, et al., *EMBO J.* Vol. 11: pp. 3125 (1991) and Spena, et al., *Theor. Appl. Genet.*; Vol. 84: pp. 520 (1992), have shown that the anther-specific expression of the rolB gene in tobacco resulted in plants having shriveled anthers in which pollen production was severely decreased and the rolB gene is an example of a gene that is useful for the control of pollen production. Slightom, et al., *J. Biol. Chem.* Vol. 261: pp. 108 (1985), disclose the nucleotide sequence of the rolB gene. DNA molecules encoding the diphtheria toxin gene can be obtained from the American Type Culture Collection (Rockville, Md.), ATCC No. 39359 or ATCC No. 67011 and see Fabijanski, et al., E.P. Appl. No. 90902754.2, "Molecular Methods of Hybrid Seed Production" for examples and methods of use. The DAM methylase gene is used to cause sterility in the methods discussed at U.S. Pat. No. 5,689,049 and PCT/US95/15229 Cigan, A. M. and Albertsen, M. C., "Reversible Nuclear Genetic System for Male Sterility in Transgenic Plants." Also see discussion of use of the avidin gene to cause sterility at U.S. Pat. No. 5,962,769 "Induction of Male Sterility in Plants by Expression of High Levels of Avidin" by Albertsen et al.

The invention includes vectors with the Ms26 gene. A vector is prepared comprising Ms26, a promoter that will drive expression of the gene in the plant and a terminator region. As noted, the promoter in the construct may be the native promoter or a substituted promoter which will provide expression in the plant. The promoter in the construct may be an inducible promoter, so that expression of the sense or antisense molecule in the construct can be controlled by exposure to the inducer. In this regard, any plant-compatible promoter elements can be employed in the construct, influenced by the end result desired. Those can be plant gene promoters, such as, for example, the promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al., (1987) *Science* 236:1299 and European patent application No. 0 342 926; the barley lipid transfer protein promoter, LTP2 (Kalla et al., *Plant J.* (1994) 6(6): 849-60); the ubiquitin promoter (see for example U.S. Pat. No. 5,510,474); the END2 promoter (Linnestad et al. U.S. Pat. No. 6,903,205); and the polygalacturonase PG47 promoter (See Allen and Lonsdale, *Plant J.* (1993) 3:261-271; WO 94/01572; U.S. Pat. No. 5,412,085). See international application WO 91/19806 for a review of illustrative plant promoters suitably employed in the present invention.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A plant cell containing an inducible regulatory element may be exposed to an inducer by externally applying the inducer to the cell or plant such as by spraying, watering, heating or similar methods. Any inducible promoter can be used in the instant invention. See Ward et al. *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., *Mol. Gen. Genetics* 227: 229-237 (1991) and Gatz et al., *Mol. Gen. Genetics* 243: 32-38 (1994)); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789, 156).

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. Tissue-preferred promoters include those described in Yamamoto et al. (1997) *Plant J.* 12(2): 255-265; Kawamata et al. (1997) *Plant Cell Physiol.* 38(7): 792-803; Hansen et al. (1997) *Mol. Gen. Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol. Biol.* 23(6): 1129-1138; Matsuoka et al. (1993) *Proc Natl. Acad. Sci. USA* 90(20): 9586-9590; and Guevara-Garcia et al. (1993) *Plant J.* 4(3): 495-505. In one embodiment, the promoters are those which preferentially express to the male or female tissue of the plant. The invention does not require that any particular male tissue-preferred promoter be used in the process, and any of the many such promoters known to one skilled in the art may be employed. The native Ms26 promoter described herein is one example of a useful promoter. Another such promoter is the 5126 promoter, which preferentially directs expression of the gene to which it is linked to male tissue of the plants, as described in U.S. Pat. Nos. 5,837,851 and 5,689,051. Other examples include the Ms45 promoter described at U.S. Pat. No. 6,037,523; SF3 promoter described at U.S. Pat. No. 6,452,069; the BS92-7 promoter described at WO 02/063021; a SGB6 regulatory element described at U.S. Pat. No. 5,470,359; the TA29 promoter (Koltunow et al. (1990) "Different temporal and spatial gene expression patterns occur during anther development." *Plant Cell* 2:1201-1224; Goldberg, R. B., Beals, T. P. and Sanders, P. M., (1993) "Anther development: basic principles and practical applications" *Plant Cell* 5:1217-1229; and U.S. Pat. No. 6,399,856); the type 2 metallothionein-like gene promoter (Charbonnel-Campaa et al., *Gene* (2000) 254:199-208); and the *Brassica* Bca9 promoter (Lee et al., *Plant Cell Rep.* (2003) 22:268-273).

Male gamete preferred promoters include the PG47 promoter, supra as well as ZM13 promoter (Hamilton et al., *Plant Mol. Biol.* (1998) 38:663-669); actin depolymerizing factor promoters (such as Zmabp1, Zmabp2; see for example Lopez et al. *Proc. Natl. Acad. Sci.* USA (1996) 93: 7415-7420); the promoter of the maize petctin methylesterase-liked gene, ZmC5 (Wakeley et al. *Plant Mol. Biol.* (1998) 37:187-192); the profilin gene promoter Zmpro1 (Kovar et al., *The Plant Cell* (2000) 12:583-598); the sulphated pentapeptide phyto-sulphokine gene ZmPSK1 (Lorbiecke et al., *Journal of Experimental Botany* (2005) 56(417): 1805-1819); the promoter of the calmodulin binding protein Mpcbp (Reddy et al. *J. Biol. Chem.* (2000) 275(45):35457-70).

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase and nopaline synthase termination regions. See also, Guerineau et al. *Mol. Gen. Genet.* 262:141-144 (1991); Proudfoot, *Cell* 64:671-674 (1991); Sanfacon et al. *Genes Dev.* 5:141-149 (1991); Mogen et al. *Plant Cell* 2:1261-1272 (1990); Munroe et al. *Gene* 91:151-158 (1990); Ballas et al. *Nucleic Acids Res.* 17:7891-7903 (1989); Joshi et al. *Nucleic Acid Res.* 15:9627-9639 (1987).

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al. *Proc. Nat. Acad. Sci.* USA 86:6126-6130 (1989); potyvirus leaders, for example, TEV leader (Tobacco Etch Virus), Allison et al.; MDMV leader (Maize Dwarf Mosaic Virus), *Virology* 154:9-20 (1986); human immunoglobulin heavy-chain binding protein (BiP), Macejak et al. *Nature* 353:90-94

(1991); untranslated leader from the coat protein mRNA of alfalfa mosaic virus (AMV RNA 4), Jobling et al. *Nature* 325:622-625 (1987); Tobacco mosaic virus leader (TMV), Gallie et al. (1989) *Molecular Biology of RNA*, pages 237-256; and maize chlorotic mottle virus leader (MCMV) Lommel et al. *Virology* 81:382-385 (1991). See also Della-Cioppa et al. *Plant Physiology* 84:965-968 (1987). The cassette can also contain sequences that enhance translation and/or mRNA stability such as introns.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. *Plant physiol* 117(4):1235-1252 (1998); Sullivan et al. *Plant Cell* 3(12):1337-48; Sullivan et al., *Planta* (1995) 196(3): 477-84; Sullivan et al., *J. Biol. Chem*. (1992) 267(26):18999-9004) and the like. One skilled in the art will readily appreciate the many options available in expressing a product to a particular organelle. For example, the barley alpha amylase sequence is often used to direct expression to the endoplasmic reticulum (Rogers, *J. Biol. Chem.* 260:3731-3738 (1985)). Use of transit peptides is well known (e.g., see U.S. Pat. Nos. 5,717,084; 5,728,925).

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions, such as transitions and transversions, can be involved.

As noted herein, the present invention provides vectors capable of expressing genes of interest. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the promoter sequence of the present invention operably linked to a heterologous nucleotide sequence in an expression cassette, can also contain at least one additional nucleotide sequence for a gene to be cotransformed into the organism. Alternatively, the additional sequence(s) can be provided on another transformation vector.

Reporter genes can be included in the transformation vectors. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. *Mol. Cell. Biol.* 7:725-737 (1987); Goff et al. *EMBO J.* 9:2517-2522 (1990); Kain et al. *BioTechniques* 19:650-655 (1995); and Chiu et al. *Current Biology* 6:325-330 (1996).

Selectable reporter genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. *EMBO J.* 2:987-992 (1983); methotrexate, Herrera Estrella et al. *Nature* 303:209-213 (1983); Meijer et al. *Plant Mol. Biol.* 16:807-820 (1991); hygromycin, Waldron et al. *Plant Mol. Biol.* 5:103-108 (1985), Zhijian et al. *Plant Science* 108:219-227 (1995); streptomycin, Jones et al. *Mol. Gen. Genet.* 210: 86-91 (1987); spectinomycin, Bretagne-Sagnard et al. *Transgenic Res.* 5:131-137 (1996); bleomycin, Hille et al. *Plant Mol. Biol.* 7:171-176 (1990); sulfonamide, Guerineau et al. *Plant Mol. Biol.* 15:127-136 (1990); bromoxynil, Stalker et al. *Science* 242:419-423 (1988); glyphosate, Shaw et al. *Science* 233:478-481 (1986); and phosphinothricin, DeBlock et al. *EMBO J.* 6:2513-2518 (1987).

Scorable or screenable markers may also be employed, where presence of the sequence produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. *The EMBO Journal vol.* 6 No. 13 pp. 3901-3907); and alkaline phosphatase. Other screenable markers include the anthocyanin/flavonoid genes in general (See discussion at Taylor and Briggs, *The Plant Cell* (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) 8: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the pI gene (Grotewold et al, *Proc. Natl. Acad. Sci. USA* (1991) 88:4587-4591; Grotewold et al., *Cell* (1994) 76:543-553; Sidorenko et al., *Plant Mol. Biol.* (1999) 39:11-19); the bronze locus genes (Ralston et al., *Genetics* (1988) 119:185-197; Nash et al., *Plant Cell* (1990) 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8(5):777-84); and DsRed2 where plant cells transformed with the marker gene are red in color, and thus visually selectable (Dietrich et al. (2002) *Biotechniques* 2(2): 286-293). Additional examples include a p-lactamase gene (Sutcliffe, *Proc. Nat'l. Acad. Sci.* U.S.A. (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. U.S.A.* (1983) 80:1101), which encodes a catechol dioxygenase that can convert chromogenic catechols; an α-amylase gene (Ikuta et al., *Biotech.* (1990) 8:241); and a tyrosinase gene (Katz et al., *J. Gen. Microbiol.* (1983) 129:2703), which encodes an enzyme capable of oxidizing tyrosine to DOPA and dopaquinone, which in turn condenses to form the easily detectable compound melanin. Clearly, many such markers are available to one skilled in the art.

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. See, for example, Miki et al, "Procedures for Introducing Foreign DNA into Plants" in *Methods in Plant Molecular Biotechnology*, supra; Klein et al, *Bio/Technology* 10:268 (1992); and Weising et al., *Ann. Rev. Genet.* 22: 421-477 (1988). For example, the DNA construct may be introduced into the genomic DNA of the plant cell using techniques such as microprojectile-mediated delivery, Klein et al., *Nature* 327: 70-73 (1987); electroporation, Fromm et al., *Proc. Natl. Acad. Sci.* 82: 5824 (1985); polyethylene glycol (PEG) precipitation, Paszkowski et al., *EMBO J.* 3: 2717-2722 (1984); direct gene transfer WO 85/01856 and EP No. 0 275 069; in vitro protoplast transformation, U.S. Pat. No. 4,684,611; and microinjection of plant cell protoplasts or embryogenic callus, Crossway, *Mol. Gen. Genetics* 202:179-185 (1985). Co-cultivation of plant tissue with *Agrobacterium tumefaciens* is another option, where the DNA constructs are placed into a binary vector system. See e.g., U.S. Pat. No. 5,591,616; Ishida et al., "High Efficiency Transformation of Maize (*Zea mays* L.) mediated by *Agrobacterium tumefaciens*" *Nature Biotechnology* 14:745-750 (1996). The virulence functions of the *Agrobacterium tumefaciens* host will direct the insertion of the construct into the plant cell DNA when the cell is infected by the bacteria. See, for example Horsch et al., *Science* 233: 496-498 (1984), and Fraley et al., *Proc. Natl. Acad. Sci.* 80: 4803 (1983).

Standard methods for transformation of canola are described at Moloney et al. "High Efficiency Transformation of *Brassica napus* using *Agrobacterium* Vectors" *Plant Cell Reports* 8:238-242 (1989). Corn transformation is described by Fromm et al, *Bio/Technology* 8:833 (1990) and Gordon-Kamm et al, supra. *Agrobacterium* is primarily used in dicots, but certain monocots such as maize can be transformed by *Agrobacterium*. See supra and U.S. Pat. No. 5,550,318. Rice transformation is described by Hiei et al., "Efficient Transformation of Rice (*Oryza sativs* L.) Mediated by *Agrobacterium* and Sequence Analysis of the Boundaries of the T-DNA" *The Plant Journal* 6(2): 271-282 (1994, Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. *Sorghum* transformation is described at Casas et al, supra and *sorghum* by Wan et al, *Plant Physicol.* 104:37 (1994). Soybean transformation is described in a number of publications, including U.S. Pat. No. 5,015,580.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art.

The plant breeding methods used herein are well known to one skilled in the art. For a discussion of plant breeding techniques, see Poehlman (1987) *Breeding Field Crops*. AVI Publication Co., Westport Conn. Many of the plants which would be most preferred in this method are bred through techniques that take advantage of the plant's method of pollination.

Backcrossing methods may be used to introduce a gene into the plants. This technique has been used for decades to introduce traits into a plant. An example of a description of this and other plant breeding methodologies that are well known can be found in references such as *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

In certain embodiments of the invention, it is desirable to maintain the male sterile homozygous recessive condition of a male sterile plant, when using a transgenic restoration approach, while decreasing the number of plants, plantings and steps needed for maintenance plant with such traits. Homozygosity is a genetic condition existing when identical alleles reside at corresponding loci on homologous chromosomes. Heterozygosity is a genetic condition existing when different alleles reside at corresponding loci on homologous chromosomes. Hemizygosity is a genetic condition existing when there is only one copy of a gene (or set of genes) with no allelic counterpart on the sister chromosome. In an embodiment, the homozygous recessive condition results in conferring on the plant a trait of interest, which can be any trait desired and which results from the recessive genotype, such as increased drought or cold tolerance, early maturity, changed oil or protein content, or any of a multitude of the many traits of interest to plant breeders. In one embodiment, the homozygous recessive condition confers male sterility upon the plant. When the sequence which is the functional complement of the homozygous condition is introduced into the plant (that is, a sequence which, when introduced into and expressed in the plant having the homozygous recessive condition, restores the wild-type condition), fertility is restored by virtue of restoration of the wild-type fertile phenotype.

Maintenance of the homozygous recessive condition is achieved by introducing a restoration transgene construct into a plant that is linked to a sequence which interferes with the function or formation of male gametes of the plant to create a maintainer or donor plant. The restoring transgene, upon introduction into a plant that is homozygous recessive for the genetic trait, restores the genetic function of that trait, with the plant producing only viable pollen containing a copy of the recessive allele but does not contain the restoration transgene. The transgene is kept in the hemizygous state in the maintainer plant. By transgene, it is meant any nucleic acid sequence which is introduced into the genome of a cell by genetic engineering techniques. A transgene may be a native DNA sequence, or a heterologous DNA sequence (i.e., "foreign DNA"). The term native DNA sequence refers to a nucleotide sequence which is naturally found in the cell but that may have been modified from its original form. The pollen from the maintainer can be used to fertilize plants that are homozygous for the recessive trait, and the progeny will therefore retain their homozygous recessive condition. The maintainer plant containing the restoring transgene construct is propagated by self-fertilization, with the resulting seed used to produce further plants that are homozygous recessive plants and contain the restoring transgene construct.

The maintainer plant serves as a pollen donor to the plant having the homozygous recessive trait. The maintainer is optimally produced from a plant having the homozygous recessive trait and which also has nucleotide sequences introduced therein which would restore the trait created by the homozygous recessive alleles. Further, the restoration sequence is linked to nucleotide sequences which interfere with the function or formation of male gametes. The gene can operate to prevent formation of male gametes or prevent function of the male gametes by any of a variety of well-know modalities and is not limited to a particular methodology. By way of example but not limitation, this can include use of genes which express a product cytotoxic to male gametes (See for example, U.S. Pat. No. 5,792,853; U.S. Pat. No. 5,689,049; PCT/EP89/00495); inhibit product formation of another gene important to male gamete function or formation (See, U.S. Pat. Nos. 5,859,341; 6,297,426); combine with another gene product to produce a substance preventing gene formation or function (See U.S. Pat. Nos. 6,162,964; 6,013,859; 6,281,348; 6,399,856; 6,248,935; 6,750,868; 5,792,853); are antisense to or cause co-suppression of a gene critical to male gamete function or formation (See U.S. Pat. Nos. 6,184,439; 5,728,926; 6,191,343; 5,728,558; 5,741,684); interfere with expression through use of hairpin formations (Smith et al. (2000) *Nature* 407:319-320; WO 99/53050 and WO 98/53083) or the like. Many nucleotide sequences are known which inhibit pollen formation or function and any sequences which accomplish this function will suffice. A discussion of genes which can impact proper development or function is included at U.S. Pat. No. 6,399,856 and includes dominant negative genes such as cytotoxin genes, methylase genes, and growth-inhibiting genes. Dominant negative genes include diphtheria toxin A-chain gene (Czako, M. and An, G. (1991) "Expression of DNA coding for Diptheria toxin Chain A is toxic to plant cells" *Plant Physiol.* 95 687-692. and Greenfield et al *PNAS* 80:6853 (1983), Palmiter et al *Cell* 50:435 (1987)); cell cycle division mutants such as CDC in maize (Colasanti, J., Tyers, M. and Sundaresan, V., "Isolation and Characterization of cDNA clones encoding a functional P34 cdc2 homologue from *Zea mays*" PNAS 88, 3377-3381 (1991)); the WT gene (Farmer, A. A., Loftus, T. M., Mills, A. A., Sato, K. V., Neill, J., Yang, M., Tron, T., Trumpower, B. L. and Stanbridge, E. G. *Hum. Mol. Genet.* 3, 723-728 (1994)); and P68 (Chen, J. J., Pal, J. K., Petryshyn, R., Kuo, I., Yang, J. M., Throop, M. S., Gehrke, L. and London, I. M. "Eukaryotic translation initiation kinases" *PNAS* 88, 315-319 (1991)).

Further examples of so-called "cytotoxic" genes are discussed supra and can include, but are not limited to pectate lyase gene pelE, from *Erwinia chrysanthermi* (Kenn et al *J. Bacteroil* 168:595 (1986)); T-urf13 gene from cms-T maize mitochondrial genomes (Braun et al *Plant Cell* 2:153 (1990); Dewey et al. *PNAS* 84:5374 (1987)); CytA toxin gene from *Bacillus thuringiensis Israeliensis* that causes cell membrane disruption (McLean et al *J. Bacteriol* 169:1017 (1987), U.S. Pat. No. 4,918,006); DNAses, RNAses, (U.S. Pat. No. 5,633,441); proteases, or a genes expressing anti-sense RNA. A suitable gene may also encode a protein involved in inhibiting pistil development, pollen stigma interactions, pollen tube growth or fertilization, or a combination thereof. In addition genes that either interfere with the normal accumulation of starch in pollen or affect osmotic balance within pollen may also be suitable.

In an illustrative embodiment, the DAM-methylase gene is used, discussed supra and at U.S. Pat. Nos. 5,792,852 and 5,689,049, the expression product of which catalyzes methylation of adenine residues in the DNA of the plant. Methylated adenines will affect cell viability and will be found only in the tissues in which the DAM-methylase gene is expressed. In another embodiment, an α-amylase gene can be used with a male tissue-preferred promoter. During the initial germinating period of cereal seeds, the aleurone layer cells will synthesize α-amylase, which participates in hydrolyzing starch to form glucose and maltose, so as to provide the nutrients needed for the growth of the germ (J. C. Rogers and C. Milliman, *J. Biol. Chem.*, 259 (19): 12234-12240, 1984; Rogers, J. C., *J. Biol. Chem.*, 260: 3731-3738, 1985). In an embodiment, the α-amylase gene used can be the *Zea mays* α-amylase-1 gene. Young et al. "Cloning of an α-amylase cDNA from aleurone tissue of germinating maize seed" *Plant Physiol.* 105 (2) 759-760 and GenBank accession No. L25805, GI:426-481). Sequences encoding α-amylase are not typically found in pollen cells, and when expression is directed to male tissue, the result is a breakdown of the energy source for the pollen grains, and repression of pollen development.

One skilled in this area readily appreciates the methods described herein are applicable to any other crops which have the potential to outcross. By way of example, but not limitation it can include maize, soybean, *sorghum*, or any plant with the capacity to outcross.

Ordinarily, to produce more plants having the recessive condition, one might cross the recessive plant with another recessive plant. This may not be desirable for some recessive traits and may be impossible for recessive traits affecting reproductive development. Alternatively, one could cross the homozygous plant with a second plant having the restoration gene, but this requires further crossing to segregate away the restoring gene to once again reach the recessive phenotypic state. Instead, in one process the homozygous recessive condition can be maintained, while crossing it with the maintainer plant. This method can be used with any situation in which is it desired to continue the recessive condition. This results in a cost-effective system that is relatively easy to operate to maintain a population of homozygous recessive plants.

A sporophytic gene is one which operates independently of the gametes. When the homozygous recessive condition is one which produces male sterility by preventing male sporophyte development, the maintainer plant, of necessity, must contain a functional restoring transgene construct capable of complementing the mutation and rendering the homozygous recessive plant able to produce viable pollen. Linking this sporophytic restoration gene with a second functional nucleotide sequence which interferes with the function or formation of the male gametes of the plant results in a maintainer plant that produces pollen containing only the recessive allele of the sporophytic gene at the its native locus due to the action of the second nucleotide sequence in interfering with pollen formation or function. This viable pollen fraction is non-transgenic with regard to the restoring transgene construct.

In a still further embodiment, a marker gene, as discussed supra, may be provided in the construct with the restoring transgene. By way of example without limitation, use of a herbicide resistant marker, such as bar allows one to eliminate cells not having the restoring transgene. In yet another example, when using a scorable marker, such as a red fluorescent marker, such as DsRed2, any inadvertent transmission of the transgene can also be detected visually, and such escapes eliminated from progeny. Clearly, many other variations in the restoring construct are available to one skilled in the art.

In an illustrative embodiment, a method of maintaining a homozygous recessive condition of a male sterile plant at a genetic locus is provided, in which is employed a first nucleotide sequence which is a gene critical to male fertility, a second nucleotide sequence which inhibits the function or formation of viable male gametes, an optional third nucleotide sequence which is operably linked to the first sequence and preferentially expresses the sequence in male plant cells, an optional fourth nucleotide sequence operably linked to a fourth nucleotide sequence, the fourth sequence directing expression to male gametes, and an optional fifth nucleotide sequence which is a selectable or scorable marker allowing for selection of plant cells.

For example, it is desirable to produce male sterile female plants for use in the hybrid production process which are sterile as a result of being homozygous for a mutation in the Ms45 gene; a gene, which is critical to male fertility. Such a mutant Ms45 allele is designated as ms45 and a plant that is homozygous for ms45 (represented by the notation ms45/ms45) displays the homozygous recessive male sterility phenotype and produces no functional pollen. See, U.S. Pat. Nos. 5,478,369; 5,850,014; 6,265,640; and 5,824,524. In both the inbred and hybrid production processes, it is highly desired to maintain this homozygous recessive condition. When sequences encoding the Ms45 gene are introduced into a plant having the homozygous condition, male fertility results. By the method of the invention, a plant which is ms45/ms45 homozygous recessive may have introduced into it a functional sporophytic Ms45 gene, and thus is male fertile. This gene can be linked to a gene which operates to render pollen containing the restoring transgene construct nonfunctional or prevents its formation, or which produces a lethal product in pollen, linked to the promoter directing its expression to the male gametes to produce a plant that only produced pollen containing ms45 without the restoring transgene construct.

An example is a construct which includes the Ms45 gene, linked with a 5126 promoter, a male tissue-preferred promoter (See U.S. Pat. Nos. 5,750,868; 5,837,851; and 5,689,051) and further linked to the cytotoxic DAM methylase gene under control of the polygalacturonase promoter, PG47 promoter (See U.S. Pat. No. 5,792,853; U.S. Pat. No. 5,689,049) in a hemizygotic condition. Therefore the resulting plant produces pollen, but the only viable pollen results from the alle not containing the resoring Ms45/DAM methylase construct and thus contains only the ms45 gene. It can therefore be used as a pollinator to fertilize the homozygous recessive plant (ms45/ms45), and progeny produced will continue to be male sterile as a result of maintaining homozygosity for ms45. The progeny will also not contain the introduced restoring transgene construct.

In yet another restoring construct example, the Ms26 gene is linked with a 5126 promoter, and further linked to the Zea mays α-amylase gene under control of the male tissue-preferred PG47 promoter. The scorable marker used in an embodiment is DS-RED EXPRESS.

A desirable result of the process of the invention is that the plant having the restorer nucleotide sequence may be self-fertilized, that is pollen from the plant transferred to the flower of the same plant to achieve the propagation of restorer plants. (Note that in referring to "self fertilization", it includes the situation where the plant producing the pollen is fertilized with that same the pollen, and the situation where two or more identical inbred plants are planted together and pollen from the identical inbred plant pollinate a different identical inbred plant). The pollen will not have the restoring transgene construct but it will be contained in 50% of the ovules (the female gamete). The seed resulting from the self-fertilization can be planted, and selection made for the seed having the restoring transgene construct. The selection process can occur by any one of many known processes; the most common where the restoration nucleotide sequence is linked to a marker gene. The marker can be scorable or selectable, and allows those plants produced from the seed having the restoration gene to be identified.

In an embodiment of the invention, it is possible to provide that the male gamete-tissue preferred promoter is inducible. Additional control is thus allowed in the process, where so desired, by providing that the plant having the restoration nucleotide sequences is constitutively male sterile. This type of male sterility is set forth the in U.S. Pat. No. 5,859,341. In order for the plant to become fertile, the inducing substance must be provided, and the plant will become fertile. Again, when combined with the process of the invention as described supra, the only pollen produced will not contain the restoration nucleotide sequences.

Further detailed description is provided below by way of instruction and illustration and is not intended to limit the scope of the invention.

EXAMPLE 1

Identification and Cosegregation of ms26-m2::Mu8

Families of plants from a Mutator (Mu) population were identified that segregated for plants that were mostly male sterile, with none or only a few extruded abnormal anthers, none of which had pollen present. Male sterility is expected to result from those instances where a Mu element has randomly integrated into a gene responsible for some step in microsporogenesis, disrupting its expression. Plants from a segregating $F_2$ family in which the male sterile mutation was designated ms26*-SBMu200, were grown and classified for male fertility/sterility based on the above criteria. Leaf samples were taken and DNA subsequently isolated on approximately 20 plants per phenotypic classification, that is male fertility vs. male sterility.

Southern analysis was performed to confirm association of Mu with sterility. Southern analysis is a well known technique to those skilled in the art. This common procedure involves isolating the plant DNA, cutting with restriction endonucleases, fractioning the cut DNA by molecular weight on an agarose gel, and transferring to nylon membranes to fix the separated DNA. These membranes are subsequently hybridized with a probe fragment that was radioactively labeled with $P^{32}$P-dCTP, and washed in an SDS solution. Southern, E., "Detection of Specific Sequences Among DNA Fragments by Gel Electrophoresis," *J. Mol. Biol.* 98:503-317 (1975). Plants from a segregating $F_2$ ms26*-SBMu200 family were grown and classified for male fertility/sterility. Leaf samples and subsequent DNA isolation was conducted on approximately 20 plants per phenotypic classification. DNA (~7 ug) from 5 fertile and 12 sterile plants was digested with EcoRI and electrophoresed through a 0.75% agarose gel. The digested DNA was transferred to nylon membrane via Southern transfer. The membrane was hybridized with an internal fragment from the Mu8 transposon. Autoradiography of the membrane revealed cosegregation of an approximately 5.6 Kb EcoRI fragment with the sterility phenotype as shown in FIG. 1. This EcoRI band segregated in the fertile plants suggesting a heterozygous wild type condition for the allele

EXAMPLE 2

Library Construction, Screening, and Mapping

The process of genomic library screenings is commonly known among those skilled in the art and is described at Sambrook, J., Fritsch, E. F., Maniatis T., et al., *Molecular Cloning: A Laboratory Manual*, Cold Spring Harbor Laboratory, Cold Spring Harbor Lab Press, Plainview, N.Y. (1989). Libraries were created as follows.

DNA from a sterile plant was digested with EcoRI and run on a preparative gel. DNA with a molecular weight between 5.0 and 6.0 Kb was excised from the gel, electroeluted and ethanol precipitated. This DNA was ligated into the Lambda Zap vector (Stratagene™) using the manufacturer's protocol. The ligated DNA was packaged into phage particles using Gigapack Gold (Stratagene™). Approximately 500,000 PFU were plated and lifted onto nitrocellulose membranes. Membranes were hybridized with the Mu8 probe. A pure clone was obtained after 3 rounds of screening. The insert was excised from the phage as a plasmid and designated SBMu200-3.1. A PstI border fragment from this clone was isolated and used to reprobe the original EcoRI cosegregation blot as shown in FIG. 2B. The approximately 5.6 kb EcoRI fragment is homozygous in all the sterile plants, which confirms that the correct Mu fragment was isolated. Three of the fertile plants are heterozygous for the 5.5 kb EcoRI band and a 4.3 Kb EcoRI band. Two of the fertile plants are homozygous for the 4.3 kb EcoRI band, presumably the wild type allele.

Figure 13:
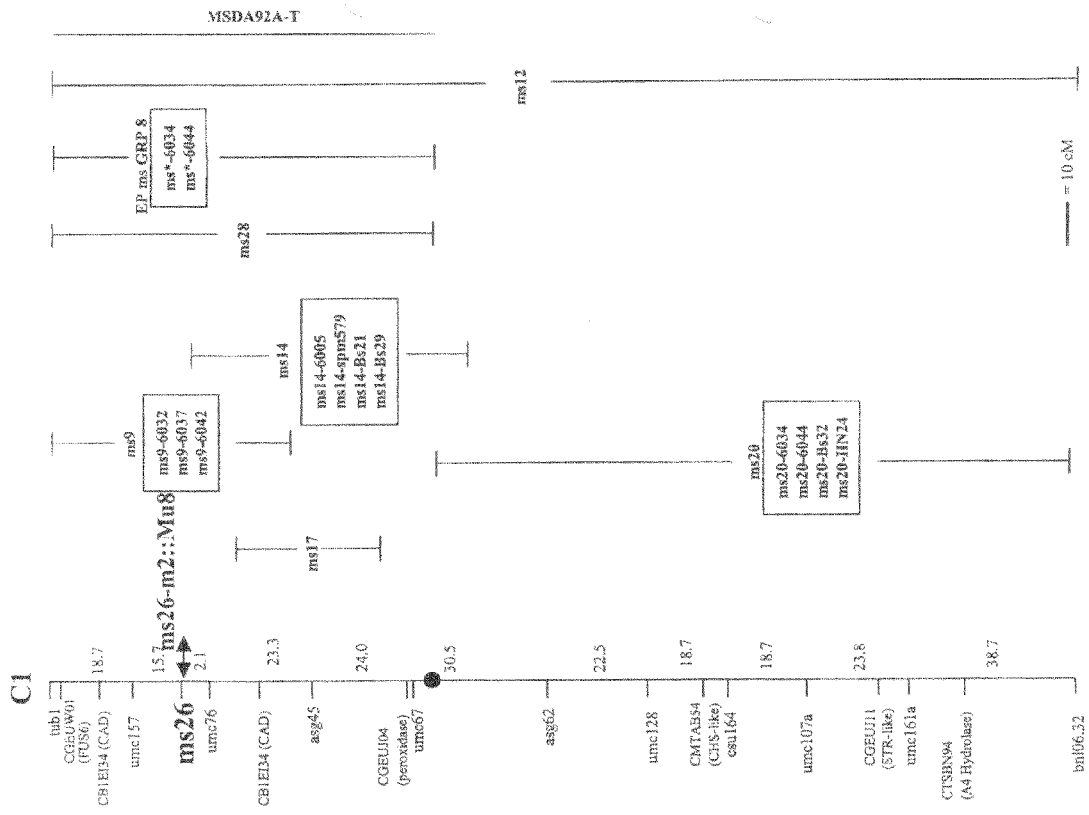
FIG. 13 is a representation of the mapping of the male sterility gene ms26.

The PstI probe was used to map the ms*-SBMu200 mutation in an RFLP mapping population. The mutant mapped to the short arm of chromosome 1, near the male sterile locus, Ms26 (Loukides et al., (1995) *Amer. J. Bot* 82, 1017-1023). To test whether ms*-SBMu200 was an allele of ms26-ref, ms*-SBMu200 and ms26-ref were crossed with each other using a known heterozygote as the pollen donor. The testcross progeny segregated male-sterile and wild-type plants in a 1:1 ratio, indicating allelism between ms*-SBMu200 and ms26-ref. The ms*-SBMu200 allele was designated ms26-m2::Mu8. The map location is shown in FIG. 13.

EXAMPLE 3

Identification and Cloning of Additional ms26 Alleles

An additional Mu insertion mutations in Ms26 was identified by using a polymerase chain reaction (PCR) primer for Mu and a gene specific primer for Ms26 and screening a population of Mu $F_1$ families. Sequence analyses of the PCR products showed that all three Mu insertions occurred in the second exon (FIG. 1). The $F_2$ seeds from one of these families were grown and examined for male fertility/sterility. Southern blot analyses of this family confirmed the cosegregation of the Mu insertion in Ms26 with the male-sterile phenotype and the allele was designated ms26-m3::Mu.

The ms26 allele described in Loukides et al., (1995) Amer. J. Bot 82, 1017-1023 and designated ms26-ref was also investigated. To analyze the mutation in ms26-ref, Ms26 genomic sequences were cloned from ms26-ref sterile and fertile plants. Ms26 was cloned as a ~4.2 kb EcoRI fragment and ms26-ref cloned as a ~6 kb HindIII fragment and an overlapping ~2.3 kb EcoRI fragment from the sterile plant. Sequence analysis revealed the presence of a new segment (1,430 bp) in the last exon of the ms26-ref allele shown in FIG. 1. An 8 bp host site duplication (GCCGGAGC) was found that flanks the inserted element and the element also contains a 15 bp terminal inverted repeat (TIR) (TAGGGGTGAAAACGG; SEQ ID NO: 23). The transposon sequence is shown in FIG. 15 (SEQ ID NO: 10). The ms26-ref genomic sequence in its entirety is shown in FIG. 16, SEQ ID NO: 11. A variant of the ms26-ref allele was also found. Sequence analysis of this allele, designated ms26'-0406, was found to have lost the 1430 bp segment found in the last exon of the ms26-ref allele but left an 8 bp footprint at the site of insertion. Plants homozygous for the ms26'-0406 allele were male sterile. A comparison of the excision allele, ms26'-0406 (SEQ ID NO: 8) with the region in the wild-type Ms26 gene (SEQ ID NO: 9) is shown in FIG. 14.

EXAMPLE 4

Expression Analysis and cDNA Isolation

Figure 3:
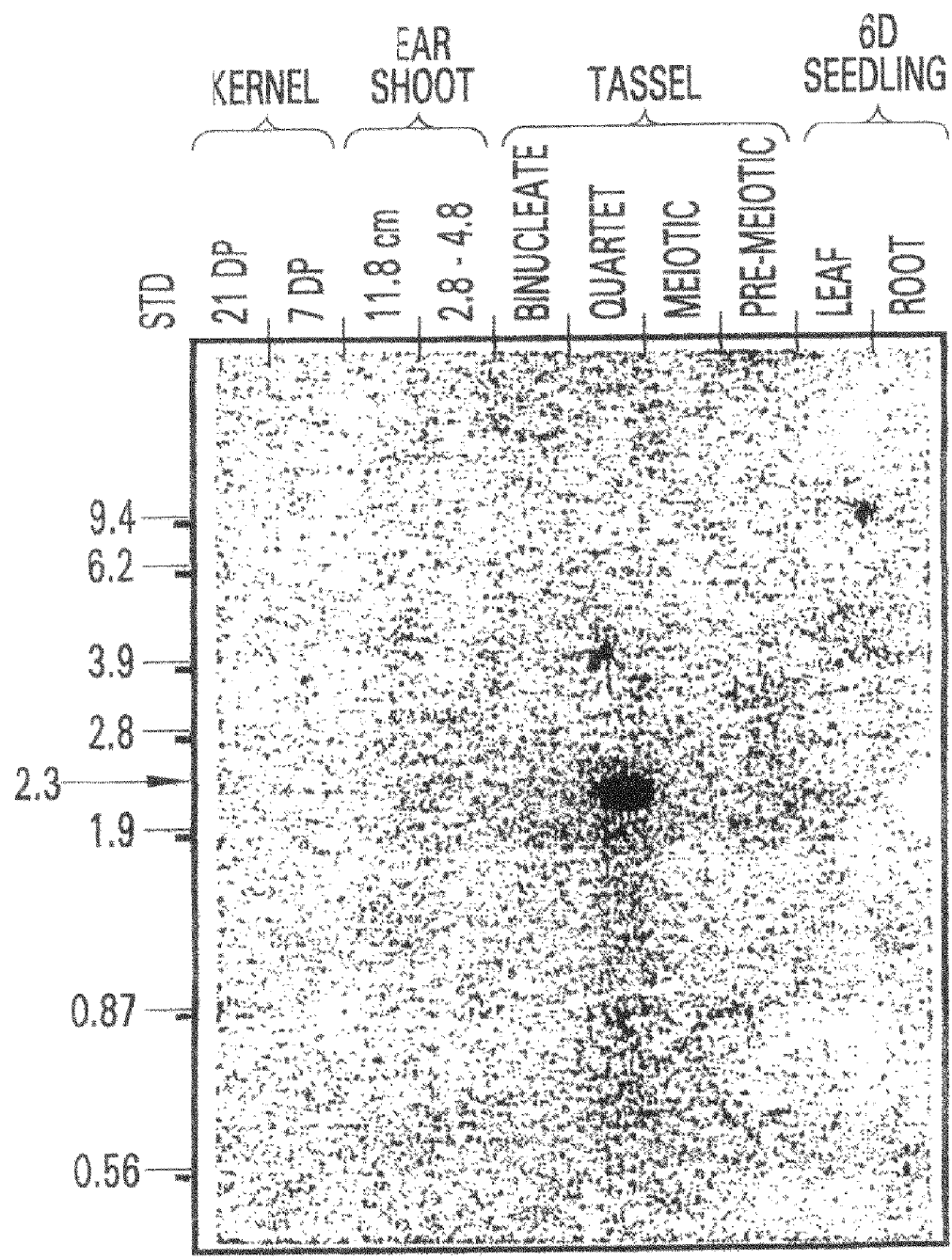
FIG. 3. is a Northern Blot analysis gel hybridized with a PstI fragment isolated from the Ms26 gene.

Northern analysis can be used to detect expression of genes characteristic of anther development at various states of microsporogenesis. Northern analysis is also a commonly used technique known to those skilled in the art and is similar to Southern analysis except that mRNA rather than DNA is isolated and placed on the gel. The RNA is then hybridized with the labeled probe. Potter, E., et al., "Thyrotrotropin Releasing Hormone Exerts Rapid Nuclear Effects to Increase Production of the Primary Prolactin in RNA Transcript," *Proc. Nat. Acad. Sci. USA* 78:6662-6666 (1981), Lechelt, et al., "Isolation & Molecular Analysis of the Plows," *Mol. Gen. Genet.* 219:225-234 (1989). The PstI fragment from the SBMu200-3.1 clone was used to probe a Northern blot containing kernel, immature ear, seedling and tassel RNA. A signal was seen only in tassel RNA at approximately the quartet stage of microsporogenesis, as reflected in FIG. 3. The transcript is about 2.3 kb in length. The same probe was also used to screen a cDNA library constructed from mRNA isolated from meiotic to late uninucleate staged anthers. One clone, designated Ms26-8.1, was isolated from the library.

EXAMPLE 5

Sequence and Expression Analysis

Figure 17:
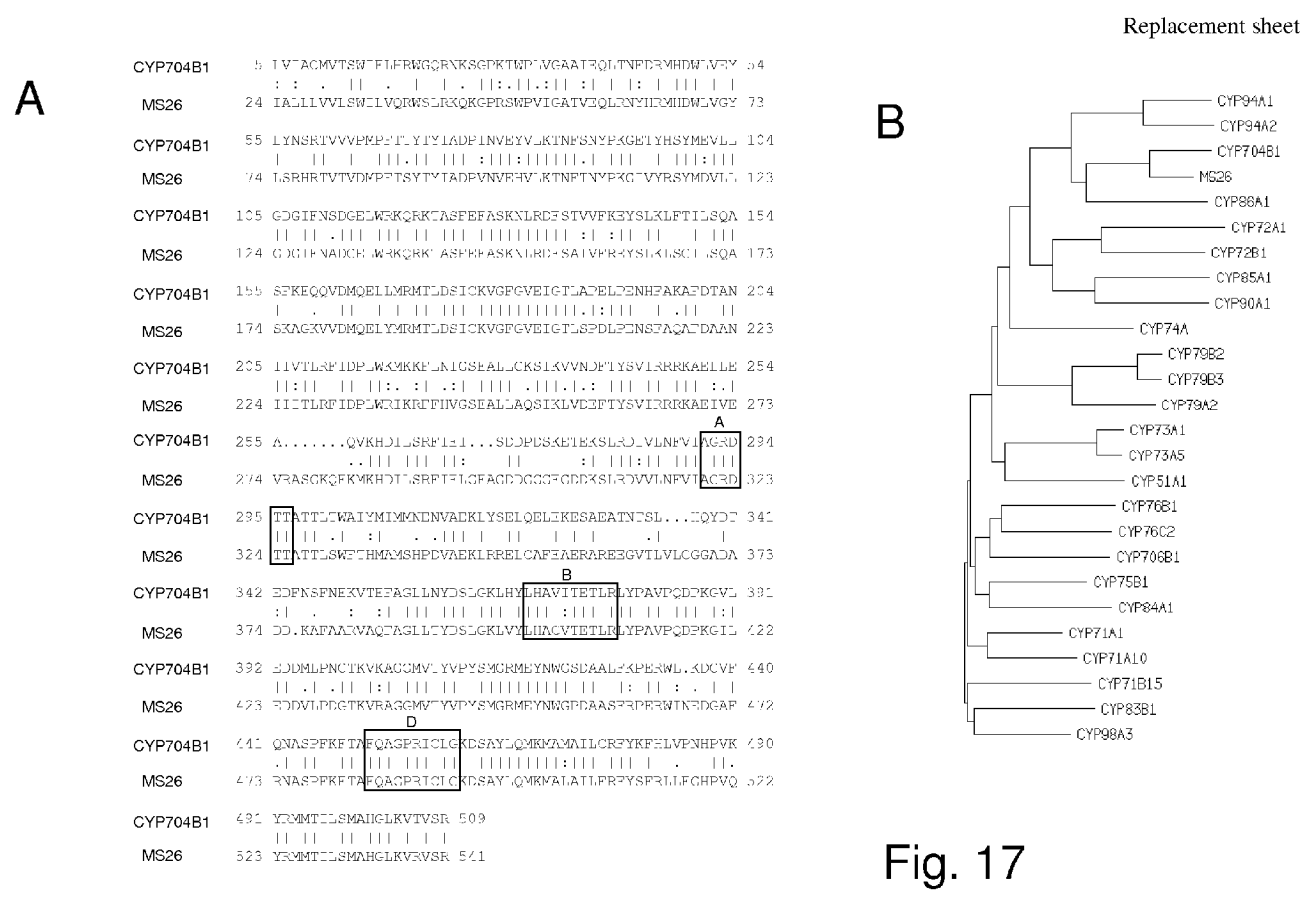

The SBMu200-3.1 genomic clone and the Ms26-8.1 cDNA clone were sequenced by Loftstrand Labs Limited. Sanger, F., Nicklen, S., Coulson A. R. (1977) "DNA sequencing with chain terminating inhibitors" *Proc. Natl. Acad. Sci. USA* 74:5463-5467. The sequences are set forth in FIGS. 4 and 5 and the comparison is at FIG. 6. The cDNA/genomic comparison reveals five introns are present in the genomic clone. The Mu8 insertion occurs in exon 1. Testing for codon preference and non-randomness in the third position of each codon was consistent with the major ORF in the cDNA being the likely protein-coding ORF. There is a putative Met start codon at position 1089 in the genomic clone. The cDNA homology with respect to the genomic clone begins at nucleotide 1094. Thus Ms26-8.1 does not represent a full length clone and lacks 5 bases up to the putative Met start codon. A database search revealed significant homology to P450 enzymes found in yeast, plants and mammals. P450 enzymes have been widely studied and three characteristic protein domains have been elucidated. The Ms26 protein contains several structural motifs characteristic of eukaryotic P450's, including the heme-binding domain FxxGxRxCxG (domain D; SEQ ID NO: 24), domain A A/GGXD/ETT/S (dioxygen-binding), domain B (steroid-binding), and domain C. The highly conserved heme-binding motif was found in MS26 as FQAGPRICLG (SEQ ID NO: 25), 51 amino acids away from C-terminus. The dioxygen binding domain AGRDTT (SEQ ID NO: 35) was located between amino acids 320-325. The steroid-binding domain was found as LVYLHACVTETLR (SEQ ID NO: 27), amino acids 397-409. The most significant homologous sequence detected in Genebank database is a deduced protein sequence from rice (GeneBank accession number 19071651). The second highest homologous sequence is a putative *Arabidopsis* P450 gene (CYP704B1) whose function is also unknown. FIG. 17A shows a sequence alignment between CYP704B1 (SEQ ID NO: 12) and Ms26 (SEQ ID NO: 13). Phylogenetic tree analysis of some P450 genes revealed that Ms26 is most closely related to P450s involved in fatty acid omega-hydroxylation found in *Arabidopsis thaliana* and *Vicia sativa* (FIG. 17B). The translational frame shift caused in the ms26'-0406 excision mutation is believed to destroy the activity of the heme binding domain, thus resulting in sterility. See the comparison at FIG. 18 (Ms26 cDNA at SEQ ID NO: 14; fertile exon 5 region at SEQ ID NO: 15 and sterile exon 5 region is SEQ ID NO: 16).

Figure 7:
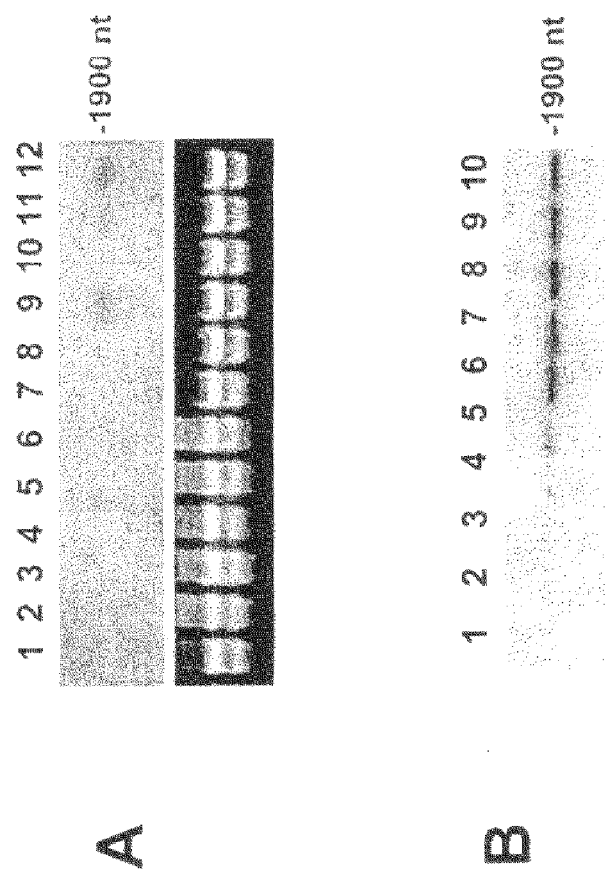
FIG. 7A is a Northern analysis gel showing expression in various plant tissues and FIG. 7B is a gel showing expression stages of microsporogenesis

Further expression studies were done using the Ms26 cDNA probe against a northern containing mRNA at discrete stages of microsporogenesis. FIG. 7A shows a Northern blot with RNA samples from different tissues including root (1), leaf (2), husk (3), cob (4), ear spikelet (5), silk (6), immature embryo (7) mature embryo (8), and tassel from, fertile plant (9), ms26-m2::Mu8 sterile plant (10), ms26-ref sterile plant (11) and fertile plant (12). A hybridization signal using Ms26 cDNA was detected only in tassel tissues. FIG. 7B shows a Northern blot containing mRNA at discrete stages of microsporogenesis. Hybridization signals using Ms26 cDNA were detected from meiosis II/quartet stage (4) to late-uninucleate stage (10), with the maximal signal being observed from early-uninucleate through late-uninucleate stage (10).

EXAMPLE 6

Identification of Promoter and its Essential Regions

A putative TATA box can be identified by primer extension analysis as described in by *Current Protocols in Molecular Biology*, Ausubel, F. M. et al. eds; John Wiley and Sons, New York pp. 4.8.1-4.8.5 (1987).

Regulatory regions of anther genes, such as promoters, may be identified in genomic subclones using functional analysis, usually verified by the observation of reporter gene expression in anther tissue and a lower level or absence of reporter gene expression in non-anther tissue. The possibility of the regulatory regions residing "upstream" or 5' ward of the translational start site can be tested by subcloning a DNA fragment that contains the upstream region into expression vectors for transient expression experiments. It is expected that smaller subgenomic fragments may contain the regions essential for male-tissue preferred expression. For example, the essential regions of the CaMV 19S and 35S promoters have been identified in relatively small fragments derived from larger genomic pieces as described in U.S. Pat. No. 5,352,605.

The selection of an appropriate expression vector with which to test for functional expression will depend upon the host and the method of introducing the expression vector into the host and such methods are well known to one skilled in the art. For eukaryotes, the regions in the vector include regions that control initiation of transcription and control processing. These regions are operably linked to a reporter gene such as UidA, encoding—glucuronidase (GUS), or luciferase. General descriptions and examples of plant expression vectors and reporter genes can be found in Gruber, et al., "Vectors for Plant Transformation" in *Methods in Plant Molecular Biology and Biotechnology*; Glick, et al. eds; CRC Press; pp. 89-119; (1993). GUS expression vectors and GUS gene cassettes are commercially available from Clonetech, Palo Alto, Calif., while luciferase expression vectors and luciferase gene cassettes are available from Promega Corporation, Madison, Wis. Ti plasmids and other *Agrobacterium* vectors are described in Ishida, Y., et al., *Nature Biotechnology*; Vol. 14; pp. 745-750; (1996) and in U.S. Pat. No. 5,591,616 "Method for Transforming Monocotyledons" (1994).

Expression vectors containing putative regulatory regions located in genomic fragments can be introduced into intact tissues such as staged anthers, embryos or into callus. Methods of DNA delivery include microprojectile bombardment, DNA injection, electroporation and *Agrobacterium*-mediated gene transfer (see Gruber, et al., "Vectors for Plant Transformation," in *Methods in Plant Molecular Biology and Biotechnology*, Glick, et al. eds.; CRC Press; (1993); U.S. Pat. No. 5,591,616; and Ishida, Y., et al., *Nature Biotechnology*; Vol. 14; pp. 745-750; (1996)). General methods of culturing plant tissues are found in Gruber, et al., supra and Glick, supra.

For the transient assay system, staged, isolated anthers are immediately placed onto tassel culture medium (Pareddy, D. R. and J. F. Petelino, *Crop Sci. J.*; Vol. 29; pp. 1564-1566; (1989)) solidified with 0.5% Phytagel (Sigma, St. Louis) or other solidifying media. The expression vector DNA is introduced within 5 hours preferably by microprojectile-mediated delivery with 1.2 µm particles at 1000-1100 Psi. After DNA delivery, the anthers are incubated at 26° C. upon the same tassel culture medium for 17 hours and analyzed by preparing a whole tissue homogenate and assaying for GUS or for luciferase activity (see Gruber, et al., supra).

Upstream of the likely translational start codon of Ms26, 1088 bp of DNA was present in the genomic clone ms26-m2::Mu8. Translational fusions via an engineered NcoI site were generated with reporter genes encoding luciferase and β-glucuronidase to test whether this fragment of DNA had promoter activity in transient expression assays of bombarded plant tissues. Activity was demonstrated in anthers and not in coleoptiles, roots and calli, suggesting anther-preferred or anther-specific promoter activity.

A reasonable TATA box was observed by inspection, about 83-77 bp upstream of the translational start codon. The genomic clone ms26-m2::Mu8 thus includes about 1005 bp upstream of the possible TATA box. For typical plant genes, the start of transcription is 26-36 bp downstream of the TATA box, which would give the Ms26 mRNA a 5'-nontranslated leader of about 48-58 nt. The total ms26-m2::Mu8 subgenomic fragment of 1088 bp, including nontranslated leader, start of transcription, TATA box and sequences upstream of the TATA box, was thus shown to be sufficient for promoter activity. See FIG. 8, which is SEQ. ID NO: 5. The putative TATA box (TATATCA) is underlined. Thus, the present invention encompasses a DNA molecule having a nucleotide sequence of SEQ ID NO: 5 (or those with sequence identity) and having the function of a male tissue-preferred regulatory region.

Deletion analysis can occur from both the 5' and 3' ends of the regulatory region: fragments can be obtained by site-directed mutagenesis, mutagenesis using the polymerase chain reaction, and the like (*Directed Mutagenesis: A Practical Approach*; IRL Press; (1991)). The 3' end of the male tissue-preferred regulatory region can be delineated by proximity to the putative TATA box or by 3' deletions if necessary.

The essential region may then be operably linked to a core promoter of choice. Once the essential region is identified, transcription of an exogenous gene may be controlled by the male tissue-preferred region of Ms26 plus a core promoter. The core promoter can be any one of known core promoters such as a Cauliflower Mosaic Virus 35S or 19S promoter (U.S. Pat. No. 5,352,605), Ubiquitin (U.S. Pat. No. 5,510, 474), the IN2 core promoter (U.S. Pat. No. 5,364,780), or a Figwort Mosaic Virus promoter (Gruber, et al., "Vectors for Plant Transformation" in *Methods in Plant Molecular Biology and Biotechnology*; Glick, et al. eds.; CRC Press; pp. 89-119; (1993)). Preferably, the promoter is the core promoter of a male tissue-preferred gene or the CaMV 35S core promoter. More preferably, the promoter is a promoter of a male tissue-preferred gene and in particular, the Ms26 core promoter.

Further mutational analysis, for example by linker scanning, a method well known to the art, can identify small segments containing sequences required for anther-preferred expression. These mutations may introduce modifications of functionality such as in the levels of expression, in the timing of expression, or in the tissue of expression. Mutations may also be silent and have no observable effect.

Figure 9:
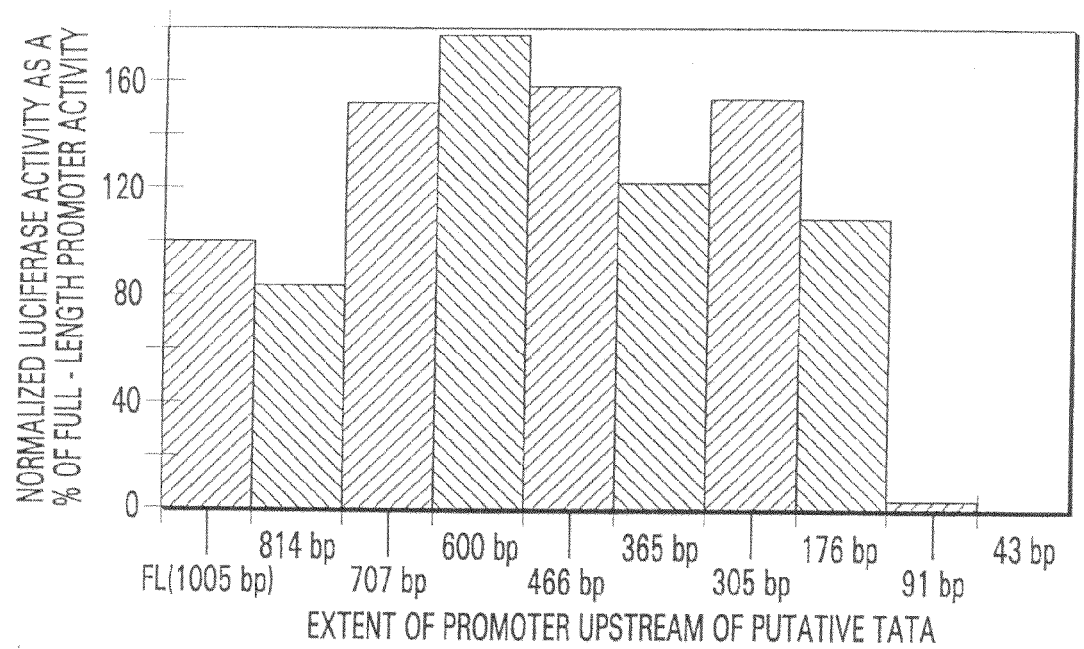
FIG. 9 is a bar graph showing luciferase activity after deletions of select regions of the Ms26 promoter.

The foregoing procedures were used to identify essential regions of the Ms26 promoter. After linking the promoter with the luciferase marker gene deletion analysis was performed on the regions of the promoter upstream of the putative TATA box, as represented in FIG. 9. The x-axis of the bar graph indicates the number of base pairs immediately upstream of the putative TATA box retained in a series of deletion derivatives starting from the 5' end of the promoter. The y-axis shows the normalized luciferase activity as a percent of full-length promoter activity.

As is evident from the graph, approximately 176 bp immediately upstream of the TATA box was sufficient, when coupled to the core promoter (putative TATA box through start of transcription), plus 5' nontranslated leader, for transient expression in anthers. By contrast, luciferase activity was minimal upon further deletion from the 5' end to 91 bp upstream of the putative TATA box. This 176 bp upstream of the putative TATA box through the nontranslated leader can be considered a minimal promoter, which is further represented at FIG. 10. The TATA box is underlined. Deletion within the full-length promoter from −176 through −92 relative to the TATA box reduced activity to about 1% of wild type. Deletion of −39 through −8 did not greatly reduce activity. Therefore the −176 to −44 bp region contains an essential region and thus would constitute an upstream enhancer element conferring anther expression on the promoter, which we refer to as an "anther box".

Figure 11:
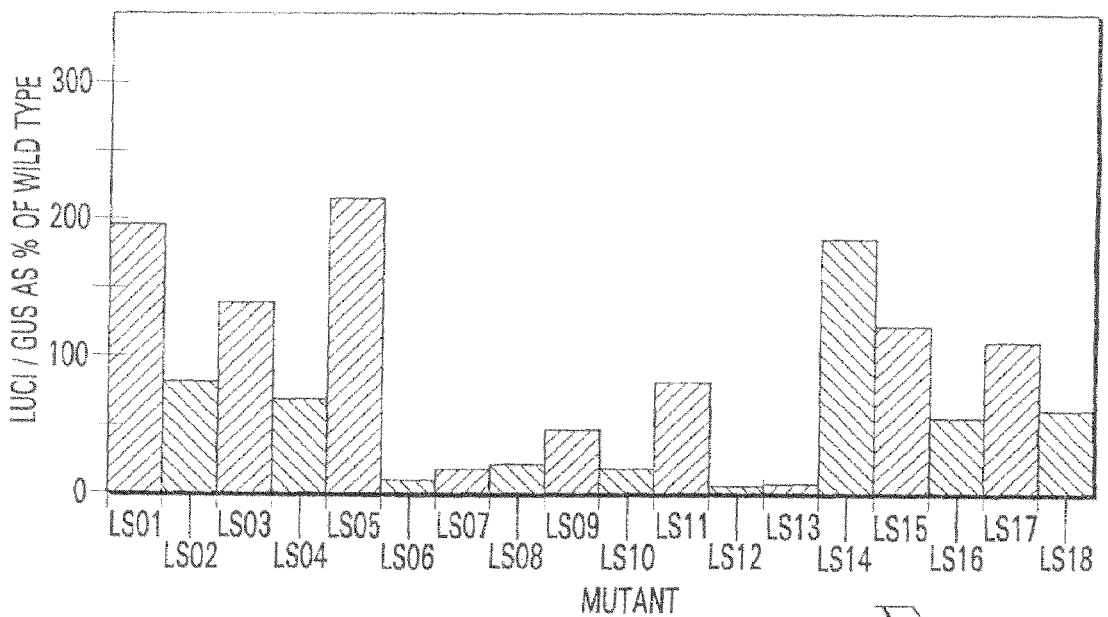
FIG. 11 is a bar graph showing luciferase activity after substitution by restriction site linker scanning of select small (9-10 bp) regions of the Ms26 essential promoter fragment.

Linker scanning analysis was conducted across the anther box in 9-10 bp increments. The locations of the linker scanning substitutions in this region are shown in FIG. 10, and the expression levels of the mutants relative to the wild type sequence are shown in FIG. 11. The most drastic effect on transient expression in anthers was observed for mutants LS12 and LS13, in the region 52-71 bp upstream of the putative TATA box. A major effect on transient expression in anthers was also observed for mutants LS06, LS07, LS08 and LS10, within the region 82-131 bp upstream of the putative TATA box. Sequences within the anther box required for wild type levels of transient expression in anthers are thus demonstrated in the −52 to −131 region relative to the putative TATA box, particularly the −52 to −71 region. The essential regions are shown at SEQ ID NO: 6 (FIG. 10) and, as compared to the genomic sequence, SEQ ID NO: 7 (FIG. 5) are bases 1-1088; 830-962; 830-914; 917-962; 875-954; 935-954; and 875-924.

EXAMPLE 7

Ms26 *Sorghum*, Rice and Maize Comparison

As noted above, Ms26 is a male fertility gene in maize. When it is mutated, and made homozygous recessive, male sterility will result. An orthologue of Ms26 was identified in *sorghum*. The *sorghum* orthologue of the Ms26 cDNA was isolated by using the maize Ms26 gene primers in a polymerase chain reaction with *sorghum* tassel cDNA as the template. The resultant cDNA fragment was sequenced by methods described supra and then compared to the Ms26 cDNA from maize. Nucleotide sequence comparisons are set forth in FIG. 12 and show 90% identity. An orthologue from rice was also identified and the predicted coding sequence (SEQ ID NO: 17) and protein (SEQ ID NO: 18) is set forth in FIG. 19. It has one intron less than the maize and *sorghum* Ms26, and the coding sequences are highly conserved.

Identification of the *sorghum* and rice promoters was accomplished. FIG. 20 shows an alignment of the Ms26 promoter of corn (SEQ ID NO: 5), *sorghum* (SEQ ID NO: 19) and rice (SEQ ID NO: 20). The last three bases of the corn promoter shown in the figure is the ATG start of translation.

Alignment as reflected in FIG. 21 of the maize Ms26 protein (SEQ ID NO: 2), rice Ms26 protein (SEQ ID NO: 18) and *sorghum* Ms26 protein (SEQ ID NO: 4), and a consensus sequence (SEQ ID NO: 21). The comparison of protein sequences shows the protein is highly conserved among the orthologues, with the rice protein sharing 92% similarity and 86% identity when compared to the maize orthologue. The predicted tissue specificity in rice and *sorghum* is further reflected in a comparison of the Ms26 protein in the *sorghum* and rice EST database derived from panicle (flower) libraries. *Sorghum* sequences producing significant alignments (GenBank accession numbers BI075441.1; BI075273.1; BI246000.1; BI246162.1; BG948686.1; BI099541.1 and BG948366.1, among others) all were sequences from immature panicle of *sorghum*, and sequences showing significant alignment in rice (GenBank accession numbers C73892.1; CR290740.1, among others) were also from rice immature panicle.

As is evident from the above, nucleotide sequences which map to the short arm of chromosome 1 of the *Zea mays* genome, at the same site as the Ms26 gene, ms26-m2::Mu8 and its alleles, are genes critical to male fertility in plants, that is, are necessary for fertility of a plant, or, when mutated from the sequence found in a fertile plant, cause sterility in the plant.

EXAMPLE 8

Figure 22:
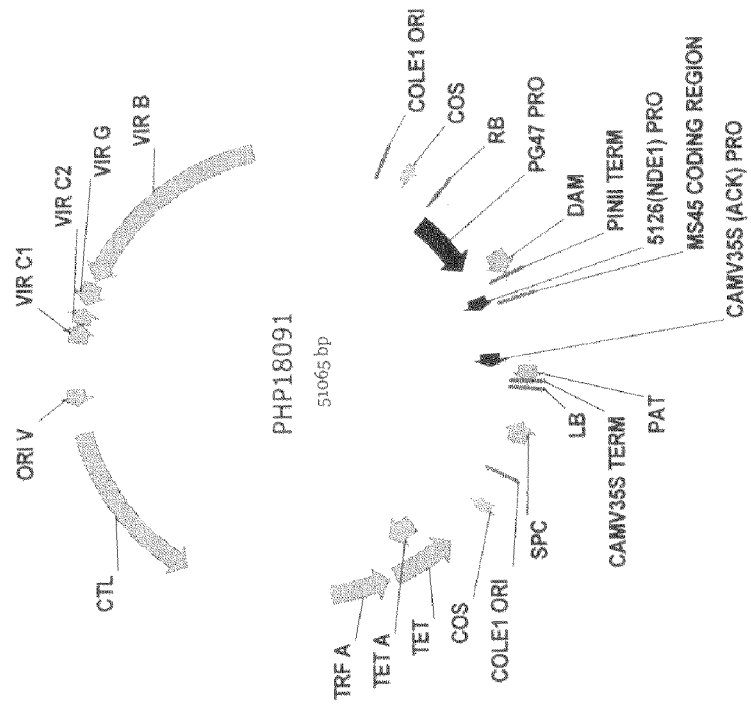
FIG. 22 is a plasmid map of PHP 18091, containing Ms45 fertility gene with a pollen promoter, cytotoxic gene and selectable marker.

Construction of a Plant Transformation Vector Comprising a Selectable Marker, a Male Fertility Gene Ms45 and a Pollen Cytotoxin Gene A construct designated PHP18091, shown in FIG. 22 is made by assembling following DNA components:
1. The plasmid pSB11 backbone DNA (pSB31 lacking the EcoRI fragment carrying the 35SGUS and 35SBAR genes, Ishida et al., *Nature Biotechnol*. (1996) 14:745-750). This DNA backbone contains T-DNA border sequences and the replication origin from pBR322.
2. The 35S:PAT gene which encodes the enzyme phosphinothricin acetyltransferase (PAT) from *Streptomyces viridochomagenes* (nucleotides 6-557 from accession number A02774, Strauch et al. 1988, EP 0275957-A) under the transcriptional control of the cauliflower mosaic virus (CaMV) 35S promoter and terminator (nucleotides 6906-7439, and 7439-7632, respectively from Franck et al. 1980, *Cell* 21: 285-294).

3. The 5126:Ms45 gene which contains the maize male fertility gene coding region (nucleotides 1392-3343, accession number AF360356, Albertsen et a *Am. J. Bot.* (1993) 80:16) under the control of the maize anther-specific promoter 5126 (nucleotides 985-1490, accession number 175204).

4. The PG47:DAM gene which contains the *E. coli* DNA (Adenosine-$N^6$) methyltransferase (DAM) coding region (nucleotides 195-1132, Brooks et al., *Nucleic. Acids Res* (1983) 11: 837-851) driven by the maize pollen-specific promoter PG47 (nucleotides 1-2870, accession number X66692, Allen and Lonsdale, *Plant J.* (1993) 3:261-271). The transcription of this gene is terminated by the potato proteinase inhibitor II (PinII) terminator (nucleotides 2-310, An et al., *Plant Cell* (1989) 1: 115-122).

5. A 3.34 kb NcoI DNA fragment containing Ms45:Ms45 was cloned upstream of the 35S:PAT gene in pUC8, creating PHP6641. A 4.7 kb HindIII/EcoRI DNA fragment containing Ms45:Ms45-35S:PAT from PHP6641 was cloned into pSB11, creating PHP10890 (Cigan et al, *Sex. Plant Reprod.* (2001) 14: 135-142). The native Ms45 promoter in PHP10890 was replaced by a 528 bp HindIII/NcoI fragment containing the maize 5126 promoter, creating PHP11943.

6. A 2.87 kb HindIII/NcoI fragment containing PG47 promoter was ligated with a 0.8 kb NcoI/HindIII fragment containing the DAM coding region, PinII terminator and 35S enhancer which was from PHP10404 (Unger, et al., *Transgenic Res.* (2001) 10: 409-422), creating a 3.67 kb fragment HindIII fragment containing PG47:DAM gene fusion (with the 35S enhancer). This 3.67 kbp HindIII fragment was then cloned into the HindIII site of PHP11943, creating PHP20005. The 35S enhancer in PHP20005 was removed, creating PHP18071. The PHP18071 was introduced into *Agrobacterium* strain LBA4404 carrying plasmid pSB1 by triparental mating (Ishida et al., *Nature Biotechnol.* (1996) 14:745-750). The co-integrate of PHP18071 and pSB1 was named PHP18091.

EXAMPLE 9

Transformation of Corn with the Restoring Transgene Construct of Example 8

A male-sterile female which was homozygous for an ms45 mutant Ac excision allele, ms45'-9301 (ms45) was repeatedly crossed with bulked pollen from maize Hi-type II plants (Armstrong 1994, In: Freeling and Walbot (eds). *The Maize Handbook*. Springer, New York, pp 663-671) resulting in the introgression of this ms45 allele in transformation amenable maize germplasm over multiple generations. The resultant source of material for transformation consisted of embryos segregating (1:1 or 3:1) for ms45 and allowed for both transformation directly into a homozygous ms45 background and to test the genetic complementation of the ms45 mutation in $T_0$ plants. *Agrobacterum*-mediated transformation was performed according to Zhao et al. 1999, (U.S. Pat. No. 5,981, 840). Genotyping and molecular analysis (integration and PTU) of transformants were done according Cigan et al., (*Sex. Plant. Reprod.* (2001) 14:135-142). Transformants with single-integration and complete PTU were selected for further studies.

EXAMPLE 10

Analysis of Maize Transformants

Transgenic plants ($T_0$) from Example 9 were evaluated for the whole plant morphology and analyzed for transgene transmission through both pollen and egg cells. No morphological difference was observed between the transgenic plants and the non-transgenic control plants except for the degree of male fertility. Transformants with single-integration and intact PTU were partial male fertile while non-transgenic control plants were completely male sterile, indicating that the expression of Ms45 gene complemented the homozygous recessive ms45 male sterile phenotype. This also demonstrated that the expression of the DAM gene caused partial male sterility by eliminating the pollen grains carrying the transgenes. Without the DAM gene, Ms45 transgene can completely recover the ms45 male sterile mutation (Cigan et al., *Sex. Plant. Reprod.* (2001) 14: 135-142). The correct function of DAM gene was further determined by controlled pollinations between $T_0$ transgenic plants and non-transgenic plants. Pollen grains from $T_0$ transgenic plants were used to pollinate non-transgenic plants control plants. Immature embryos were harvested from ears of these non-transgenic plants 18 days after pollination and cultured either on MS media or MS media containing 3.0 mg/L of bialaphos (Murashige, T. and Skoog, F. A revised medium for rapid growth and bioassays with tobacco tissue cultures. *Physiol. Plant* (1962) 15: 437-439). 100% of the embryos were able to germinate on control medium while none of the embryos were able to germinate on media containing 3 mg/L of bialaphos, indicating that the restoring transgene construct was not transmitted through pollen to progeny.

In addition, pollen from non-transgenic plants was used to pollinate the $T_0$ transgenic maintainer plants. Immature embryos were harvested from ears of these $T_0$ transgenic maintainer plants 18 days after pollination and cultured as above control media or media containing 3 mg/L of bialaphos. All embryos were able to germinate on control medium while 50% of the embryos were able to germinate on the medium containing bialaphos, indicating that the restoring transgene construct was transmitted through the ovule to progeny at the expected frequency. The results of embryo rescues are summarized in Tables 1 and 2.

TABLE 1

Transgene transmission through pollen

| | Pollen to non-transgenic plants | | | | | |
|---|---|---|---|---|---|---|
| | Control medium | | | Medium + 3 mg/l bialaphos | | |
| Transgenic plants | # embryo cultured | # embryo germinated | % | # embryo cultured | # embryo germinated | % |
| 14089263 | 40 | 40 | 100 | 60 | 0 | 0 |
| 14089277 | 100 | 100 | 100 | 100 | 0 | 0 |
| 14089839 | 40 | 40 | 100 | 60 | 0 | 0 |

TABLE 2

Transgene transmission through egg cells

Pollen from non-transgenic plants
Medium + 3 mg/l bialaphos

| Transgenic plants | # embryo cultured | # embryo germinated | % |
|---|---|---|---|
| 14089262 | 20 | 8 | 40 |
| 14089277 | 40 | 22 | 55 |
| 14089839 | 40 | 21 | 53 |

EXAMPLE 11

Conversion of $T_0$ Plants into Different Inbred Lines and Analysis of Tn Plants To transgenic maintainer plants from Example 9 were converted into different inbred backgrounds through repeated backcross by pollination from inbred lines such as PH09B. To accomplish this, pollen produced by PH09B that is ms45 heterozygous background were used to pollinate the ears of $T_0$ maintainer plants that were homozygous for the ms45 mutant alleles. $T_1$ seed harvested from these $T_0$ plants segregated for both transgenes and ms45 alleles. $T_1$ plants that did not contain the restoring transgene construct were eliminated by herbicide selection. $T_1$ plants containing transgenes were analyzed for ms45 background and male fertility according to Cigan et al., (*Sex. Plant. Reprod.*, (2001) 14: 135-142). In general, $T_1$ plants in homozygous ms45 condition that contained the restoring transgene construct showed partial male fertility like that observed for the $T_0$ parent plants, while the $T_1$ plants in homozygous ms45 condition but containing no transgenes were complete male sterile. This suggested that the Ms45 transgene continued to function correctly in a different genetic background. Pollen grains from $T_1$ plants were examined for viability using microscopic and histochemical staining. Pollen grains at different developmental stages were collected and stained with fluorescein diacetate (FDA), 4', 6-diamidino-2-phenylindole (DAPI) and ethidium bromide (EB). About 50% of the pollen grains from the transgenic $T_1$ plants lost their viability as judged by the absence of fluorescence after staining with FDA after first pollen mitosis, while the pollen grains from non-transgenic control plants showed uniform FDA staining. This was further supported by in vitro pollen germination studies. The germination rate of the pollen grains from the transgenic $T_1$ plants were about half of that from non-transgenic control plants. Pollen grains from transgenic $T_1$ plant were also used to pollinate non-transgenic plants to test transgene transmission thought pollen. For instance, none of 248 embryos from a non-transgenic plant pollinated by a $T_1$ plant (20118954) were able to germinate on the medium containing 3 mg/l bialaphos. These experiments confirmed both the correct function of the Ms45 and DAM transgenes in different genetic backgrounds. The $T_1$ plants with desired performance were used for the next backcross iteration using pollen from the paternal inbred parent which was heterozygous for the mutant ms45 allele. This process will be repeated until sixth generation.

EXAMPLE 12

Large Scale Transmission and Maintenance of ms45 Male Sterility Using the Construct of Example 8

$T_1$ plants derived from $T_0$ 14089277 as described in example 9 were used as males to pollinate either wild type inbred plants or ms45/ms45 male sterile inbred plants. The 10,117 $T_2$ progeny from the wild type crosses and 6688 $T_2$ progeny from the ms45/ms45 crosses were evaluated for transgene transmission by screening for herbicide resistance. For both types of crosses a total of 16786 $T_2$ plants were found to be herbicide sensitive, yielding a non-transmission frequency of 99.89%. All $T_2$ plants from the ms45/ms45 crosses that did not contain the transgene, were completely male sterile, indicating that this transgenic line can maintain ms45 sterility.

EXAMPLE 13

Figure 23:
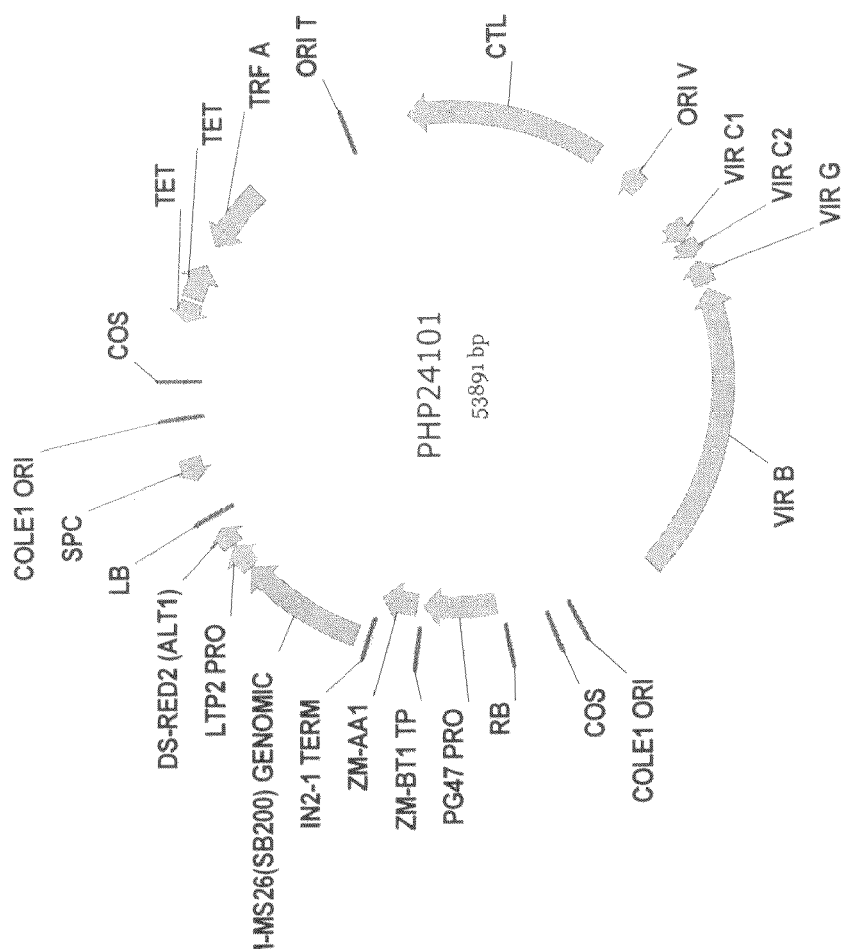
FIG. 23 is a plasmid map of PHP 24101, containing the Ms26 fertility gene with a pollen promoter, cytotoxic gene and selectable marker.

Construction of a Plant Transformation Vector Comprising a Screenable Marker, a Male Fertility Gene Ms26 and a Pollen Cytotoxin Gene A construct designated PHP24101, shown in FIG. 23, is made by assembling following DNA components:

1. The plasmid pSB11 backbone DNA (pSB31 lacking the EcoRI fragment carrying the 35SGUS and 35SBAR genes, Ishida et al., *Nature Biotechnol*. (1996) 14:745-750). This DNA backbone contains T-DNA border sequences and the replication origin from pBR322.
2. The PG47PRO:ZM-AA1 gene which contains alpha-amylase 1 coding region from *Zea mays* as set forth in FIG. 24. (SEQ ID NO: 26). The transcription of this gene is terminated by IN2-1 terminator (U.S. Pat. No. 5,364,780).
3. The Ms26 (SB200) GENOMIC gene (SEQ ID NO: 7) which contains the maize male fertility gene coding region.
4. LTP2:DS-RED2 (ALT1) which contains red florescence coding region (a variant of *Discosoma* sp. red fluorescent protein (DsRed), from Clontech mutated to remove BstEII site, codon sequence unchanged) driven by LTP2 promoter, supra.
5. A 2.143 kb EcoRV/DraI DNA fragment containing LTP2PRO:DS-RED2 (ALT1) from PHP21737 was cloned into downstream of the Ms26 GENOMIC gene in SK vector, creating SK-Ms26 GENOMIC-LTP2PRO:DS-RED2 (ALT1).
6. A 2.143 kb EcoRV/DraI DNA fragment containing LTP2PRO:DS-RED2 (ALT1) from PHP21737 was cloned into downstream of the Ms45PRO:Ms45 GENOMIC gene in SK vector, creating SK-Ms45-LTP2PRO:DS-RED2 (ALT1).
7. A 5.429 kb NotI fragment containing 5126PRO:Ms45 GENOMIC-UBI:MOPAT:PINII in PHP20532 was replaced by A 4.318 kb NotI fragment containing Ms45-LTP2PRO:DS-RED2 (ALT1) from SK-Ms45-LTP2PRO:DS-RED2 (ALT1), creating PHP22623.
8. A 4.318 kb NotI fragment containing Ms45-LTP2PRO:DS-RED2 (ALT1) in PHP22623 was replaced by A 5.960 kb NotI DNA fragment containing Ms26 GENOMIC-LTP2PRO:DS-RED2(ALT1) from SK-Ms26 GENOMIC-LTP2PRO:DS-RED2 (ALT1), creating PHP24014. The PHP24014 was introduced into *Agrobacterium* strain LBA4404 carrying plasmid pSB1 by Electrophoresis. Cointegrate of PHPPHP24014 and pSB1 was named PHP24101.

EXAMPLE 14

Transformation of Corn with the Restoring Transgene Construct of Example 13

A male-sterile female which was homozygous for a ms26 mutant excision allele, (ms26) was repeatedly crossed with bulked pollen from maize Hi-type II plants (Armstrong 1994, In: Freeling and Walbot (eds). *The Maize Handbook*. Springer, New York, pp 663-671) resulting in the introgression of this ms26 allele in transformation amenable maize germplasm over multiple generations. The resultant source of material for transformation consisted of embryos segregating (1:1 or 3:1) for ms26 and allowed for both transformation directly into a homozygous ms26 background and to test the genetic complementation of the ms26 mutation in $T_0$ plants. *Agrobacterum*-mediated transformation was performed according to Zhao et al. 1999, (U.S. Pat. No. 5,981,840). Genotyping and molecular analysis (integration and PTU) of transformants were done according Cigan et al., (*Sex. Plant. Reprod.* 1 (2001) 4:135-142). Transformants with single-integration and complete PTU were selected for further studies.

EXAMPLE 15

Analysis of Maize Transformants

Transgenic plants ($T_0$) from Example 14 were evaluated for the whole plant morphology and analyzed for transgene transmission through pollen. No morphological difference was observed between the transgenic plants and the non-transgenic control plants except for the degree of male fertility. Transformants with single-integration and intact PTU were partial male fertile while non-transgenic control plants were completely male sterile, indicating that the expression of the Ms26 gene complemented the homozygous recessive ms26 male sterile phenotype. This also suggested that the pollen expression of the alpha amylase (AA) gene caused partial male sterility by disrupting the normal function of the pollen grains carrying the transgenes. Staining pollen from transformants with potassium iodide (KI), which stains starch granules, showed that approximately half of the pollen grains contained starch (black grains, non-transgenic) and the other half did not contain starch (gold grains, transgenic). The correct function of AA gene was further determined by controlled pollinations between $T_0$ transgenic plants and non-transgenic plants. Resultant $T_1$ kernels were evaluated for a red fluorescence phenotype. If the transgenes were transmitted through the pollen then the $T_1$ seed would contain red fluorescent kernels due to the expression of RFP in the aleurone layer. For four independent events shown in Table 3, no RFP expression was found in the $T_1$ seed, whereas seed from the $T_0$ ears themselves ($T_1$ seed) contained approximately 50% red fluorescent kernels.

TABLE 3

Transgene transmission through pollen

| | Pollen to non-transgenic plants Kernel Red Fluoresence | | |
|---|---|---|---|
| Transgenic plants | # Yellow Kernels | # Red Kernels | % |
| 42772379 | 338 | 0 | 100 |
| 42772385 | 277 | 0 | 100 |
| 42772400 | 268 | 0 | 100 |
| 42772411 | 598 | 0 | 100 |

Thus it can be seen that the invention achieves at least all of its objectives.

What is claimed is:

1. A method of maintaining a homozygous recessive condition of a male sterile plant, the method comprising:
   (a) providing a first plant comprising homozygous recessive alleles of the Ms26 gene wherein said plant is male sterile,
   (b) introducing a construct into a second plant, the second plant comprising homozygous recessive alleles of the Ms26 gene, the construct in the hemizygous condition, the construct comprising:
      (i) a first nucleotide sequence comprising the Ms26 nucleotide sequence, wherein said first nucleotide sequence is selected from the group consisting of
         a) a sequence encoding the amino acid sequence of SEQ ID NO: 2;
         b) the nucleotide sequence of SEQ ID NO: 1;
         c) nucleotides 1089-3897 of SEQ ID NO: 7;
         d) a sequence having at least 90% identity to SEQ ID NO: 1, or to nucleotides 1089-3897 of SEQ ID NO: 7, over the full length of each of said sequences;
         e) a sequence having at least 95% identity to SEQ ID NO: 1, or to nucleotides 1089-3897 of SEQ ID NO: 7, over the full length of each of said sequences; and
         f) a sequence which hybridizes to the full length of either SEQ ID NO: 1 or nucleotides 1089-3897 of SEQ ID NO: 7, under highly stringent conditions of a wash of 0.1 SSC, 0.1% (w/v) SDS at 65° C.,
      that when expressed in the first plant would restore male fertility;
      (ii) a second nucleotide sequence that when expressed inhibits the function or formation of viable male gametes in the second plant, such that viable male gametes are produced in the second plant, wherein said viable male gametes contain the recessive alleles of Ms26 and do not contain the construct; and (c) fertilizing the first plant with the male gametes of the second plant to produce progeny which maintain the homozygous recessive condition of the first plant.

2. The method of claim 1, wherein the first nucleotide sequence is operably linked to a third nucleotide sequence directing expression preferentially to male plant cells.

3. The method of claim 2, wherein the third nucleotide sequence functions only in the presence of an inducing substance or condition.

4. The method of claim 2, wherein the third nucleotide sequence is selected from the group consisting of the male tissue regulatory sequence of the 5126, Ms26 and Ms45 genes.

5. The method of claim 1, wherein the second nucleotide sequence is operably linked to a fourth nucleotide sequence, the fourth nucleotide sequence directing expression preferentially to male gametes.

6. The method of claim 1, wherein the second nucleotide sequence is selected from the group consisting of the nucleotide sequence of the DAM methylase gene, Zea mays alpha amylase gene, and a cytotoxin encoding gene.

7. The method of claim 6, wherein the second sequence is operably linked to a fourth nucleotide sequence directing expression to male gametes.

8. The method of claim 5, wherein the fourth nucleotide sequence is selected from the group consisting of the regulatory region of the polygalacturonase 47 gene, Zm13 gene, pectin methylesterase gene, calmodulin binding protein gene, actin depolymerizing factor gene, profilin gene, and sulphated pentapeptide phytosulphokine gene.

9. The method of claim 1, further comprising a fifth nucleotide sequence encoding a product, the expression of which is capable of being used for selection of plant cells having the construct.

10. The method of claim 9 wherein the fifth nucleotide sequence is selected from the group consisting of red fluorescent gene, cyan fluorescent protein gene, yellow fluorescent protein gene, luciferase gene, green fluorescent protein gene, anthocyanin pI gene and phosphinothricin acetyltransferase encoding gene.

11. The method of claim 9 wherein the fifth nucleotide sequence is operably linked to a regulatory region selected from the group consisting of the lipid transfer protein (LTP2) gene, the polygalacturonase 47 gene, Zm13 gene, pectin methylesterase gene, calmodulin binding protein gene, actin depolymerizing factor gene, profilin gene, and sulphated pentapeptide phytosulphokine gene.

12. The method of claim 1, further comprising selecting for said second plant by identifying plants having said construct.

13. A method of maintaining a homozygous recessive condition of a first plant when crossing the first plant to a second plant, the method comprising:

(a) providing a first plant comprising homozygous recessive alleles of the Ms26 gene, the expression of which results in male sterility;

(b) introducing a construct into a second plant, the second plant comprising homozygous recessive alleles of the Ms26 gene, the construct in a hemizygous condition comprising:

(i) a first nucleotide sequence comprising the Ms26 nucleotide sequence, that when expressed in the first plant would restore male fertility, said first nucleotide sequence selected from the group consisting of a) a sequence encoding the amino acid sequence of SEQ ID NO: 2,
b) the nucleotide sequence of SEQ ID NO: 1;
c) nucleotides 1089-3897 of SEQ ID NO: 7;
d) a sequence having at least 90% identity to SEQ ID NO: 1, or to nucleotides 1089-3897 of SEQ ID NO: 7, over the full length of each of said sequences;
e) a sequence having at least 95% identity to SEQ ID NO: 1, or to nucleotides 1089-3897 of SEQ ID NO: 7, over the full length of each of said sequences; and
f) a sequence which hybridizes to the full length of either SEQ ID NO: 1 or nucleotides 1089-3897 of SEQ ID NO: 7, under highly stringent conditions of a wash of 0.1 SSC, 0.1% (w/v) SDS at 65° C., (ii) a second nucleotide sequence selected from the group consisting of the sequence of the DAM methylase gene, Zea mays alpha amylase gene, and a cytotoxin encoding gene;

(iii) a third nucleotide sequence operably linked to the first nucleotide sequence, selected from the group consisting of the male tissue regulatory region of the 5126, Ms26 and Ms45 genes, directing expression preferentially to male plant tissue;

(iv) a fourth nucleotide sequence operably linked to the second nucleotide sequence directing expression to plant male gametes, such that viable male gametes are produced in the second plant, wherein said viable male gametes contain the recessive alleles and do not contain the construct; and (c) fertilizing the first plant with the male gametes of the second plant to produce progeny which is male sterile and maintain the homozygous recessive condition of the first plant.

14. The method of claim 13, further comprising a fifth nucleotide sequence encoding a product capable of being used for selection of plant cells containing the construct.

15. The method of claim 14 wherein the fifth nucleotide sequence is selected from the group consisting of red fluorescent gene, cyan fluorescent protein gene, yellow fluorescent protein gene, luciferase gene, green fluorescent protein gene, anthocyanin pI gene and phosphinothricin acetyltransferase encoding gene.

16. The method of claim 14 wherein the fifth nucleotide sequence is operably linked to a regulatory region selected from the group consisting of the LTP2 gene, the polygalacturonase 47 gene, Zm13 gene, pectin methylesterase gene, calmodulin binding protein gene, actin depolymerizing factor gene, profilin gene, and sulphated pentapeptide phytosulphokine gene.

17. The method of claim 1 wherein the first nucleotide sequence is selected from the group consisting of (a) a sequence encoding the amino acid sequence of SEQ ID NO: 2;
(b) the sequence of SEQ ID NO: 1; and
(c) nucleotides 1089-3897 of SEQ ID NO: 7.

18. The method of claim 17, wherein the first nucleotide sequence is operably linked to a third nucleotide sequence directing expression preferentially to male plant cells.

19. The method of claim 18, wherein the third nucleotide sequence functions only in the presence of an inducing substance or condition.

20. The method of claim 18, wherein the third nucleotide sequence is selected from the group consisting of the male tissue regulatory sequence of the 5126, Ms26 and Ms45 genes.

21. The method of claim 17, wherein the second nucleotide sequence is linked to a fourth nucleotide sequence, the fourth nucleotide sequence directing expression preferentially to male gametes.

22. The method of claim 17, wherein the second nucleotide sequence is selected from the group consisting of the nucleotide sequence of the DAM methylase gene, *Zea mays* alpha amylase gene, and a cytotoxin encoding gene.

23. The method of claim 22, wherein the second sequence is operably linked to a fourth nucleotide sequence directing expression preferentially to plant male gametes.

24. The method of claim 21, wherein the fourth nucleotide sequence is selected from the group consisting of the regulatory region of the polygalacturonase 47 gene, Zm13 gene, pectin methylesterase gene, calmodulin binding protein gene, actin depolymerizing factor gene, profilin gene, and sulphated pentapeptide phytosulphokine gene.

25. The method of claim 17, further comprising a fifth nucleotide sequence encoding a product capable of being used for selection of plant cells having the construct.

26. The method of claim 25 wherein the fifth nucleotide sequence is selected from the group consisting of red fluorescent gene, cyan fluorescent protein gene, yellow fluorescent protein gene, luciferase gene, green fluorescent protein gene, anthocyanin p1 gene and phosphinothricin acetyltransferase encoding gene.

27. The method of claim 25 wherein the fifth nucleotide sequence is operably linked to a regulatory region selected from the group consisting of the LTP2 gene, the polygalacturonase 47 gene, Zm13 gene, pectin methylesterase gene, calmodulin binding protein gene, actin depolymerizing factor gene, profilin gene, and sulphated pentapeptide phytosulphokine gene.

28. The method of claim 17 further comprising selecting for said second plant by identifying plants having said construct.

29. A method of producing seed from a plant having female and male gametes, the method comprising:
  (a) introducing into a male sterile plant comprising homozygous recessive alleles of the Ms26 gene, a construct in the hemizygous condition comprising:
    (i) a first nucleotide sequence comprising the Ms26 nucleotide sequence, wherein said first nucleotide sequence is selected from the group consisting of
      a) a sequence encoding the amino acid sequence of SEQ ID NO: 2;
      b) the nucleotide sequence of SEQ ID NO: 1;
      c) nucleotides 1089-3897 of SEQ ID NO: 7;
      d) a sequence having at least 90% identity to SEQ ID NO: 1, or to nucleotides 1089-3897 of SEQ ID NO: 7, over the full length of each of said sequences;
      e) a sequence having at least 95% identity to SEQ ID NO: 1, or to nucleotides 1089-3897 of SEQ ID NO: 7, over the full length of each of said sequences; and
      f) a sequence which hybridizes to the full length of either SEQ ID NO: 1 or nucleotides 1089-3897 of SEQ ID NO: 7, under highly stringent conditions of a wash of 0.1 SSC, 0.1% (w/v) SDS at 65° C.,
    (ii) a second nucleotide sequence, that when expressed inhibits the function or formation of male gametes in the plant, such that viable male gametes are produced wherein said viable male gametes do not contain the construct;
  (b) self fertilizing the plant; and
  (c) producing seed which contain the construct.

30. The method of claim 29, wherein the first nucleotide sequence is operably linked to a third nucleotide sequence directing expression preferentially to male plant cells.

31. The method of claim 29, wherein the second nucleotide sequence is operably linked to a fourth nucleotide sequence, the fourth nucleotide sequence directing expression preferentially to male gametes.

32. The method of claim 29, further comprising a fifth nucleotide sequence encoding a product capable of being used for selection of plant cells containing the construct.

33. The method of claim 29, further comprising identifying plants having said construct.

34. The method of claim 29 wherein the first nucleotide sequence is selected from the group consisting of
  a) a sequence encoding the amino acid sequence of SEQ ID NO: 2
  b) the sequence of SEQ ID NO: 1; and
  c) nucleotides 1089-3897 of SEQ ID NO: 7.

35. The method of claim 2 wherein the third nucleotide sequence is selected from the group consisting of
  (a) SEQ ID NO: 5;
  (b) SEQ ID NO: 6;
  (c) bases 1-1088 of SEQ ID NO: 7;
  (d) bases 830 to 962 of SEQ ID NO: 7;
  (e) bases 830 to 914 of SEQ ID NO: 7;
  (f) bases 917 to 962 of SEQ ID NO: 7;
  (g) bases 875 to 954 of SEQ ID NO: 7;
  (h) bases 935 to 954 of SEQ ID NO: 7;
  (i) bases 875 to 924 of SEQ ID NO: 7; and
  (j) a functional fragment of any of the foregoing sequences which functional fragment is essential for male tissue-preferred expression of a linked sequence.

36. The method of claim 35, wherein the second nucleotide sequence is operably linked to a fourth nucleotide sequence, the fourth nucleotide sequence directing expression preferentially to male gametes.

37. The method of claim 35, wherein the second nucleotide sequence is selected from the group consisting of the nucleotide sequence of the DAM methylase gene, *Zea mays* alpha amylase gene, and a cytotoxin encoding gene.

38. The method of claim 35 wherein the second sequence is operably linked to a fourth nucleotide sequence directing expression to plant male gametes.

39. The method of claim 36, wherein the fourth nucleotide sequence is selected from the group consisting of the regulatory region of the polygalacturonase 47 gene, Zm13 gene, pectin methylesterase gene, calmodulin binding protein gene, actin depolymerizing factor gene, profilin gene, and sulphated pentapeptide phytosulphokine gene.

40. The method of claim 35, further comprising a fifth nucleotide sequence encoding a product capable of being used for selection of plant cells having the construct.

41. The method of claim 35, further comprising selecting for said second plant by identifying plants having said construct.

42. The method of claim 30 wherein the third nucleotide sequence is selected from the group consisting of
  (a) SEQ ID NO: 5;
  (b) SEQ ID NO: 6;
  (c) bases 1-1088 of SEQ ID NO: 7;
  (d) bases 830 to 962 of SEQ ID NO: 7;
  (e) bases 830 to 914 of SEQ ID NO: 7;
  (f) bases 917 to 962 of SEQ ID NO: 7;
  (g) bases 875 to 954 of SEQ ID NO: 7;
  (h) bases 935 to 954 of SEQ ID NO: 7;
  (i) bases 875 to 924 of SEQ ID NO: 7;

(j) a functional fragment of any of the foregoing sequences, which functional fragment is essential for male tissue-preferred expression of a linked sequence, such that viable gametes are produced in the first plant that do not contain the construct.

43. The method of claim 42, wherein the second nucleotide sequence is operably linked to a fourth nucleotide sequence, the fourth nucleotide sequence directing expression preferentially to male gametes.

44. The method of claim 42, further comprising a fifth nucleotide sequence encoding a product capable of being used for selection of plant cells having the construct.

45. The method of claim 42, further comprising identifying plants having said construct.

46. A method of restoring male fertility in a male sterile plant, the male sterile plant comprising homozygous recessive alleles of a gene critical to male fertility, the method comprising introducing into said plant a nucleotide sequence that is the functional complement of the homozygous recessive condition, wherein the nucleotide sequence is selected from the group consisting of a) a sequence encoding the amino acid sequence of SEQ ID NO: 2, b) the nucleotide sequence of SEQ ID NO: 1;

c) nucleotides 1089-3897 of SEQ ID NO: 7;

d) a sequence having at least 90% identity to SEQ ID NO: 1, or nucleotides 1089-3897 of SEQ ID NO: 7 over the full length of said sequence;

e) a sequence having at least 95% identity to SEQ ID NO: 1, or nucleotides 1089-3897 of SEQ ID NO: 7 over the full length of said sequence; and f) a sequence which hybridizes to SEQ ID NO: 1 or nucleotides 1089-3897 of SEQ ID NO: 7 under highly stringent conditions of a wash of 0.1 SSC, 0.1% (w/v) SDS at 65° C.

47. The method of claim 46, wherein said nucleotide sequence is selected from the group consisting of a sequence encoding SEQ ID NO:2, the nucleotide sequence of SEQ ID NO:1 and nucleotides 1089-3897 of SEQ ID NO:7.

48. The method of claim 13, wherein said first nucleotide sequence is selected from the group consisting of a sequence encoding SEQ ID NO: 2, the nucleotide sequence of SEQ ID NO: 1 and nucleotides 1089-3897 of SEQ ID NO: 7.

* * * * *

SEQUENCE LISTING

```
<160> NUMBER OF SEQ ID NOS: 36

<210> SEQ ID NO 1
<211> LENGTH: 1906
<212> TYPE: DNA
<213> ORGANISM: Zea mays
<220> FEATURE:
<221> NAME/KEY: CDS
<222> LOCATION: (1)..(1638)
<220> FEATURE:
<221> NAME/KEY: CDS
<222> LOCATION: (1642)..(1767)

<400> SEQUENCE: 1 gaa ttc ggc acg agg gaa gct cac ctc acg ccg gcg acg cca tcg cca      48
Glu Phe Gly Thr Arg Glu Ala His Leu Thr Pro Ala Thr Pro Ser Pro
  1               5                  10                  15 ttc ttc cca cta gca ggg cct cac aag tac atc gcg ctc ctt ctg gtt      96
Phe Phe Pro Leu Ala Gly Pro His Lys Tyr Ile Ala Leu Leu Leu Val
             20                  25                  30 gtc ctc tca tgg atc ctg gtc cag agg tgg agc ctg agg aag cag aaa     144
Val Leu Ser Trp Ile Leu Val Gln Arg Trp Ser Leu Arg Lys Gln Lys
         35                  40                  45 ggc ccg aga tca tgg cca gtc atc ggc gca acg gtg gag cag ctg agg     192
Gly Pro Arg Ser Trp Pro Val Ile Gly Ala Thr Val Glu Gln Leu Arg
     50                  55                  60
```

-continued

```
              50                  55                  60
aac tac cac cgg atg cac gac tgg ctt gtc ggg tac ctg tca cgg cac      240
Asn Tyr His Arg Met His Asp Trp Leu Val Gly Tyr Leu Ser Arg His
 65                  70                  75                  80 agg aca gtg acc gtc gac atg ccg ttc act tcc tac acc tac atc gct      288
Arg Thr Val Thr Val Asp Met Pro Phe Thr Ser Tyr Thr Tyr Ile Ala
                     85                  90                  95 gac ccg gtg aat gtc gag cat gtc ctc aag act aac ttc acc aat tac      336
Asp Pro Val Asn Val Glu His Val Leu Lys Thr Asn Phe Thr Asn Tyr
            100                 105                 110 ccc aag gga atc gtg tac aga tcc tac atg gac gtg ctc ctc ggt gac      384
Pro Lys Gly Ile Val Tyr Arg Ser Tyr Met Asp Val Leu Leu Gly Asp
            115                 120                 125 ggc atc ttc aac gcc gac ggc gag ctg tgg agg aag cag agg aag acg      432
Gly Ile Phe Asn Ala Asp Gly Glu Leu Trp Arg Lys Gln Arg Lys Thr
        130                 135                 140 gcg agt ttc gag ttc gcc tcc aag aac ctg agg gat ttc agc gcc att      480
Ala Ser Phe Glu Phe Ala Ser Lys Asn Leu Arg Asp Phe Ser Ala Ile
145                 150                 155                 160 gtg ttc aga gag tac tcc ctg aag ctg tcg ggt ata ctg agc cag gca      528
Val Phe Arg Glu Tyr Ser Leu Lys Leu Ser Gly Ile Leu Ser Gln Ala
                165                 170                 175 tcc aag gca ggc aaa gtt gtg gac atg cag gaa ctt tac atg agg atg      576
Ser Lys Ala Gly Lys Val Val Asp Met Gln Glu Leu Tyr Met Arg Met
            180                 185                 190 acg ctg gac tcc atc tgc aag gtt ggg ttc ggg gtc gag atc ggc acg      624
Thr Leu Asp Ser Ile Cys Lys Val Gly Phe Gly Val Glu Ile Gly Thr
            195                 200                 205 ctg tcg cca gat ctc ccc gag aac agc ttc gcg cag gcg ttc gat gcc      672
Leu Ser Pro Asp Leu Pro Glu Asn Ser Phe Ala Gln Ala Phe Asp Ala
        210                 215                 220 gcc aac atc atc atc acg ctg cgg ttc atc gac ccg ctg tgg cgc atc      720
Ala Asn Ile Ile Ile Thr Leu Arg Phe Ile Asp Pro Leu Trp Arg Ile
225                 230                 235                 240 aag agg ttc ttc cac gtc ggg tca gag gcc ctc cta gcg cag agc atc      768
Lys Arg Phe Phe His Val Gly Ser Glu Ala Leu Leu Ala Gln Ser Ile
                245                 250                 255 aag ctc gtg gac gag ttc acc tac agc gtg atc cgc cgg agg aag gcc      816
Lys Leu Val Asp Glu Phe Thr Tyr Ser Val Ile Arg Arg Arg Lys Ala
            260                 265                 270 gag atc gtc gag gtc cgg gcc agc ggc aaa cag gag aag atg aag cac      864
Glu Ile Val Glu Val Arg Ala Ser Gly Lys Gln Glu Lys Met Lys His
            275                 280                 285 gac atc ctg tca cgg ttc atc gag ctg ggc gag gcc ggc gac gac ggc      912
Asp Ile Leu Ser Arg Phe Ile Glu Leu Gly Glu Ala Gly Asp Asp Gly
        290                 295                 300 ggc ggc ttc ggg gac gat aag agc ctc cgg gac gtg gtg ctc aac ttc      960
Gly Gly Phe Gly Asp Asp Lys Ser Leu Arg Asp Val Val Leu Asn Phe
305                 310                 315                 320 gtg atc gcc ggg cgg gac acg acg gcg acg acg ctg tcg tgg ttc acg     1008
Val Ile Ala Gly Arg Asp Thr Thr Ala Thr Thr Leu Ser Trp Phe Thr
                325                 330                 335 cac atg gcc atg tcc cac ccg gac gtg gcc gag aag ctg cgc cgc gag     1056
His Met Ala Met Ser His Pro Asp Val Ala Glu Lys Leu Arg Arg Glu
            340                 345                 350 ctg tgc gcg ttc gag gcg gag cgc gcg cgc gag gag ggc gtc acg ctc     1104
Leu Cys Ala Phe Glu Ala Glu Arg Ala Arg Glu Glu Gly Val Thr Leu
        355                 360                 365 gtg ctc tgc ggc ggc gct gac gcc gac gac aag gcg ttc gcc gcc cgc     1152
```

```
Val Leu Cys Gly Gly Ala Asp Ala Asp Lys Ala Phe Ala Ala Arg
        370                 375                 380 gtg gcg cag ttc gcg ggc ctc ctc acc tac gac agc ctc ggc aag ctg      1200
Val Ala Gln Phe Ala Gly Leu Leu Thr Tyr Asp Ser Leu Gly Lys Leu
385                 390                 395                 400 gtc tac ctc cac gcc tgc gtc acc gag acg ctc cgc ctg tac ccc gcc      1248
Val Tyr Leu His Ala Cys Val Thr Glu Thr Leu Arg Leu Tyr Pro Ala
                405                 410                 415 gtc cct cag gac ccc aag ggg atc ctg gag gac gtg ctg ccg gac          1296
Val Pro Gln Asp Pro Lys Gly Ile Leu Glu Asp Asp Val Leu Pro Asp
            420                 425                 430 ggg acg aag gtg agg gcc ggg ggg atg gtg acg tac gtg ccc tac tcg      1344
Gly Thr Lys Val Arg Ala Gly Gly Met Val Thr Tyr Val Pro Tyr Ser
        435                 440                 445 atg ggg cgg atg gag tac aac tgg ggc ccc gac gcg gcg agc ttc cgg      1392
Met Gly Arg Met Glu Tyr Asn Trp Gly Pro Asp Ala Ala Ser Phe Arg
    450                 455                 460 ccg gag cgg tgg atc aac gag gat ggc gcg ttc cgc aac gcg tcg ccg      1440
Pro Glu Arg Trp Ile Asn Glu Asp Gly Ala Phe Arg Asn Ala Ser Pro
465                 470                 475                 480 ttc aag ttc acg gcg ttc cag gcg ggg ccg agg atc tgc ctg ggc aag      1488
Phe Lys Phe Thr Ala Phe Gln Ala Gly Pro Arg Ile Cys Leu Gly Lys
                485                 490                 495 gac tcg gcg tac ctg cag atg aag atg gcg ctg gcc atc ctc ttc cgc      1536
Asp Ser Ala Tyr Leu Gln Met Lys Met Ala Leu Ala Ile Leu Phe Arg
            500                 505                 510 ttc tac agc ttc cgg ctg ctg gag ggg cac ccg gtg cag tac cgc atg      1584
Phe Tyr Ser Phe Arg Leu Leu Glu Gly His Pro Val Gln Tyr Arg Met
        515                 520                 525 atg acc atc ctc tcc atg gcg cac ggc ctc aag gtc cgc gtc tct agg      1632
Met Thr Ile Leu Ser Met Ala His Gly Leu Lys Val Arg Val Ser Arg
    530                 535                 540 gcc gtc tga tgt cat ggc gat ttg gat atg gat atc gtc ccg ctt aat      1680
Ala Val     Cys His Gly Asp Leu Asp Met Asp Ile Val Pro Leu Asn
545                 550                 555 cca cga caa ata acg ctc gtg tta caa att tgc atg cat gca tgt aag      1728
Pro Arg Gln Ile Thr Leu Val Leu Gln Ile Cys Met His Ala Cys Lys
                565                 570                 575 gga aag cga tgg gtt tca ttg gtg gct tgg ctt aag cct taaaaactcc       1777
Gly Lys Arg Trp Val Ser Leu Val Ala Trp Leu Lys Pro
            580                 585 gtcgggtctt gcgaaccacc acatcactag tgttttgtac tctactcctc agtggaagtg   1837
tagtgacagc atacaagttc atcatatata ttatcctctt tcttaaaaaa aaaaaaaaaa   1897
aaactcgag                                                            1906

<210> SEQ ID NO 2
<211> LENGTH: 546
<212> TYPE: PRT
<213> ORGANISM: Zea mays

<400> SEQUENCE: 2

Glu Phe Gly Thr Arg Glu Ala His Leu Thr Pro Ala Thr Pro Ser Pro
  1               5                  10                  15

Phe Phe Pro Leu Ala Gly Pro His Lys Tyr Ile Ala Leu Leu Leu Val
                20                  25                  30

Val Leu Ser Trp Ile Leu Val Gln Arg Trp Ser Leu Arg Lys Gln Lys
            35                  40                  45

Gly Pro Arg Ser Trp Pro Val Ile Gly Ala Thr Val Glu Gln Leu Arg
```

-continued

```
            50                  55                  60
Asn Tyr His Arg Met His Asp Trp Leu Val Gly Tyr Leu Ser Arg His
 65                  70                  75                  80

Arg Thr Val Thr Val Asp Met Pro Phe Thr Ser Tyr Thr Tyr Ile Ala
                     85                  90                  95

Asp Pro Val Asn Val Glu His Val Leu Lys Thr Asn Phe Thr Asn Tyr
                100                 105                 110

Pro Lys Gly Ile Val Tyr Arg Ser Tyr Met Asp Val Leu Leu Gly Asp
                115                 120                 125

Gly Ile Phe Asn Ala Asp Gly Glu Leu Trp Arg Lys Gln Arg Lys Thr
130                 135                 140

Ala Ser Phe Glu Phe Ala Ser Lys Asn Leu Arg Asp Phe Ser Ala Ile
145                 150                 155                 160

Val Phe Arg Glu Tyr Ser Leu Lys Leu Ser Gly Ile Leu Ser Gln Ala
                165                 170                 175

Ser Lys Ala Gly Lys Val Val Asp Met Gln Glu Leu Tyr Met Arg Met
                180                 185                 190

Thr Leu Asp Ser Ile Cys Lys Val Gly Phe Gly Val Glu Ile Gly Thr
                195                 200                 205

Leu Ser Pro Asp Leu Pro Glu Asn Ser Phe Ala Gln Ala Phe Asp Ala
                210                 215                 220

Ala Asn Ile Ile Ile Thr Leu Arg Phe Ile Asp Pro Leu Trp Arg Ile
225                 230                 235                 240

Lys Arg Phe Phe His Val Gly Ser Glu Ala Leu Leu Ala Gln Ser Ile
                245                 250                 255

Lys Leu Val Asp Glu Phe Thr Tyr Ser Val Ile Arg Arg Lys Ala
                260                 265                 270

Glu Ile Val Glu Val Arg Ala Ser Gly Lys Gln Glu Lys Met Lys His
                275                 280                 285

Asp Ile Leu Ser Arg Phe Ile Glu Leu Gly Glu Ala Gly Asp Asp Gly
                290                 295                 300

Gly Gly Phe Gly Asp Asp Lys Ser Leu Arg Asp Val Val Leu Asn Phe
305                 310                 315                 320

Val Ile Ala Gly Arg Asp Thr Thr Ala Thr Thr Leu Ser Trp Phe Thr
                325                 330                 335

His Met Ala Met Ser His Pro Asp Val Ala Glu Lys Leu Arg Arg Glu
                340                 345                 350

Leu Cys Ala Phe Glu Ala Glu Arg Ala Arg Glu Glu Gly Val Thr Leu
                355                 360                 365

Val Leu Cys Gly Gly Ala Asp Ala Asp Lys Ala Phe Ala Ala Arg
                370                 375                 380

Val Ala Gln Phe Ala Gly Leu Leu Thr Tyr Asp Ser Leu Gly Lys Leu
385                 390                 395                 400

Val Tyr Leu His Ala Cys Val Thr Glu Thr Leu Arg Leu Tyr Pro Ala
                405                 410                 415

Val Pro Gln Asp Pro Lys Gly Ile Leu Glu Asp Val Leu Pro Asp
                420                 425                 430

Gly Thr Lys Val Arg Ala Gly Gly Met Val Thr Tyr Val Pro Tyr Ser
                435                 440                 445

Met Gly Arg Met Glu Tyr Asn Trp Gly Pro Asp Ala Ala Ser Phe Arg
                450                 455                 460

Pro Glu Arg Trp Ile Asn Glu Asp Gly Ala Phe Arg Asn Ala Ser Pro
465                 470                 475                 480
```

```
Phe Lys Phe Thr Ala Phe Gln Ala Gly Pro Arg Ile Cys Leu Gly Lys
                485                 490                 495

Asp Ser Ala Tyr Leu Gln Met Lys Met Ala Leu Ala Ile Leu Phe Arg
            500                 505                 510

Phe Tyr Ser Phe Arg Leu Leu Glu Gly His Pro Val Gln Tyr Arg Met
        515                 520                 525

Met Thr Ile Leu Ser Met Ala His Gly Leu Lys Val Arg Val Ser Arg
    530                 535                 540

Ala Val
545

<210> SEQ ID NO 3
<211> LENGTH: 494
<212> TYPE: DNA
<213> ORGANISM: Sorghum sp.
<220> FEATURE:
<221> NAME/KEY: modified_base
<222> LOCATION: (351)
<223> OTHER INFORMATION: a, c, g, t, unknown or other
<220> FEATURE:
<221> NAME/KEY: modified_base
<222> LOCATION: (367)
<223> OTHER INFORMATION: a, c, g, t, unknown or other
<220> FEATURE:
<221> NAME/KEY: modified_base
<222> LOCATION: (369)
<223> OTHER INFORMATION: a, c, g, t, unknown or other
<220> FEATURE:
<221> NAME/KEY: modified_base
<222> LOCATION: (384)
<223> OTHER INFORMATION: a, c, g, t, unknown or other
<220> FEATURE:
<221> NAME/KEY: modified_base
<222> LOCATION: (409)
<223> OTHER INFORMATION: a, c, g, t, unknown or other
<220> FEATURE:
<221> NAME/KEY: modified_base
<222> LOCATION: (444)
<223> OTHER INFORMATION: a, c, g, t, unknown or other
<220> FEATURE:
<221> NAME/KEY: modified_base
<222> LOCATION: (462)
<223> OTHER INFORMATION: a, c, g, t, unknown or other
<220> FEATURE:
<221> NAME/KEY: modified_base
<222> LOCATION: (490)
<223> OTHER INFORMATION: a, c, g, t, unknown or other

<400> SEQUENCE: 3
ggaattcggc ttatgccgtt cacttcctac acctacatcg ctgacccggt gaatgtcgag      60
catgtcctca agactaactt caccaattac cccaaggggg acgtgtacag atcctacatg     120
gatgtgctcc tcggtgacgg catattcaac gctgacggcg agctgtggag gaagcagagg     180
aagacggcga gtttcgagtt cgcctccaag aacctgaggg atttcagtgc caatgttttc     240
agagagtact ccctgaagct gtcgggcata ctgagtcagg catccaaggc aggcaaagtt     300
gttgacatgc aggaacttta catgaggatg acactggact cgatctgcaa ngttgggttc     360
ggggtcnana tcggcacgct gtcnccggat ctccccgaga acagcttcnc ccaagcgttc     420
gatgccgcta acatcatcgt cacnctgcgg ttcatccacc cnctgtggcg catccagaag     480
ttcttccccn gtca                                                      494

<210> SEQ ID NO 4
<211> LENGTH: 158
<212> TYPE: PRT
<213> ORGANISM: Sorghum sp.
```

```
<220> FEATURE:
<221> NAME/KEY: MOD_RES
<222> LOCATION: (113)
<223> OTHER INFORMATION: Variable amino acid
<220> FEATURE:
<221> NAME/KEY: MOD_RES
<222> LOCATION: (119)
<223> OTHER INFORMATION: Variable amino acid
<220> FEATURE:
<221> NAME/KEY: MOD_RES
<222> LOCATION: (133)
<223> OTHER INFORMATION: Variable amino acid

<400> SEQUENCE: 4
```

Met Pro Phe Thr Ser Tyr Thr Tyr Ile Ala Asp Pro Val Asn Val Glu
1               5                   10                  15

His Val Leu Lys Thr Asn Phe Thr Asn Tyr Pro Lys Gly Asp Val Tyr
            20                  25                  30

Arg Ser Tyr Met Asp Val Leu Leu Gly Asp Gly Ile Phe Asn Ala Asp
        35                  40                  45

Gly Glu Leu Trp Arg Lys Gln Arg Lys Thr Ala Ser Phe Glu Phe Ala
    50                  55                  60

Ser Lys Asn Leu Arg Asp Phe Ser Ala Asn Val Phe Arg Glu Tyr Ser
65                  70                  75                  80

Leu Lys Leu Ser Gly Ile Leu Ser Gln Ala Ser Lys Ala Gly Lys Val
                85                  90                  95

Val Asp Met Gln Glu Leu Tyr Met Arg Met Thr Leu Asp Ser Ile Cys
            100                 105                 110

Xaa Val Gly Phe Gly Val Xaa Ile Gly Thr Leu Ser Pro Asp Leu Pro
        115                 120                 125

Glu Asn Ser Phe Xaa Gln Ala Phe Asp Ala Ala Asn Ile Ile Val Thr
    130                 135                 140

Leu Arg Phe Ile His Pro Leu Trp Arg Ile Gln Lys Phe Phe
145                 150                 155

```
<210> SEQ ID NO 5
<211> LENGTH: 1092
<212> TYPE: DNA
<213> ORGANISM: Zea mays

<400> SEQUENCE: 5
gaattccaag cgaggccctt gtagcagaga gtgttgctga tgcagtcggc ggaaatgagt      60
gcgtgctgag agcaacgctg aggggttcca gggatggcaa tggctatggc aatcggctag     120
aggtggagga caaggtggtg aggattggga gggcaaccta tggcaagttg gtgaagaggc     180
acgcaatgag agatctattc agacttacac tggatgccgc caacaaattc aacctttaga     240
ttttgatact gtcactccta ctttattcct tggttgggca acttccaata ggctcatgtt     300
aatcaatgat tagtgattat tcagcaaata ttccttgttg tttgacattt ataatatgtg     360
gggtgagacg gattaaatat catccatgag agctttatct tcatgctctc ttgattttgg     420
tttcagatca ttctttcagt gttcacaaga attttctcag tttggtccat gtaattttg      480
aagtgaggtt ccttaaattt cattatgctt cctttctttt ctagactagc aactgcatga     540
cttttcactt tgggttcaca aattgactca caagaaaaca aattcacttt tgggttcaca     600
aattcctctt caggatgtac ttttcacttg aactgtcatg tataggaaca aggaatggct     660
cagttttta ggaacaatgt acagattca tttcagaact cttctgggtt ggttgagttt       720
cagactttt gtaccaagct gatggatcac aatacttgtt ccaaagtctc gataacagaa       780
```

| | |
|---|---:|
| actggcaact cctaattgat aataaaaaga ataaaataca gtatcagata tctcattttc | 840 |
| ttggttggca gatcacaaaa aggaacacaa aggctaagcc tcctacttgt tcgggagtta | 900 |
| ggtcagggac accatatgaa tgaaagaaat cttaatttgg ggtcacacca agattgtctc | 960 |
| tctcgaggtt gggggtccc taaggttggt agtagcaata cccaatatat cacctaacaa | 1020 |
| acccaatcca tgctacatac atacatagca tccatcactt gtagactgga cccttcatca | 1080 |
| agagcaccat gg | 1092 |

<210> SEQ ID NO 6
<211> LENGTH: 267
<212> TYPE: DNA
<213> ORGANISM: Zea mays

<400> SEQUENCE: 6

| | |
|---|---:|
| ccccatctca ttttcttggt tggcagatca caaaaggaa cacaaaggct aagcctccta | 60 |
| cttgttcggg agttaggtca gggacaccat atgaatgaaa gaaatcttaa tttgggtca | 120 |
| caccaagatt gtctctctcg aggttggggg gtccctaagg ttggtagtag caatacccaa | 180 |
| tatatcacct aacaaaccca atccatgcta catacataca tagcatccat cacttgtaga | 240 |
| ctggacccett catcaagagc accatgg | 267 |

<210> SEQ ID NO 7
<211> LENGTH: 3897
<212> TYPE: DNA
<213> ORGANISM: Zea mays

<400> SEQUENCE: 7

| | |
|---|---:|
| gaattccaag cgaggccctt gtagcagaga gtgttgctga tgcagtcggc ggaaatgagt | 60 |
| gcgtgctgag agcaacgctg aggggttcca gggatggcaa tggctatggc aatcggctag | 120 |
| aggtggagga caaggtggtg aggattggga gggcaaccta tggcaagttg gtgaagaggc | 180 |
| acgcaatgag agatctattc agacttacac tggatgccgc caacaaattc aacctttaga | 240 |
| ttttgatact gtcactccta ctttattcct tggttgggca acttccaata ggctcatgtt | 300 |
| aatcaatgat tagtgattat tcagcaaata ttcttgtttg tttgacattt ataatatgtg | 360 |
| gggtgagacg gattaaatat catccatgag agctttatct tcatgctctc ttgattttgg | 420 |
| tttcagatca ttcttttcagt gttcacaaga attttctcag tttggtccat gtaattttg | 480 |
| aagtgaggtt ccttaaattt cattatgctt cctttctttt ctagactagc aactgcatga | 540 |
| cttttcactt tgggttcaca aattgactca caagaaaaca aattcacttt tgggttcaca | 600 |
| aattcctctt caggatgtac ttttcacttg aactgtcatg tataggaaca aggaatggct | 660 |
| cagttttaa ggacaatgt acagatttca tttcagaact cttctggtt ggttgagttt | 720 |
| cagactttt gtaccaagct gatggatcac aatacttgtt ccaaagtct gataacagaa | 780 |
| actggcaact cctaattgat aataaaaaga ataaaataca gtatcagata tctcattttc | 840 |
| ttggttggca gatcacaaaa aggaacacaa aggctaagcc tcctacttgt tcgggagtta | 900 |
| ggtcagggac accatatgaa tgaaagaaat cttaatttgg ggtcacacca agattgtctc | 960 |
| tctcgaggtt gggggtccc taaggttggt agtagcaata cccaatatat cacctaacaa | 1020 |
| acccaatcca tgctacatac atacatagca tccatcactt gtagactgga cccttcatca | 1080 |
| agagcaccat ggaggaagct cacatcacgc cggcgacgcc atcgccattc ttcccactag | 1140 |
| cagggcctca caagtacatc gcgctcctcc tggttgtcct ctcatggatc ctggtccaga | 1200 |
| ggtggagcct gaggaagcag aaaggcccga gatcatggcc agtcatcggt gcaacggtgg | 1260 |

-continued

| | |
|---|---|
| agcagctgag gaactaccac cggatgcacg actggcttgt cgggtacctg tcacggcaca | 1320 |
| ggacagtgac cgtcgacatg ccgttcactt cctacaccta catcgctgac ccggtgaatg | 1380 |
| tcgagcatgt cctcaagact aacttcacca attaccccaa ggtaaatgac ctgaactcac | 1440 |
| tgatgttcag tcttcggaaa tcagagctga agctgaatc gaatgtgcct gaacaccgtg | 1500 |
| tagggaatcg tgtacagatc ctacatggac gtgctcctcg gtgacggcat cttcaacgcc | 1560 |
| gacggcgagc tgtggaggaa gcagaggaag acggcgagtt tcgagttcgc ctccaagaac | 1620 |
| ctgagggatt tcagcgccat tgtgttcaga gagtactccc tgaagctgtc gggtatactg | 1680 |
| agccaggcat ccaaggcagg caaagttgtg gacatgcagg tgagatcact gctcccttgc | 1740 |
| cattgccaac atgagcattt caacctgaga cacgagagcc accttgccga ttcaggaact | 1800 |
| ttacatgagg atgacgctgg actccatctg caaggtgggg ttcggggtcg agatcggcac | 1860 |
| gctgtcgccg gatctccccg agaacagctt cgcgcaggcg ttcgatgccg ccaacatcat | 1920 |
| cgtcacgctg cggttcatcg acccgctgtg gcgcatcaag aggttcttcc acgtcgggtc | 1980 |
| agaggccctc ctagcgcaga gcatcaagct cgtggacgag ttcacctaca gcgtgatccg | 2040 |
| ccggaggaag gccgagatcg tcgaggcccg ggccagcggc aaacaggaga aggtacgtgc | 2100 |
| acatgactgt ttcgattctt cagttcatcg tcttggccgg gatggacctg atcctgattg | 2160 |
| attatatatc cgtgtgactt gtgaggacaa attaaaatgg gcagatgaag cacgacatcc | 2220 |
| tgtcacggtt catcgagcta ggcgaggccg gcgacgacgg cggcggcttc ggggacgaca | 2280 |
| agagcctccg ggacgtggtg ctcaacttcg tgatcgccgg gcgggacacg acggcgacga | 2340 |
| cgctgtcgtg gttcacgcac atggccatgt cccacccgga cgtggccgag aagctgcgcc | 2400 |
| gcgagctgtg cgcgttcgag gcggagcgcg cgcgcgagga gggcgtcgcg ctcgtgccct | 2460 |
| gcggcggcgc tgacgccgac gacaaggcgt tcgccgcccg cgtggcgcag ttcgcgggcc | 2520 |
| tcctcaccta cgacagcctc ggcaagctgg tctacctcca cgcctgcgtc accgagacgc | 2580 |
| tccgcctgta ccccgccgtc cctcaggtga gcgcgcccga cacgcgacct ccggtccaga | 2640 |
| gcacagcatg cagtgagtgg acctgaatgc aatgcacatg cacttgcgcg cgcgcaggac | 2700 |
| cccaagggga tcctggagga cgacgtgctg ccggacggga cgaaggtgag ggccggcggg | 2760 |
| atggtgacgt acgtgcccta ctcgatgggg cggatggagt acaactgggg ccccgacgcg | 2820 |
| gcgagcttcc ggccggagcg gtggatcaac gaggatggcg cgttccgcaa cgcgtcgccg | 2880 |
| ttcaagttca cggcgttcca ggcggggccg aggatctgcc tgggcaagga ctcggcgtac | 2940 |
| ctgcagatga agatggcgct ggccatcctc ttgcgcttct acagcttccg gctgctggag | 3000 |
| gggcacccgg tgcagtaccg catgatgacc atcctctcca tggcgcacgg cctcaaggtc | 3060 |
| cgcgtctcta gggccgtctg atgtcatggc gatttgggat atcatcccgc ttaatcctta | 3120 |
| aaaatttgca tgcatgcatg taagggaaag cgatgggttt cattggtggc ttggcttaag | 3180 |
| ccttaaaaac tccgtcgggt cttgcgaacc accacatcac tagtgttttg tactctactc | 3240 |
| ctcagtggaa gtgtagtgac agcatacaag ttcatcatat atattatcct ctttcttcgc | 3300 |
| cggatgcttc ccgggacctt ttggagacca ttactgacag gcgtgtgaaa aaaaggcttc | 3360 |
| ttctgcggcg aagttttggg ttcagagtct tggcgtctttt gcagcagaaa aaaggtttgg | 3420 |
| aaggatctga accctgaacc gaaaatggct tcggaaatat gctcgcatcg gggcggggcc | 3480 |
| gtcactcggg atgacgacaa gcccacaagc agtgagagcg aagcgatctt tggagtttgg | 3540 |
| agacactctc ggacccctcg gcgctccgcg agctcatctt cgcctcctct gtcgtgtccg | 3600 |

-continued

| | |
|---|---|
| tggcggcacc gcgcccgccc gcctcgtgtt cgaccaaatc ccgcgccccg accggttcgt | 3660 |
| gtacaacacc ctcatccgcg gcgccgcgcg cagtgacacg ccccgggacg ccgtatacat | 3720 |
| ctataaatca tggtattgta ctttatttc aaacggcctt aacacaacca tattttatg | 3780 |
| gtaaacacgt tcaaaattga cacaaattta aaacaggcac aaaccgtagc taaacataag | 3840 |
| agaatgagag acaacccaaa ggttagagat gaaataagct gagtaaacga cgaattc | 3897 |

<210> SEQ ID NO 8
<211> LENGTH: 360
<212> TYPE: DNA
<213> ORGANISM: Zea mays

<400> SEQUENCE: 8

| | |
|---|---|
| caggacccca agggatcct ggaggacgac gtgctgccgg acgggacgaa ggtgagggcc | 60 |
| ggcgggatgg tgacgtacgt gccctactcg atggggcgga tggagtacaa ctggggcccc | 120 |
| gacgcggcga gcttccggcc ggaggccgg agcggtggat caacgaggat ggcgcgttcc | 180 |
| gcaacgcgtc gccgttcaag ttcacggcgt tccaggcggg gccgaggatc tgcctgggca | 240 |
| aggactcggc gtacctgcag atgaagatgg cgctggccat cctcttgcgc ttctacagct | 300 |
| tccggctgct ggaggggcac ccggtgcagt accgcatgat gaccatcctc tccatggcgc | 360 |

<210> SEQ ID NO 9
<211> LENGTH: 352
<212> TYPE: DNA
<213> ORGANISM: Zea mays

<400> SEQUENCE: 9

| | |
|---|---|
| caggacccca agggatcct ggaggacgac gtgctgccgg acgggacgaa ggtgagggcc | 60 |
| ggcgggatgg tgacgtacgt gccctactcg atggggcgga tggagtacaa ctggggcccc | 120 |
| gacgcggcga gcttccggcc ggagcggtgg atcaacgagg atggcgcgtt ccgcaacgcg | 180 |
| tcgccgttca agttcacggc gttccaggcg gggccgagga tctgcctggg caaggactcg | 240 |
| gcgtacctgc agatgaagat ggcgctggcc atcctcttcc gcttctacag cttccggctg | 300 |
| ctggaggggc acccggtgca gtaccgcatg atgaccatcc tctccatggc gc | 352 |

<210> SEQ ID NO 10
<211> LENGTH: 1440
<212> TYPE: DNA
<213> ORGANISM: Zea mays

<400> SEQUENCE: 10

| | |
|---|---|
| cggagctagg ggtgaaaacg ggtagggtac ccgaaacggg taccggatac ggatactgat | 60 |
| tcgggaccat ttttcggata cggatacggg tatttttag attcgggacg gatacgggta | 120 |
| atacccggat agtatggctt cggattcggg tcggatacgg agcgagtact acccggtaaa | 180 |
| tacccgata ctcgggtcgg ataccgggta cccggaattc gggtacccgt tttttctttt | 240 |
| tctgcaaaat aatatagtta taaaatcata acttttacat atgaaatcgg atgaagataa | 300 |
| agtttatatg aaaattgtag agctcgaaga gatctataac tttgtagtac atcacatttt | 360 |
| tgtttaaaca tatctttagg ccaaaatcat taaaataatg tctaaattta tatcaaaata | 420 |
| atagacttta tcattttcat gtggggactt aagattatat ccatgtggga acttaggatt | 480 |
| atctttttat aaactatttta ttaatattgg taacttattt gcaattttcg gtcgacgcta | 540 |
| caatatttt tgaatttaaa ttgtattttg atgattttct acaacaagaa attaataata | 600 |
| caccaaatag cctaaaaaat tcatggattt ttacggggac acaacatata tccacatata | 660 |

```
gttctcaaaa acatttggac tataaaatcc acaagatgtt ggtgtttctt ccattctact        720
cccacttatt gcgtgagtta catgtgaaat cattttatgt atcgaagttt caacataatt        780
aatatttcac ttatcatttt catgtggcga cttgaggttt tatttgaata gaatgtttat       840
ttgttttggt aagcttttg cattttggat caaactagtg tatttatgaa ttttaattat        900
actttgatga ttttatgtag aaagaaatta ataatgtata aatagcctca gaaatctatg        960
aaattatacg aaggtacaac atatggccac atatagtcat aacaaataat gggaccataa      1020
aatccacagg atgtcaacgt ttcttctatt ttatttccac ttattgcgtg agttacacgt      1080
gaaatcactc taagtatcca agtttcaaca taatcaatac ttcactttac cattttttacg      1140 tgggaacttg agattatctt ctattaaatg cttattagta ttaatttact tgcaatttcg      1200
tggtcgaaca agaatatttt ttgataacca attaatgcat tatccgacaa gtatccgata      1260
tccgatcaaa taatatccgt atccgtcact tatccgctcg ataaatatc cggtccctgt      1320 atccgtatcc gtcccgtttc taactatccg tatccgatcc cgaatccgtt ttaaatacat      1380
tagggtagga tacaggatga gctaatatcc gtccgtatcc gcccgttttc accccctagcc      1440

<210> SEQ ID NO 11
<211> LENGTH: 4182
<212> TYPE: DNA
<213> ORGANISM: Zea mays

<400> SEQUENCE: 11
aactgcatga cttttcactt tgggttcaca aattgactca caagaaaaca aattcacttt         60
tgggttcaca aattcctctt caggatgtac ttttcacttg aaactgtcat gtataggaac        120
aaggaatggc tcagttttta aggaacaatg tacagatttc atttcagaac tctttctggt        180
tggttgagtt tcagactttt tgtaccaagc tgatggatca caatacttgt ttccaaagtc        240
tgataacaga aactggcaac tcctaattga taataaaaag aataaaatac agtatcagat        300
atctcatttt cttggttggc agatcacaaa aaggaacaca aaggctaagc ctcctacttg        360
ttcgggagtt aggtcaggga caccatatga atgaaagaaa tcttaatttg gggtcacacc        420
aagattgtct ctctcgaggt tggggggtcc ctaaggttgg tagtagcaat acccaatata        480
tcacctaaca aacccaatcc atgctacata catacatagc atccatcact tgtagactgg        540
acccttcatc aagagcacca tggaggaagc tcacatcacg ccggcgacgc catcgccatt        600
cttcccacta gcagggcctc acaagtacat cgcgctcctc ctggttgtcc tctcatggat        660
cctggtccag aggtggagcc tgaggaagca gaaaggcccg agatcatggc cagtcatcgg        720
tgcaacggtg gagcagctga ggaactacca ccggatgcac gactggcttg tcgggtacct        780
gtcgcggcac aggacagtga ccgtcgacat gccgttcact tcctacacct acatcgctga        840
cccggtgaat gtcgagcatg tcctcaagac taacttcacc aattacccca aggtaaatga        900
cctgaactca ctgatgttca gtcttcggaa atcagagctg aaagctgaat cgaatgtgcc        960
tgaacaccgt gtagggaatc gtgtacagat cctacatgga cgtgctcctc ggtgacggca      1020
tcttcaacgc cgacggcgag ctgtggagga agcagaggaa gacggcgagt tcgagttcg       1080 cctccaagaa cctgagggat ttcagcgcca ttgtgttcag agagtactcc ctgaagctgt      1140
cgggtatact gagccaggca tccaaggcag gcaaagttgt ggacatgcag gtgagatcac      1200
tgctcccttg ccattgccaa catgagcatt tcaacctgag acacgagagc taccttgccg      1260
attcaggaac tttacatgag gatgacgctg gactccatct gcaaggttgg gttcggggtc      1320
```

```
gagatcggca cgctgtcgcc ggatctcccc gagaacagct tcgcgcaggc gttcgatgcc    1380
gccaacatca tcgtcacgct gcggttcatc gacccgctgt ggcgcatcaa gaggttcttc    1440
cacgtcgggt cagaggccct cctagcgcag agcatcaagc tcgtggacga gttcacctac    1500
agcgtgatcc gccggaggaa ggccgagatc gtcgaggtcc gggccagcgg caaacaggag    1560
aaggtacgtg tacatgactg tttcgattct tcagttcatc gtcttggccg ggatggacct    1620
gatcctgatt gattatatat ccgtgtgact tgtgaggaca aattaaaatg ggcagatgaa    1680
gcacgacatc ctgtcacggt tcatcgagct aggcgaggcc ggcgacgacg gcggcggctt    1740
cggggacgac aagagcctcc gggacgtggt gctcaacttc gtgatcgccg gcgggacac    1800
gacggcgacg acgctgtcgt ggttcacgca catggccatg tcccacccgg acgtggccga    1860
gaagctgcgc cgcgagctgt gcgcgttcga ggcggagcgc gcgcgcgagg agggcgtcgc    1920
gctcgtgccc tgcggcggcg ctgacgccga cgacaaggcg ttcgccgccc gcgtggcgca    1980
gttcgcggc ctcctcacct acgacagcct cggcaagctg gtctacctcc acgcctgcgt    2040
caccgagacg ctccgcctgt accccgccgt ccctcaggtg agcgcgcccg acacgacctc    2100
cggtccgcga tgcaacgcat atgtggctgt ccgcagagca cagcatgcag tgagtggacc    2160
tgaatgcact atgcaatgca cttgcgcgcg cgcaggaccc caaggggatc ctggaggacg    2220
acgtgctgcc ggacgggacg aaggtgaggg ccggcgggat ggtgacgtac gtgccctact    2280
cgatggggcg gatggagtac aactggggcc ccgacgcggc gagcttccgg ccggagctag    2340
gggtgaaaac gggtagggta cccgaaacgg gtaccggata cggatactga ttcgggacca    2400
tttttcggat acggatacgg gtattttta gattcgggac ggatacgggt aatacccgga    2460
tagtatggct tcggattcgg gtcggatacg gagcgagtac tacccggtaa ataccggat    2520
actcgggtcg gataccgggt acccggaatt cgggtacccg tttttcttt ttctgcaaaa    2580
taatatagtt ataaaatcat aactttaca tatgaaatcg gatgaagata agtttatat    2640
gaaaattgta gagctcgaag agatctataa ctttgtagta catcacattt ttgtttaaac    2700
atatctttag gccaaaatca ttaaaataat gtctaaattt atatcaaaat aatagacttt    2760
atcattttca tgtggggact taagattata tccatgtggg aacttaggat tatcttttta    2820
taaactattt attaatattg gtaacttatt tgcaattttc ggtcgacgct acaatatttt    2880
tatgaattta attgtattt tgatgatttc tacaacaaga aattaataat acaccaaata    2940
gcctaaaaaa tcatggatt tttacgggga cacaacatat atccacatat agttctcaaa    3000
aacatttgga ctataaaatc cacaagatgt tggtgtttct tccattctac tcccacttat    3060
tgcgtgagtt acatgtgaaa tcattttatg tatcgaagtt tcaacataat taatatttca    3120
cttatcattt tcatgtggcg acttgaggtt ttatttgaat agaatgttta tttgttttgg    3180
taagcttttt gcattttgga tcaaactagt gtatttatga attttaatta tactttgatg    3240
attttatgta gaaagaaatt aataatgtat aaatagcctc agaaatctat gaaattatac    3300
gaaggtacaa catatggcca catatagtca taacaaataa tgggaccata aaatccacag    3360
gatgtcaacg tttcttctat tttatttcca cttattgcgt gagttacacg tgaaatcact    3420
ctaagtatcc aagtttcaac ataatcaata cttcacttta ccattttac gtgggaactt    3480
gagattatct tctattaaat gcttattagt attaatttac ttgcaatttc gtggtcgaac    3540
aagaatattt tttgataacc aattaatgca ttatccgaca agtatccgat atccgatcaa    3600
ataatatccg tatccgtcac ttatccgctc ggataaaat ccgtccctg tatccgtatc    3660
cgtcccgttt ctaactatcc gtatccgatc ccgaatccgt tttaaataca ttagggtagg    3720
```

```
atacaggatg agctaatatc cgtccgtatc cgcccgtttt caccectagc cggagcggtg   3780 gatcaacgag gatggcgcgt tccgcaacgc gtcgccgttc aagttcacgg cgttccaggc   3840
ggggccgagg atctgcctgg gcaaggactc ggcgtacctg cagatgaaga tggcgctggc   3900
catccttctt gcgcttctac agcttccggc tgctggaggg gcacccggtg cagtaccgca   3960
tgatgaccat cctctccatg cgcacggcc tcaaggtccg cgtctctagg gccgtctgat    4020
gtcatggcga tttgggatat catcccgctt aatccacgac aaataacgtt cgtgttacaa   4080
atttgcatgc atgcatgtaa gggaaagcga tgggtttcat tggtggcttg gcttaagcct   4140
taaaaactcc gtcgggttct tgcgaaccac cacatcacta ga                     4182
```

<210> SEQ ID NO 12
<211> LENGTH: 505
<212> TYPE: PRT
<213> ORGANISM: Arabidopsis thaliana

<400> SEQUENCE: 12

```
Leu Val Ile Ala Cys Met Val Thr Ser Trp Ile Phe Leu His Arg Trp
  1               5                  10                  15

Gly Gln Arg Asn Lys Ser Gly Pro Lys Thr Trp Pro Leu Val Gly Ala
                 20                  25                  30

Ala Ile Glu Gln Leu Thr Asn Phe Asp Arg Met His Asp Trp Leu Val
             35                  40                  45

Glu Tyr Leu Tyr Asn Ser Arg Thr Val Val Pro Met Pro Phe Thr
         50                  55                  60

Thr Tyr Thr Tyr Ile Ala Asp Pro Ile Asn Val Glu Tyr Val Leu Lys
 65                  70                  75                  80

Thr Asn Phe Ser Asn Tyr Pro Lys Gly Glu Thr Tyr His Ser Tyr Met
                 85                  90                  95

Glu Val Leu Leu Gly Asp Gly Ile Phe Asn Ser Asp Gly Glu Leu Trp
            100                 105                 110

Arg Lys Gln Arg Lys Thr Ala Ser Phe Glu Phe Ala Ser Lys Asn Leu
        115                 120                 125

Arg Asp Phe Ser Thr Val Val Phe Lys Glu Tyr Ser Leu Lys Leu Phe
    130                 135                 140

Thr Ile Leu Ser Gln Ala Ser Phe Lys Glu Gln Gln Val Asp Met Gln
145                 150                 155                 160

Glu Leu Leu Met Arg Met Thr Leu Asp Ser Ile Cys Lys Val Gly Phe
                165                 170                 175

Gly Val Glu Ile Gly Thr Leu Ala Pro Glu Leu Pro Glu Asn His Phe
            180                 185                 190

Ala Lys Ala Phe Asp Thr Ala Asn Ile Ile Val Thr Leu Arg Phe Ile
        195                 200                 205

Asp Pro Leu Trp Lys Met Lys Lys Phe Leu Asn Ile Gly Ser Glu Ala
    210                 215                 220

Leu Leu Gly Lys Ser Ile Lys Val Val Asn Asp Phe Thr Tyr Ser Val
225                 230                 235                 240

Ile Arg Arg Arg Lys Ala Glu Leu Leu Glu Ala Gln Val Lys His Asp
                245                 250                 255

Ile Leu Ser Arg Phe Ile Glu Ile Ser Asp Pro Asp Ser Lys Glu
            260                 265                 270

Thr Glu Lys Ser Leu Arg Asp Ile Val Leu Asn Phe Val Ile Ala Gly
        275                 280                 285
```

```
Arg Asp Thr Thr Ala Thr Thr Leu Thr Trp Ala Ile Tyr Met Ile Met
290                 295                 300

Met Asn Glu Asn Val Ala Glu Lys Leu Tyr Ser Glu Leu Gln Glu Leu
305                 310                 315                 320

Glu Lys Glu Ser Ala Glu Ala Thr Asn Thr Ser Leu His Gln Tyr Asp
                325                 330                 335

Thr Glu Asp Phe Asn Ser Phe Asn Glu Lys Val Thr Glu Phe Ala Gly
                340                 345                 350

Leu Leu Asn Tyr Asp Ser Leu Gly Lys Leu His Tyr Leu His Ala Val
                355                 360                 365

Ile Thr Glu Thr Leu Arg Leu Tyr Pro Ala Val Pro Gln Asp Pro Lys
370                 375                 380

Gly Val Leu Glu Asp Asp Met Leu Pro Asn Gly Thr Lys Val Lys Ala
385                 390                 395                 400

Gly Gly Met Val Thr Tyr Val Pro Tyr Ser Met Gly Arg Met Glu Tyr
                405                 410                 415

Asn Trp Gly Ser Asp Ala Ala Leu Phe Lys Pro Glu Arg Trp Leu Lys
                420                 425                 430

Asp Gly Val Phe Gln Asn Ala Ser Pro Phe Lys Phe Thr Ala Phe Gln
                435                 440                 445

Ala Gly Pro Arg Ile Cys Leu Gly Lys Asp Ser Ala Tyr Leu Gln Met
450                 455                 460

Lys Met Ala Met Ala Ile Leu Cys Arg Phe Tyr Lys Phe His Leu Val
465                 470                 475                 480

Pro Asn His Pro Val Lys Tyr Arg Met Met Thr Ile Leu Ser Met Ala
                485                 490                 495

His Gly Leu Lys Val Thr Val Ser Arg
                500                 505

<210> SEQ ID NO 13
<211> LENGTH: 518
<212> TYPE: PRT
<213> ORGANISM: Zea mays

<400> SEQUENCE: 13

Ile Ala Leu Leu Leu Val Val Leu Ser Trp Ile Leu Val Gln Arg Trp
1               5                   10                  15

Ser Leu Arg Lys Gln Lys Gly Pro Arg Ser Trp Pro Val Ile Gly Ala
                20                  25                  30

Thr Val Glu Gln Leu Arg Asn Tyr His Arg Met His Asp Trp Leu Val
                35                  40                  45

Gly Tyr Leu Ser Arg His Arg Thr Val Thr Val Asp Met Pro Phe Thr
50                  55                  60

Ser Tyr Thr Tyr Ile Ala Asp Pro Val Asn Val Glu His Val Leu Lys
65                  70                  75                  80

Thr Asn Phe Thr Asn Tyr Pro Lys Gly Ile Val Tyr Arg Ser Tyr Met
                85                  90                  95

Asp Val Leu Leu Gly Asp Gly Ile Phe Asn Ala Asp Gly Glu Leu Trp
                100                 105                 110

Arg Lys Gln Arg Lys Thr Ala Ser Phe Glu Phe Ala Ser Lys Asn Leu
                115                 120                 125

Arg Asp Phe Ser Ala Ile Val Phe Arg Glu Tyr Ser Leu Lys Leu Ser
130                 135                 140

Gly Ile Leu Ser Gln Ala Ser Lys Ala Gly Lys Val Val Asp Met Gln
145                 150                 155                 160
```

```
Glu Leu Tyr Met Arg Met Thr Leu Asp Ser Ile Cys Lys Val Gly Phe
                165                 170                 175
Gly Val Glu Ile Gly Thr Leu Ser Pro Asp Leu Pro Glu Asn Ser Phe
            180                 185                 190
Ala Gln Ala Phe Asp Ala Ala Asn Ile Ile Thr Leu Arg Phe Ile
        195                 200                 205
Asp Pro Leu Trp Arg Ile Lys Arg Phe His Val Gly Ser Glu Ala
    210                 215                 220
Leu Leu Ala Gln Ser Ile Lys Leu Val Asp Glu Phe Thr Tyr Ser Val
225                 230                 235                 240
Ile Arg Arg Arg Lys Ala Glu Ile Val Glu Val Arg Ala Ser Gly Lys
                245                 250                 255
Gln Glu Lys Met Lys His Asp Ile Leu Ser Arg Phe Ile Glu Leu Gly
            260                 265                 270
Glu Ala Gly Asp Asp Gly Gly Phe Gly Asp Asp Lys Ser Leu Arg
        275                 280                 285
Asp Val Val Leu Asn Phe Val Ile Ala Gly Arg Asp Thr Thr Ala Thr
    290                 295                 300
Thr Leu Ser Trp Phe Thr His Met Ala Met Ser His Pro Asp Val Ala
305                 310                 315                 320
Glu Lys Leu Arg Arg Glu Leu Cys Ala Phe Glu Ala Glu Arg Ala Arg
                325                 330                 335
Glu Glu Gly Val Thr Leu Val Leu Cys Gly Gly Ala Asp Ala Asp Asp
            340                 345                 350
Lys Ala Phe Ala Ala Arg Val Ala Gln Phe Ala Gly Leu Leu Thr Tyr
        355                 360                 365
Asp Ser Leu Gly Lys Leu Val Tyr Leu His Ala Cys Val Thr Glu Thr
    370                 375                 380
Leu Arg Leu Tyr Pro Ala Val Pro Gln Asp Pro Lys Gly Ile Leu Glu
385                 390                 395                 400
Asp Asp Val Leu Pro Asp Gly Thr Lys Val Arg Ala Gly Gly Met Val
                405                 410                 415
Thr Tyr Val Pro Tyr Ser Met Gly Arg Met Glu Tyr Asn Trp Gly Pro
            420                 425                 430
Asp Ala Ala Ser Phe Arg Pro Glu Arg Trp Ile Asn Glu Asp Gly Ala
        435                 440                 445
Phe Arg Asn Ala Ser Pro Phe Lys Phe Thr Ala Phe Gln Ala Gly Pro
    450                 455                 460
Arg Ile Cys Leu Gly Lys Asp Ser Ala Tyr Leu Gln Met Lys Met Ala
465                 470                 475                 480
Leu Ala Ile Leu Phe Arg Phe Tyr Ser Phe Arg Leu Leu Glu Gly His
                485                 490                 495
Pro Val Gln Tyr Arg Met Met Thr Ile Leu Ser Met Ala His Gly Leu
            500                 505                 510
Lys Val Arg Val Ser Arg
        515

<210> SEQ ID NO 14
<211> LENGTH: 128
<212> TYPE: PRT
<213> ORGANISM: Zea mays

<400> SEQUENCE: 14

Gln Asp Pro Lys Gly Ile Leu Glu Asp Asp Val Leu Pro Asp Gly Thr
```

```
                 1               5                  10                 15

Lys Val Arg Ala Gly Gly Met Val Thr Tyr Val Pro Tyr Ser Met Gly
                        20                 25                 30

Arg Met Glu Tyr Asn Trp Gly Pro Asp Ala Ala Ser Phe Arg Pro Glu
                        35                 40                 45

Arg Trp Ile Asn Glu Asp Gly Ala Phe Arg Asn Ala Ser Pro Phe Lys
                        50                 55                 60

Phe Thr Ala Phe Gln Ala Gly Pro Arg Ile Cys Leu Gly Lys Asp Ser
 65                     70                 75                 80

Ala Tyr Leu Gln Met Lys Met Ala Leu Ala Ile Leu Phe Arg Phe Tyr
                        85                 90                 95

Ser Phe Arg Leu Leu Glu Gly His Pro Val Gln Tyr Arg Met Met Thr
                       100                105                110

Ile Leu Ser Met Ala His Gly Leu Lys Val Arg Val Ser Arg Ala Val
                       115                120                125

<210> SEQ ID NO 15
<211> LENGTH: 128
<212> TYPE: PRT
<213> ORGANISM: Zea mays

<400> SEQUENCE: 15

Gln Asp Pro Lys Gly Ile Leu Glu Asp Val Leu Pro Asp Gly Thr
 1               5                  10                 15

Lys Val Arg Ala Gly Gly Met Val Thr Tyr Val Pro Tyr Ser Met Gly
                        20                 25                 30

Arg Met Glu Tyr Asn Trp Gly Pro Asp Ala Ala Ser Phe Arg Pro Glu
                        35                 40                 45

Arg Trp Ile Asn Glu Asp Gly Ala Phe Arg Asn Ala Ser Pro Phe Lys
                        50                 55                 60

Phe Thr Ala Phe Gln Ala Gly Pro Arg Ile Cys Leu Gly Lys Asp Ser
 65                     70                 75                 80

Ala Tyr Leu Gln Met Lys Met Ala Leu Ala Ile Leu Phe Arg Phe Tyr
                        85                 90                 95

Ser Phe Arg Leu Leu Glu Gly His Pro Val Gln Tyr Arg Met Met Thr
                       100                105                110

Ile Leu Ser Met Ala His Gly Leu Lys Val Arg Val Ser Arg Ala Val
                       115                120                125

<210> SEQ ID NO 16
<211> LENGTH: 87
<212> TYPE: PRT
<213> ORGANISM: Zea mays

<400> SEQUENCE: 16

Gln Asp Pro Lys Gly Ile Leu Glu Asp Val Leu Pro Asp Gly Thr
 1               5                  10                 15

Lys Val Arg Ala Gly Gly Met Val Thr Tyr Val Pro Tyr Ser Met Gly
                        20                 25                 30

Arg Met Glu Tyr Asn Trp Gly Pro Asp Ala Ala Ser Phe Arg Pro Glu
                        35                 40                 45

Ala Arg Ser Gly Gly Ser Thr Arg Met Ala Arg Ser Ala Thr Arg Arg
                        50                 55                 60

Arg Ser Ser Ser Arg Ser Arg Arg Gly Arg Gly Ser Ala Trp Ala
 65                     70                 75                 80

Arg Thr Arg Arg Thr Cys Arg
```

<210> SEQ ID NO 17
<211> LENGTH: 1635
<212> TYPE: DNA
<213> ORGANISM: Oryza sativa

<400> SEQUENCE: 17

```
atgaagagcc ccatggagga agctcatgca atgccagtga catcattctt cccagtagca        60
ggaatccaca agctcatagc tatcttcctt gttgtcctct catggatctt ggtccacaag       120
tggagcctga ggaaccagaa agggccaaga tcatggccaa tcatcggcgc gacagtggag       180
caactgaaga actaccacag gatgcatgac tggcttgtcg agtacttgtc gaaggacagg       240
acggtgaccg tcgacatgcc tttcacctcc tacacctaca ttgccgaccc ggtgaacgtc       300
gagcatgtcc tgaagaccaa cttcaccaat taccccaagg gtgaagtgta caggtcttac       360
atggatgtgc tgctcggtga tggcatattc aatgccgacg cgagatgtg gaggaagcaa        420
aggaagacgg cgagcttcga gtttgcctcc aagaacttga gagacttcag cactgtggtg       480
ttcagggagt actccctgaa gctatcaagc attctgagcc aagcatgcaa ggccggcaga       540
gttgtagaca tgcaggaatt gttcatgagg atgacactgg actcgatctg caaggtcggg       600
tttggggttg agatcgggac gctgtcacct gatctcccgg agaacagctt tgcccaggca       660
ttcgacgctg ccaacatcat cgtcacgctg cggttcatcg atcctctgtg gcgtctgaag       720
aagttcttgc acgtcggatc agaggctctc ctcgagcaga gcatgaagct ggttgatgac       780
ttcacctaca gcgtgatccg ccgccgcaag gctgagatct tgcaggctcg agccagcggc       840
aagcaagaga agatcaagca cgacatactg tcgcggttca tcgagctcgg ggaggccggc       900
ggcgacgagg ggggcggcag cttcggggac gacaagagcc tccgcgacgt ggtgctcaac       960
ttcgtgatcg ccgggcgtga cacgacggcg acgacgctgt cgtggttcac gtacatggcg      1020
atgacgcacc cggccgtcgc cgacaagctc cggcgcgagc tggccgcgtt cgaggatgag      1080
cgcgcgcgcg aggagggcgt cgcgctcgcc gacgccgccg cgaggcgtc gttcgcggcg       1140
cgcgtggcgc agttcgcgtc gctgctgagc tacgacgcgg tggggaagct ggtgtacctg      1200
cacgcgtgcg tgacggagac gctccgcctc tacccggcgg tgccgcagga ccccaagggg      1260
atcgtggagg acgacgtgct ccccgacggc accaaggtgc gcgccggcgg gatggtgacg      1320
tacgtgccct actccatggg gaggatggag tacaactggg gccccgacgc ggcgagcttc      1380
cggccggagc ggtggctcag cggcgacggc ggcgcgttcc ggaacgcgtc gccgttcaag      1440
ttcaccgcgt ccaggccgg gccgcggatc tgcctcggca aggactccgc ctacctccag       1500
atgaagatgg cgctcgccat cctcttccgc ttctacacct cgacctcgt cgaggaccac       1560
cccgtcaagt accggatgat gaccatcctc tccatggctc acggcctcaa ggtccgcgtc      1620
tccacctccg tctga                                                         1635
```

<210> SEQ ID NO 18
<211> LENGTH: 544
<212> TYPE: PRT
<213> ORGANISM: Oryza sativa

<400> SEQUENCE: 18

```
Met Lys Ser Pro Met Glu Glu Ala His Ala Met Pro Val Thr Ser Phe
 1               5                  10                  15
Phe Pro Val Ala Gly Ile His Lys Leu Ile Ala Ile Phe Leu Val Val
             20                  25                  30
```

```
Leu Ser Trp Ile Leu Val His Lys Trp Ser Leu Arg Asn Gln Lys Gly
            35                  40                  45

Pro Arg Ser Trp Pro Ile Ile Gly Ala Thr Val Glu Gln Leu Lys Asn
 50                  55                  60

Tyr His Arg Met His Asp Trp Leu Val Glu Tyr Leu Ser Lys Asp Arg
 65                  70                  75                  80

Thr Val Thr Val Asp Met Pro Phe Thr Ser Tyr Thr Tyr Ile Ala Asp
                 85                  90                  95

Pro Val Asn Val Glu His Val Leu Lys Thr Asn Phe Thr Asn Tyr Pro
                100                 105                 110

Lys Gly Glu Val Tyr Arg Ser Tyr Met Asp Val Leu Leu Gly Asp Gly
            115                 120                 125

Ile Phe Asn Ala Asp Gly Glu Met Trp Arg Lys Gln Arg Lys Thr Ala
            130                 135                 140

Ser Phe Glu Phe Ala Ser Lys Asn Leu Arg Asp Phe Ser Thr Val Val
145                 150                 155                 160

Phe Arg Glu Tyr Ser Leu Lys Leu Ser Ser Ile Leu Ser Gln Ala Cys
                165                 170                 175

Lys Ala Gly Arg Val Val Asp Met Gln Glu Leu Phe Met Arg Met Thr
            180                 185                 190

Leu Asp Ser Ile Cys Lys Val Gly Phe Gly Val Glu Ile Gly Thr Leu
            195                 200                 205

Ser Pro Asp Leu Pro Glu Asn Ser Phe Ala Gln Ala Phe Asp Ala Ala
            210                 215                 220

Asn Ile Ile Val Thr Leu Arg Phe Ile Asp Pro Leu Trp Arg Leu Lys
225                 230                 235                 240

Lys Phe Leu His Val Gly Ser Glu Ala Leu Glu Gln Ser Met Lys
                245                 250                 255

Leu Val Asp Asp Phe Thr Tyr Ser Val Ile Arg Arg Lys Ala Glu
            260                 265                 270

Ile Leu Gln Ala Arg Ala Ser Gly Lys Gln Glu Lys Ile Lys His Asp
            275                 280                 285

Ile Leu Ser Arg Phe Ile Glu Leu Gly Glu Ala Gly Gly Asp Glu Gly
            290                 295                 300

Gly Gly Ser Phe Gly Asp Asp Lys Ser Leu Arg Asp Val Val Leu Asn
305                 310                 315                 320

Phe Val Ile Ala Gly Arg Asp Thr Thr Ala Thr Thr Leu Ser Trp Phe
                325                 330                 335

Thr Tyr Met Ala Met Thr His Pro Ala Val Ala Asp Lys Leu Arg Arg
            340                 345                 350

Glu Leu Ala Ala Phe Glu Asp Glu Arg Ala Arg Glu Glu Gly Val Ala
            355                 360                 365

Leu Ala Asp Ala Ala Gly Glu Ala Ser Phe Ala Ala Arg Val Ala Gln
            370                 375                 380

Phe Ala Ser Leu Leu Ser Tyr Asp Ala Val Gly Lys Leu Val Tyr Leu
385                 390                 395                 400

His Ala Cys Val Thr Glu Thr Leu Arg Leu Tyr Pro Ala Val Pro Gln
                405                 410                 415

Asp Pro Lys Gly Ile Val Glu Asp Val Leu Pro Asp Gly Thr Lys
            420                 425                 430

Val Arg Ala Gly Gly Met Val Thr Tyr Val Pro Tyr Ser Met Gly Arg
            435                 440                 445
```

```
Met Glu Tyr Asn Trp Gly Pro Asp Ala Ala Ser Phe Arg Pro Glu Arg
    450                 455                 460

Trp Leu Ser Gly Asp Gly Ala Phe Arg Asn Ala Ser Pro Phe Lys
465                 470                 475                 480

Phe Thr Ala Phe Gln Ala Gly Pro Arg Ile Cys Leu Gly Lys Asp Ser
                485                 490                 495

Ala Tyr Leu Gln Met Lys Met Ala Leu Ala Ile Leu Phe Arg Phe Tyr
            500                 505                 510

Thr Phe Asp Leu Val Glu Asp His Pro Val Lys Tyr Arg Met Met Thr
        515                 520                 525

Ile Leu Ser Met Ala His Gly Leu Lys Val Arg Val Ser Thr Ser Val
    530                 535                 540
```

<210> SEQ ID NO 19
<211> LENGTH: 436
<212> TYPE: DNA
<213> ORGANISM: Sorghum sp.

<400> SEQUENCE: 19

```
aacgaatgta tcattgtgcc taaattttta aagaattgtg acaatttct ggtaggctga      60
gtttcagact ttcagtacca agctgatgga tcacattctg atccgaagt atgataacat     120
aatctggcaa ctcctaattg taataacaat gaataacctg caaatacagt ataagagtgg    180
ctcattttct tggttggcag atcacaaaaa ggaacacaaa ggctaagcgc caacttgtcc    240
gggagttagg tcatggatac catatgaatg aaagaaatct taatttccgg tcacaccaag    300
attgtctctc tcaaggttgg taacagcaat acccaatata tcacctaaca aacccagaca    360
acactacata cataacatcc atcacttgga gactggaccc ttcatcaaga gcaccatgga    420
ggaagctcac ctcatg                                                    436
```

<210> SEQ ID NO 20
<211> LENGTH: 450
<212> TYPE: DNA
<213> ORGANISM: Oryza sativa

<400> SEQUENCE: 20

```
aagcctggtt tcagttggtg acaatttaac agaattcaga tggatatggt tctgatatta      60
gaaggtggca taccttttagt cgctgcaaac gcttcagtta tctgaacaaa acaacgaact    120
tggctgagca ggggaaaaaa atactgtagc attcattttg tgtttacatg agtaacgatt    180
cttttctagg tggacagatc acaaaaagaa actaaagct aagatccaac tcctaagggt    240
gttaggttag ggacaccata tgaatgagac aatcttaatt cttggtcaca caaagattgt    300
ctcaaggttg gtagcatcag tgcccaatat atcacctaac tatgccatcc aaaatgctac    360
atagcatctc ttgtagactg aacccttcat gaagagcccc atggaggaag ctcatgcaat    420
gccagtgaca tcattcttcc cagtagcagg                                     450
```

<210> SEQ ID NO 21
<211> LENGTH: 543
<212> TYPE: PRT
<213> ORGANISM: Zea mays

<400> SEQUENCE: 21

```
Met Glu Glu Ala His Leu Thr Pro Ala Thr Pro Ser Pro Phe Phe Pro
1               5                   10                  15

Leu Ala Gly Pro His Lys Tyr Ile Ala Leu Leu Leu Val Val Leu Ser
            20                  25                  30
```

-continued

```
Trp Ile Leu Val Gln Arg Trp Ser Leu Arg Lys Gln Lys Gly Pro Arg
             35                  40                  45

Ser Trp Pro Val Ile Gly Ala Thr Val Glu Gln Leu Arg Asn Tyr His
 50                  55                  60

Arg Met His Asp Trp Leu Val Gly Tyr Leu Ser Arg His Arg Thr Val
 65                  70                  75                  80

Thr Val Asp Met Pro Phe Thr Ser Tyr Thr Tyr Ile Ala Asp Pro Val
                 85                  90                  95

Asn Val Glu His Val Leu Lys Thr Asn Phe Thr Asn Tyr Pro Lys Gly
                100                 105                 110

Ile Val Tyr Arg Ser Tyr Met Asp Val Leu Leu Gly Asp Gly Ile Phe
            115                 120                 125

Asn Ala Asp Gly Glu Leu Trp Arg Lys Gln Arg Lys Thr Ala Ser Phe
        130                 135                 140

Glu Phe Ala Ser Lys Asn Leu Arg Asp Phe Ser Ala Ile Val Phe Arg
145                 150                 155                 160

Glu Tyr Ser Leu Lys Leu Ser Gly Ile Leu Ser Gln Ala Ser Lys Ala
                165                 170                 175

Gly Lys Val Val Asp Met Gln Glu Leu Tyr Met Arg Met Thr Leu Asp
            180                 185                 190

Ser Ile Cys Lys Val Gly Phe Gly Val Glu Ile Gly Thr Leu Ser Pro
        195                 200                 205

Asp Leu Pro Glu Asn Ser Phe Ala Gln Ala Phe Asp Ala Ala Asn Ile
    210                 215                 220

Ile Ile Thr Leu Arg Phe Ile Asp Pro Leu Trp Arg Ile Lys Arg Phe
225                 230                 235                 240

Phe His Val Gly Ser Glu Ala Leu Leu Ala Gln Ser Ile Lys Leu Val
                245                 250                 255

Asp Glu Phe Thr Tyr Ser Val Ile Arg Arg Lys Ala Glu Ile Val
            260                 265                 270

Glu Val Arg Ala Ser Gly Lys Gln Glu Lys Met Lys His Asp Ile Leu
        275                 280                 285

Ser Arg Phe Ile Glu Leu Gly Glu Ala Gly Asp Asp Gly Gly Phe
    290                 295                 300

Gly Asp Asp Lys Ser Leu Arg Asp Val Leu Asn Phe Val Ile Ala
305                 310                 315                 320

Gly Arg Asp Thr Thr Ala Thr Thr Leu Ser Trp Phe Thr His Met Ala
                325                 330                 335

Met Ser His Pro Asp Val Ala Glu Lys Leu Arg Arg Glu Leu Cys Ala
            340                 345                 350

Phe Glu Ala Glu Arg Ala Arg Glu Glu Gly Val Thr Leu Val Leu Cys
        355                 360                 365

Gly Gly Ala Asp Ala Asp Lys Ala Phe Ala Ala Arg Val Ala Gln
    370                 375                 380

Phe Ala Gly Leu Leu Thr Tyr Asp Ser Leu Gly Lys Leu Val Tyr Leu
385                 390                 395                 400

His Ala Cys Val Thr Glu Thr Leu Arg Leu Tyr Pro Ala Val Pro Gln
                405                 410                 415

Asp Pro Lys Gly Ile Leu Glu Asp Val Leu Pro Asp Gly Thr Lys
            420                 425                 430

Val Arg Ala Gly Gly Met Val Thr Tyr Val Pro Tyr Ser Met Gly Arg
        435                 440                 445
```

```
Met Glu Tyr Asn Trp Gly Pro Asp Ala Ala Ser Phe Arg Pro Glu Arg
    450                 455                 460

Trp Ile Asn Glu Asp Gly Ala Phe Arg Asn Ala Ser Pro Phe Lys Phe
465                 470                 475                 480

Thr Ala Phe Gln Ala Gly Pro Arg Ile Cys Leu Gly Lys Asp Ser Ala
                485                 490                 495

Tyr Leu Gln Met Lys Met Ala Leu Ala Ile Leu Phe Arg Phe Tyr Ser
            500                 505                 510

Phe Arg Leu Leu Glu Gly His Pro Val Gln Tyr Arg Met Met Thr Ile
        515                 520                 525

Leu Ser Met Ala His Gly Leu Lys Val Arg Val Ser Arg Ala Val
    530                 535                 540

<210> SEQ ID NO 22
<211> LENGTH: 532
<212> TYPE: PRT
<213> ORGANISM: Sorghum sp.

<400> SEQUENCE: 22

Met Pro Ala Thr Pro Leu Phe Pro Leu Ala Gly Leu His Lys Tyr Ile
1               5                   10                  15

Ala Ile Leu Leu Val Val Leu Ser Trp Ala Leu Val His Arg Trp Ser
                20                  25                  30

Leu Arg Lys Gln Lys Gly Pro Arg Ser Trp Pro Val Ile Gly Ala Thr
            35                  40                  45

Leu Glu Gln Leu Arg Asn Tyr His Arg Met His Asp Trp Leu Val Gly
        50                  55                  60

Tyr Leu Ser Arg His Lys Thr Val Thr Val Asp Met Pro Phe Thr Ser
65                  70                  75                  80

Tyr Thr Tyr Ile Ala Asp Pro Val Asn Val Glu His Val Leu Lys Thr
                85                  90                  95

Asn Phe Thr Asn Tyr Pro Lys Gly Asp Val Tyr Arg Ser Tyr Met Asp
                100                 105                 110

Val Leu Leu Gly Asp Gly Ile Phe Asn Ala Asp Gly Glu Leu Trp Arg
            115                 120                 125

Lys Gln Arg Lys Thr Ala Ser Phe Glu Phe Ala Ser Lys Asn Leu Arg
        130                 135                 140

Asp Phe Ser Ala Asn Val Phe Arg Glu Tyr Ser Leu Lys Leu Ser Gly
145                 150                 155                 160

Ile Leu Ser Gln Ala Ser Lys Ala Gly Lys Val Val Asp Met Gln Glu
                165                 170                 175

Leu Tyr Met Arg Met Thr Leu Asp Ser Ile Cys Lys Val Gly Phe Gly
            180                 185                 190

Val Glu Ile Gly Thr Leu Ser Pro Asp Leu Pro Glu Asn Ser Phe Ala
        195                 200                 205

Gln Ala Phe Asp Ala Ala Asn Ile Ile Val Thr Leu Arg Phe Ile Asp
    210                 215                 220

Pro Leu Trp Arg Val Lys Arg Phe Phe His Val Gly Ser Glu Ala Leu
225                 230                 235                 240

Leu Ala Gln Ser Ile Lys Leu Val Asp Glu Phe Thr Tyr Ser Val Ile
                245                 250                 255

Arg Arg Arg Lys Ala Glu Ile Val Glu Ala Arg Ala Ser Gly Lys Gln
            260                 265                 270

Glu Lys Met Lys His Asp Ile Leu Ser Arg Phe Ile Glu Leu Gly Glu
        275                 280                 285
```

```
Ala Gly Asp Asp Gly Gly Phe Gly Asp Lys Ser Leu Arg Asp Val
    290                 295                 300

Val Leu Asn Phe Val Ile Ala Gly Arg Asp Thr Thr Ala Thr Thr Leu
305                 310                 315                 320

Ser Trp Phe Thr His Met Ala Met Ser His Pro Asp Val Ala Glu Lys
                325                 330                 335

Leu Arg Arg Glu Leu Cys Ala Phe Glu Ala Glu Arg Ala Arg Glu Glu
                340                 345                 350

Gly Val Ala Val Pro Cys Cys Gly Pro Asp Asp Lys Ala Phe Ala
    355                 360                 365

Ala Arg Val Ala Gln Phe Ala Gly Leu Leu Thr Tyr Asp Ser Leu Gly
    370                 375                 380

Lys Leu Val Tyr Leu His Ala Cys Val Thr Glu Thr Leu Arg Leu Tyr
385                 390                 395                 400

Pro Ala Val Pro Gln Asp Pro Lys Gly Ile Leu Glu Asp Asp Val Leu
                405                 410                 415

Pro Asp Gly Thr Lys Val Arg Ala Gly Met Val Thr Tyr Val Pro
    420                 425                 430

Tyr Ser Met Gly Arg Met Glu Tyr Asn Trp Gly Pro Asp Ala Ala Ser
    435                 440                 445

Phe Arg Pro Glu Arg Trp Ile Asn Glu Glu Gly Ala Phe Arg Asn Ala
    450                 455                 460

Ser Pro Phe Lys Phe Thr Ala Phe Gln Ala Gly Pro Arg Ile Cys Leu
465                 470                 475                 480

Gly Lys Asp Ser Ala Tyr Leu Gln Met Lys Met Ala Leu Ala Ile Leu
                485                 490                 495

Phe Arg Phe Tyr Ser Phe Gln Leu Leu Gly His Pro Val Gln Tyr
                500                 505                 510

Arg Met Met Thr Ile Leu Ser Met Ala His Gly Leu Lys Val Arg Val
                515                 520                 525

Ser Arg Ala Val
    530

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tagggdtgaa aacgg                                                      15

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
```

```
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (9)
<223> OTHER INFORMATION: Variable amino acid

<400> SEQUENCE: 24

Phe Xaa Xaa Gly Xaa Arg Xaa Cys Xaa Gly
1               5                   10

<210> SEQ ID NO 25
<211> LENGTH: 10
<212> TYPE: PRT
<213> ORGANISM: Zea mays

<400> SEQUENCE: 25

Phe Gln Ala Gly Pro Arg Ile Cys Leu Gly
1               5                   10

<210> SEQ ID NO 26
<211> LENGTH: 1618
<212> TYPE: DNA
<213> ORGANISM: Zea mays
<220> FEATURE:
<221> NAME/KEY: CDS
<222> LOCATION: (108)..(1430)

<400> SEQUENCE: 26
ggcacgagcc ggcgagccca ctcggcagtc ggcacaacca cacacacctc cacccactct      60
ctgagataag tgaagcatct cgcgcactgt cgcagtcgca gacggag atg atg aag       116
                                                    Met Met Lys
                                                      1 cac tcg agc agc ttg tgc ttg ctc ttc ctc ttg gcg ctc tgc acc acc       164
His Ser Ser Ser Leu Cys Leu Leu Phe Leu Leu Ala Leu Cys Thr Thr
      5                  10                  15 ctg ctg gcc tgc ggc ctg gtc cag gca caa gtc ctc ttc cag ggg ttt       212
Leu Leu Ala Cys Gly Leu Val Gln Ala Gln Val Leu Phe Gln Gly Phe
 20                  25                  30                  35 aac tgg gag tcg tgc aag cag cag gga ggc tgg tac aac agg ctc aag       260
Asn Trp Glu Ser Cys Lys Gln Gln Gly Gly Trp Tyr Asn Arg Leu Lys
                 40                  45                  50 gcc cag gtc gac gac atc gcc aag gcc ggc gtc acg cac gtc tgg ctg       308
Ala Gln Val Asp Asp Ile Ala Lys Ala Gly Val Thr His Val Trp Leu
             55                  60                  65 cct cca ccc tcg cac tcc gtc tcg cca caa ggc tac atg cca ggc cgc       356
Pro Pro Pro Ser His Ser Val Ser Pro Gln Gly Tyr Met Pro Gly Arg
         70                  75                  80 cta tac gac ctg gac gcg tcc aag tac ggc acg gcg gcg gag ctc aag       404
Leu Tyr Asp Leu Asp Ala Ser Lys Tyr Gly Thr Ala Ala Glu Leu Lys
     85                  90                  95 tcc ctg ata gcg gcg ttc cac ggc agg ggc gtg cag tgc gtg gcg gac       452
Ser Leu Ile Ala Ala Phe His Gly Arg Gly Val Gln Cys Val Ala Asp
100                 105                 110                 115 atc gtc atc aac cac cgg tgc gcg gaa aag aag gac gcg cgc ggc gtg       500
Ile Val Ile Asn His Arg Cys Ala Glu Lys Lys Asp Ala Arg Gly Val
                120                 125                 130 tac tgc atc ttc gag ggc ggg act ccc gac gac gcg ctg gac tgg ggc       548
Tyr Cys Ile Phe Glu Gly Gly Thr Pro Asp Asp Ala Leu Asp Trp Gly
            135                 140                 145 ccc ggg atg atc tgc agc gac gac acg cag tac tcg gac ggg acg ggg       596
Pro Gly Met Ile Cys Ser Asp Asp Thr Gln Tyr Ser Asp Gly Thr Gly
```

-continued

```
                150                 155                 160
cac cgc gac acg ggc gag ggg ttc gcg gcg gcg ccc gac atc gac cac    644
His Arg Asp Thr Gly Glu Gly Phe Ala Ala Ala Pro Asp Ile Asp His
    165                 170                 175 ctc aac ccg cgc gtg cag cgg gag ctc tcc gcc tgg ctc aac tgg ctc    692
Leu Asn Pro Arg Val Gln Arg Glu Leu Ser Ala Trp Leu Asn Trp Leu
180                 185                 190                 195 agg tcc gac gcc gtg ggg ttc gac ggc tgg cgc ctc gac ttc gcc aag    740
Arg Ser Asp Ala Val Gly Phe Asp Gly Trp Arg Leu Asp Phe Ala Lys
                200                 205                 210 ggc tac tcg ccg gcc gtc gcc aga atg tac gtg gag agc acg ggg ccg    788
Gly Tyr Ser Pro Ala Val Ala Arg Met Tyr Val Glu Ser Thr Gly Pro
            215                 220                 225 ccg agc ttc gtc gtc gcg gag ata tgg aac tcg ctg agc tac agc ggg    836
Pro Ser Phe Val Val Ala Glu Ile Trp Asn Ser Leu Ser Tyr Ser Gly
        230                 235                 240 gac ggc aag ccg gcg ccc aac cag gac cag tgc cgg cag gag ctg ctg    884
Asp Gly Lys Pro Ala Pro Asn Gln Asp Gln Cys Arg Gln Glu Leu Leu
    245                 250                 255 gac tgg acg cgg gcc gtc ggc ggg ccc gcc atg gcg ttc gac ttc ccc    932
Asp Trp Thr Arg Ala Val Gly Gly Pro Ala Met Ala Phe Asp Phe Pro
260                 265                 270                 275 acc aag ggc ctg ctg cag gcg ggc gtg cag ggg gag ctg tgg cgg ctg    980
Thr Lys Gly Leu Leu Gln Ala Gly Val Gln Gly Glu Leu Trp Arg Leu
                280                 285                 290 cgc gac agc tcc ggc aac gcg gcc ggc ctg atc ggg tgg gcg ccc gag   1028
Arg Asp Ser Ser Gly Asn Ala Ala Gly Leu Ile Gly Trp Ala Pro Glu
            295                 300                 305 aag gcc gtc acc ttc gtc gac aac cat gac acc ggg tcg acg cag aag   1076
Lys Ala Val Thr Phe Val Asp Asn His Asp Thr Gly Ser Thr Gln Lys
        310                 315                 320 ctc tgg ccg ttc cca tcc gac aag gtc atg cag ggc tac gcc tac atc   1124
Leu Trp Pro Phe Pro Ser Asp Lys Val Met Gln Gly Tyr Ala Tyr Ile
    325                 330                 335 ctc acc cat cca gga gtc ccc tgc att ttc tac gac cac atg ttc gac   1172
Leu Thr His Pro Gly Val Pro Cys Ile Phe Tyr Asp His Met Phe Asp
340                 345                 350                 355 tgg aac ctg aag cag gag ata tcc acg ctg tct gcc atc agg gcg cgg   1220
Trp Asn Leu Lys Gln Glu Ile Ser Thr Leu Ser Ala Ile Arg Ala Arg
                360                 365                 370 aac ggc atc cgc gcc ggg agc aag ctg cgg atc ctc gtg gcg gac gcg   1268
Asn Gly Ile Arg Ala Gly Ser Lys Leu Arg Ile Leu Val Ala Asp Ala
            375                 380                 385 gac gcg tac gtg gcc gtc gtc gac gag aag gtc atg gtg aag atc ggg   1316
Asp Ala Tyr Val Ala Val Val Asp Glu Lys Val Met Val Lys Ile Gly
        390                 395                 400 aca agg tac ggc gtg agc agc gtg gtc ccg tcg gat ttc cac ccg gcg   1364
Thr Arg Tyr Gly Val Ser Ser Val Val Pro Ser Asp Phe His Pro Ala
    405                 410                 415 gcg cac ggc aag gac tac tgc gtc tgg gag aaa gcg agc ctc cgc gtc   1412
Ala His Gly Lys Asp Tyr Cys Val Trp Glu Lys Ala Ser Leu Arg Val
420                 425                 430                 435 ccg gcg ggg cgc cac ctc tagcagctca gattgctcag tcttgtgctg           1460
Pro Ala Gly Arg His Leu
                440 cattgcaaac acagcagcac gacactgcat aacgtctttt ccttaatttc ctgaatttta  1520 ccttttccta gttcaatttc atatatgtat ttctacatgt acacactatc acaatcagat  1580 aaataaacaa gcttggtcaa aaaaaaaaaa aaaaaaa                           1618
```

```
<210> SEQ ID NO 27
<211> LENGTH: 13
<212> TYPE: PRT
<213> ORGANISM: Zea mays

<400> SEQUENCE: 27

Leu Val Tyr Leu His Ala Cys Val Thr Glu Thr Leu Arg
 1               5                  10

<210> SEQ ID NO 28
<211> LENGTH: 42
<212> TYPE: PRT
<213> ORGANISM: Zea mays

<400> SEQUENCE: 28

Cys His Gly Asp Leu Asp Met Asp Ile Val Pro Leu Asn Pro Arg Gln
 1               5                  10                  15

Ile Thr Leu Val Leu Gln Ile Cys Met His Ala Cys Lys Gly Lys Arg
             20                  25                  30

Trp Val Ser Leu Val Ala Trp Leu Lys Pro
         35                  40

<210> SEQ ID NO 29
<211> LENGTH: 28
<212> TYPE: PRT
<213> ORGANISM: Zea mays

<400> SEQUENCE: 29

Lys Leu Arg Arg Val Leu Arg Thr Thr Thr Ser Leu Val Phe Cys Thr
 1               5                  10                  15

Leu Leu Leu Ser Gly Ser Val Val Thr Ala Tyr Lys
             20                  25

<210> SEQ ID NO 30
<211> LENGTH: 42
<212> TYPE: PRT
<213> ORGANISM: Zea mays

<400> SEQUENCE: 30

Cys His Gly Asp Leu Asp Met Asp Ile Val Pro Leu Asn Pro Arg Gln
 1               5                  10                  15

Ile Thr Leu Val Leu Gln Ile Cys Met His Ala Cys Lys Gly Lys Arg
             20                  25                  30

Trp Val Ser Leu Val Ala Trp Leu Lys Pro
         35                  40

<210> SEQ ID NO 31
<211> LENGTH: 14
<212> TYPE: PRT
<213> ORGANISM: Zea mays

<400> SEQUENCE: 31

Lys Leu Arg Arg Val Leu Arg Thr Thr Thr Ser Leu Val Phe
 1               5                  10

<210> SEQ ID NO 32
<211> LENGTH: 24
<212> TYPE: PRT
<213> ORGANISM: Zea mays

<400> SEQUENCE: 32
```

-continued

```
Arg Trp Arg Trp Pro Ser Ser Cys Ala Ser Thr Ala Ser Gly Cys Trp
1               5                   10                  15

Arg Gly Thr Arg Cys Ser Thr Ala
            20
```

<210> SEQ ID NO 33
<211> LENGTH: 11
<212> TYPE: PRT
<213> ORGANISM: Zea mays

<400> SEQUENCE: 33

```
Pro Ser Ser Pro Trp Arg Thr Lys Gly Glu Phe
1               5                   10
```

<210> SEQ ID NO 34
<211> LENGTH: 42
<212> TYPE: PRT
<213> ORGANISM: Zea mays

<400> SEQUENCE: 34

```
Cys His Gly Asp Leu Asp Met Asp Ile Val Pro Leu Asn Pro Arg Gln
1               5                   10                  15

Ile Thr Leu Val Leu Gln Ile Cys Met His Ala Cys Lys Gly Lys Arg
            20                  25                  30

Trp Val Ser Leu Val Ala Trp Leu Lys Pro
            35                  40
```

<210> SEQ ID NO 35
<211> LENGTH: 6
<212> TYPE: PRT
<213> ORGANISM: Zea mays

<400> SEQUENCE: 35

```
Ala Gly Arg Asp Thr Thr
1               5
```

<210> SEQ ID NO 36
<211> LENGTH: 441
<212> TYPE: PRT
<213> ORGANISM: Zea mays

<400> SEQUENCE: 36

```
Met Met Lys His Ser Ser Ser Leu Cys Leu Leu Phe Leu Leu Ala Leu
1               5                   10                  15

Cys Thr Thr Leu Leu Ala Cys Gly Leu Val Gln Ala Gln Val Leu Phe
            20                  25                  30

Gln Gly Phe Asn Trp Glu Ser Cys Lys Gln Gln Gly Gly Trp Tyr Asn
            35                  40                  45

Arg Leu Lys Ala Gln Val Asp Asp Ile Ala Lys Ala Gly Val Thr His
        50                  55                  60

Val Trp Leu Pro Pro Ser His Ser Val Ser Pro Gln Gly Tyr Met
65                  70                  75                  80

Pro Gly Arg Leu Tyr Asp Leu Asp Ala Ser Lys Tyr Gly Thr Ala Ala
                85                  90                  95

Glu Leu Lys Ser Leu Ile Ala Ala Phe His Gly Arg Gly Val Gln Cys
            100                 105                 110

Val Ala Asp Ile Val Ile Asn His Arg Cys Ala Glu Lys Lys Asp Ala
            115                 120                 125

Arg Gly Val Tyr Cys Ile Phe Glu Gly Gly Thr Pro Asp Asp Arg Leu
        130                 135                 140
```

```
Asp Trp Gly Pro Gly Met Ile Cys Ser Asp Asp Thr Gln Tyr Ser Asp
145                 150                 155                 160

Gly Thr Gly His Arg Asp Thr Gly Glu Gly Phe Ala Ala Ala Pro Asp
            165                 170                 175

Ile Asp His Leu Asn Pro Arg Val Gln Arg Glu Leu Ser Ala Trp Leu
                180                 185                 190

Asn Trp Leu Arg Ser Asp Ala Val Gly Phe Asp Gly Trp Arg Leu Asp
            195                 200                 205

Phe Ala Lys Gly Tyr Ser Pro Ala Val Ala Arg Met Tyr Val Glu Ser
        210                 215                 220

Thr Gly Pro Pro Ser Phe Val Val Ala Glu Ile Trp Asn Ser Leu Ser
225                 230                 235                 240

Tyr Ser Gly Asp Gly Lys Pro Ala Pro Asn Gln Asp Gln Cys Arg Gln
                245                 250                 255

Glu Leu Leu Asp Trp Thr Arg Ala Val Gly Gly Pro Ala Met Ala Phe
            260                 265                 270

Asp Phe Pro Thr Lys Gly Leu Leu Gln Ala Gly Val Gln Gly Glu Leu
        275                 280                 285

Trp Arg Leu Arg Asp Ser Ser Gly Asn Ala Ala Gly Leu Ile Gly Trp
    290                 295                 300

Ala Pro Glu Lys Ala Val Thr Phe Val Asp Asn His Asp Thr Gly Ser
305                 310                 315                 320

Thr Gln Lys Leu Trp Pro Phe Pro Ser Asp Lys Val Met Gln Gly Tyr
                325                 330                 335

Ala Tyr Ile Leu Thr His Pro Gly Val Pro Cys Ile Phe Tyr Asp His
            340                 345                 350

Met Phe Asp Trp Asn Leu Lys Gln Glu Ile Ser Thr Leu Ser Ala Ile
        355                 360                 365

Arg Ala Arg Asn Gly Ile Arg Ala Gly Ser Lys Leu Arg Ile Leu Val
    370                 375                 380

Ala Asp Ala Asp Ala Tyr Val Ala Val Val Asp Glu Lys Val Met Val
385                 390                 395                 400

Lys Ile Gly Thr Arg Tyr Gly Val Ser Ser Val Val Pro Ser Asp Phe
                405                 410                 415

His Pro Ala Ala His Gly Lys Asp Tyr Cys Val Trp Glu Lys Ala Ser
            420                 425                 430

Leu Arg Val Pro Ala Gly Arg His Leu
        435                 440
```